United States Patent
Buelna

(10) Patent No.: US 12,194,001 B2
(45) Date of Patent: *Jan. 14, 2025

(54) TREATMENT OF KIDNEY DISEASE BY RENAL PELVIS ABLATION

(71) Applicant: Verve Medical, Inc., Paradise Valley, AZ (US)

(72) Inventor: Terrence J. Buelna, Sunset Beach, CA (US)

(73) Assignee: Verve Medical, Inc., Paradise, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/412,240

(22) Filed: Jan. 12, 2024

(65) Prior Publication Data

US 2024/0189253 A1  Jun. 13, 2024

Related U.S. Application Data

(60) Continuation of application No. 18/374,612, filed on Sep. 28, 2023, which is a continuation-in-part of
(Continued)

(51) Int. Cl.
*A61K 31/045* (2006.01)
*A61B 17/32* (2006.01)
(Continued)

(52) U.S. Cl.
CPC ........ *A61K 31/045* (2013.01); *A61B 18/1492* (2013.01); *A61B 2017/320008* (2013.01);
(Continued)

(58) Field of Classification Search
CPC .. A61B 2018/0016; A61B 2018/00214; A61B 2018/00511; A61B 2018/1407;
(Continued)

(56) References Cited

U.S. PATENT DOCUMENTS 8,548,600 B2   10/2013   Deem et al.
9,668,811 B2    6/2017   Sogard et al.
(Continued)

FOREIGN PATENT DOCUMENTS

JP   2013544133   12/2013
WO      9744088   11/1997
(Continued)

OTHER PUBLICATIONS

Kopp, U. C. (2011). Neural control of renal function, Colloquium Series in Integrated Systems Physiology: From Molecule to Function, Morgan & Claypool Life Sciences. (Submitted as Exhibit B to the DiBona Declaration on Feb. 9, 2024).
(Continued)

*Primary Examiner* — Ronald Hupczey, Jr.
(74) *Attorney, Agent, or Firm* — Gardella Grace P.A.

(57) ABSTRACT

In an illustrative embodiment, systems and methods for treatment of nerves present in a wall of a human renal pelvis are described. One system uses a sheath to access a position in or near the renal pelvis via the urinary tract. An effector inserted through the sheath has an uncooled distal region formed with a superelastic wire that supports at least four non-insulated, preferably spherical electrodes distributed along the distal region. The distal region expands within the renal pelvis, and vacuum applied through the sheath at least partially evacuates the renal pelvis to draw opposing walls of the renal pelvis inwards and compress the distal region somewhat from its expanded form, placing the electrodes in intimate contact with different points along the renal pelvic wall. Energy is applied to the electrodes to create discrete lesions at the points of contact of the electrodes.

10 Claims, 39 Drawing Sheets

Related U.S. Application Data application No. 17/097,387, filed on Nov. 13, 2020, which is a division of application No. 14/616,576, filed on Feb. 6, 2015, now abandoned.

(60) Provisional application No. 63/410,840, filed on Sep. 28, 2022, provisional application No. 62/074,894, filed on Nov. 4, 2014, provisional application No. 62/003,918, filed on May 28, 2014, provisional application No. 61/937,353, filed on Feb. 7, 2014.

(51) Int. Cl.

| | | |
|---|---|---|
| *A61B 18/00* | (2006.01) | |
| *A61B 18/04* | (2006.01) | |
| *A61B 18/14* | (2006.01) | |
| *A61B 18/18* | (2006.01) | |
| *A61N 1/32* | (2006.01) | |
| *A61N 7/02* | (2006.01) | |

(52) U.S. Cl.
CPC ............ *A61B 2017/320069* (2017.08); *A61B 2018/00214* (2013.01); *A61B 2018/0022* (2013.01); *A61B 2018/00267* (2013.01); *A61B 2018/00434* (2013.01); *A61B 2018/00511* (2013.01); *A61B 2018/00577* (2013.01); *A61B 2018/00797* (2013.01); *A61B 2018/00821* (2013.01); *A61B 2018/044* (2013.01); *A61B 2018/1417* (2013.01); *A61B 2018/1435* (2013.01); *A61B 2018/1861* (2013.01); *A61N 1/325* (2013.01); *A61N 7/022* (2013.01)

(58) Field of Classification Search
CPC .. A61B 2018/1417; A61B 2018/00404; A61B 2018/1467; A61B 2018/1475
See application file for complete search history.

(56) References Cited

U.S. PATENT DOCUMENTS

| | | | |
|---|---|---|---|
| 10,357,302 | B2 | 7/2019 | Buelna |
| 2003/0153905 | A1 | 8/2003 | Edwards et al. |
| 2009/0024195 | A1 | 1/2009 | Rezai et al. |
| 2011/0060324 | A1 | 3/2011 | Wu et al. |
| 2011/0104061 | A1 | 5/2011 | Seward |
| 2011/0301662 | A1 | 12/2011 | Bar-Yoseph et al. |
| 2012/0029513 | A1 | 2/2012 | Smith et al. |
| 2012/0078160 | A1 | 3/2012 | McMillan |
| 2012/0101538 | A1 | 4/2012 | Ballakur et al. |
| 2012/0116382 | A1 | 5/2012 | Ku et al. |
| 2012/0123303 | A1 | 5/2012 | Sogard et al. |
| 2012/0130368 | A1* | 5/2012 | Jenson ............... A61B 18/1492 606/41 |
| 2013/0053732 | A1 | 2/2013 | Heuser |
| 2013/0165926 | A1 | 6/2013 | Mathur et al. |
| 2013/0178824 | A1 | 7/2013 | Buelna |
| 2014/0107639 | A1 | 4/2014 | Zhang et al. |
| 2015/0065783 | A1 | 3/2015 | Buelna |
| 2015/0223866 | A1 | 8/2015 | Buelna et al. |
| 2015/0342531 | A1 | 12/2015 | Hoitink et al. |
| 2019/0329042 | A1 | 10/2019 | DiLorenzo |
| 2021/0077419 | A1 | 3/2021 | Buelna et al. |
| 2024/0099988 | A1 | 3/2024 | Buelna |
| 2024/0148423 | A1 | 5/2024 | Buelna |

FOREIGN PATENT DOCUMENTS

| | | | |
|---|---|---|---|
| WO | 2005000130 | 1/2005 | |
| WO | 2010067360 | 6/2010 | |
| WO | 2012061161 | 5/2012 | |
| WO | 2012170482 | 12/2012 | |
| WO | 2013010009 | 1/2013 | |
| WO | WO-2013010009 A1 * | 1/2013 | ............ A61B 18/00 |
| WO | 2013134469 | 9/2013 | |
| WO | WO-2013134469 A1 * | 9/2013 | ............ A61B 18/02 |
| WO | 2015120340 | 8/2015 | |

OTHER PUBLICATIONS

Dibona, G. F., & Esler, M. (2010). Translational medicine: the antihypertensive effect of renal denervation. American Journal of Physiology-Regulatory, Integrative and Comparative Physiology, 298(2), R245-R253. (Submitted as Exhibit C to the DiBona Declaration on Feb. 9, 2024).

Esler, M. (2011). The sympathetic nervous system through the ages: from Thomas Willis to resistant hypertension. Experimental physiology, 96(7), 611-622. (Submitted as Exhibit D to the DiBona Declaration on Feb. 9, 2024).

Vase, H., Mathiassen, O. N., Kaltoft, A., Pedersen, E. B., Christensen, K. L., Buus, N. H., . . . & Thuesen, L. (2012). Catheter-based renal denervation for treatment of resistant hypertension. Dan Med J, 59(6), A4439. (Submitted as Exhibit E to the DiBona Declaration on Feb. 9, 2024).

Zhang, Y., Hata, C., & De La Rama, A., Certified U.S. Appl. No. 61/493,849, filed Jun. 6, 2011, entitled "Renal Denervation System and Method," 17 pages. (Submitted as Exhibit F to the DiBona Declaration on Feb. 9, 2024).

Tunev, S. S., & Trudel, J., File History of U.S. Appl. No. 61/608,022, filed Mar. 7, 2012, entitled "Selective Modulation of Renal Nerves," 58 pages. (Submitted as Exhibit H to the DiBona Declaration on Feb. 9, 2024).

Mitterberger, M., Pinggera, G. M., Feuchtner, G., Neururer, R., Bartsch, G., Gradl, J., . . . & Frauscher, F. (2007). Sonographic measurement of renal pelvis wall thickness as diagnostic criterion for acute pyelonephritis in adults. Ultraschall in der Medizin-European Journal of Ultrasound, 28(06), 593-597. (Submitted as Exhibit I to the DiBona Declaration on Feb. 9, 2024).

Weizer, A. Z., Raj, G. V., O'Connell, M., Robertson, C. N., Nelson, R. C., & Polascik, T. J. (2005). Complications after percutaneous radiofrequency ablation of renal tumors. Urology, 66(6), 1176-1180. (Submitted as Exhibit K to the DiBona Declaration on Feb. 9, 2024).

Gervais, D. A., Arellano, R. S., McGovern, F. J., McDougal, W. S., & Mueller, P. R. (2005). Radiofrequency ablation of renal cell carcinoma: part 2, Lessons learned with ablation of 100 tumors. American Journal of Roentgenology, 185(1), 72-80. (Submitted as Exhibit M to the DiBona Declaration on Feb. 9, 2024).

Caliskan, S., & Cevik, R. (2016). Retroperitoneal urinoma after percutaneous nephrolithotomy. Medicine Science, 5(2), 720-724. (Submitted as Exhibit N to the DiBona Declaration on Feb. 9, 2024).

Sakakura, K., Ladich, E., Cheng, Q., Otsuka, F., Yahagi, K., Fowler, D. R., . . . & Joner, M. (2014). Anatomic assessment of sympathetic peri-arterial renal nerves in man. Journal of the American College of Cardiology, 64(7), 635-643. (Submitted as Exhibit O to the DiBona Declaration on Feb. 9, 2024).

Vink, E. E., Goldschmeding, R., Vink, A., Weggemans, C., Bleijs, R. L., & Blankestijn, P. J. (2014). Limited destruction of renal nerves after catheter-based renal denervation: results of a human case study. Nephrology Dialysis Transplantation, 29(8), 1608-1610. (Submitted as Exhibit P to the DiBona Declaration on Feb. 9, 2024).

Bhatt, D. L., Kandzari, D. E., O'Neill, W. W., D'Agostino, R., Flack, J. M., Katzen, B. T., . . . & Bakris, G. L. (2014). A controlled trial of renal denervation for resistant hypertension. New England Journal of Medicine, 370(15), 1393-1401. (Submitted as Exhibit Q to the DiBona Declaration on Feb. 9, 2024).

Schaeffer, A. J., Kurtz, M. P., Logvinenko, T., McCartin, M. T., Prabhu, S. P., Nelson, C. P., & Chow, J. S. (2016). MRI-based reference range for the renal pelvis anterior-posterior diameter in children ages 0-19 years. The British journal of radiology, 89(1067), Feb. 11, 2016. (Submitted as Exhibit R to the DiBona Declaration on Feb. 9, 2024).

Weber, M. A., Hering, D., Nikoleishvili, D., Imedadze, A., Dughashvili, G., Klimiashvili, Z., . . . & Provanzano, R. (2023). Durability of the Blood Pressure Effects of Renal Pelvis Denervation in Patients with

(56) References Cited

OTHER PUBLICATIONS

Hypertension During a 12-Month Observation. American Journal of Nephrology. (Submitted as Exhibit S to the DiBona Declaration on Feb. 9, 2024).

Buelna, T. J., & Gold, A., U.S. Appl. No. 62/074,894, filed Nov. 4, 2014, entitled "Methods and Systems for Surface Ablation of the Renal Pelvis," 36 pages.

Non-Final Office Action issued in related U.S. Appl. No. 17/097,387 on Oct. 11, 2022, 13 pages.

Final Office Action issued in related U.S. Appl. No. 17/097,387 on Mar. 27, 2023, 20 pages.

Non-Final Office Action issued in related U.S. Appl. No. 17/097,387 on Oct. 20, 2023, 14 pages.

Non-Final Office Action dated Apr. 9, 2024 issued in related U.S. Appl. No. 18/412,229, 7 pages.

Non-Final Office Action dated Jul. 18, 2024 in related U.S. Appl. No. 17/143,725, 7 pages.

Extended European Search Report dated Sep. 28, 2017 in European Patent Application No. 15746617.8, 5 pages. (Submitted in related U.S. Appl. No. 17/097,387).

International Search Report and Written Opinion dated Jul. 10, 2015 in International Application No. PCT/US2015/014926, 12 pages.

Final Office Action dated Jan. 26, 2018 issued in related U.S. Appl. No. 14/616,576, 11 pages. (Submitted in related U.S. Appl. No. 17/097,387).

Non-Final Office Action dated Feb. 26, 2019 issued in related U.S. Appl. No. 14/616,576, 9 pages. (Submitted in related U.S. Appl. No. 17/097,387).

Non-Final Office Action dated May 19, 2020 issued in related U.S. Appl. No. 14/616,576, 14 pages. (Submitted in related U.S. Appl. No. 17/097,387).

Non-Final Office Action dated Jun. 13, 2017 issued in related U.S. Appl. No. 14/616,576, 14 pages. (Submitted in related U.S. Appl. No. 17/097,387).

Final Office Action dated Nov. 13, 2019 issued in related U.S. Appl. No. 14/616,576, 11 pages. (Submitted in related U.S. Appl. No. 17/097,387).

\* cited by examiner

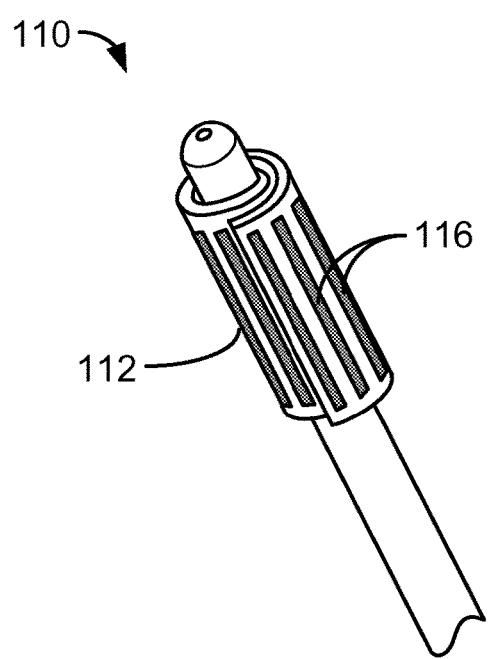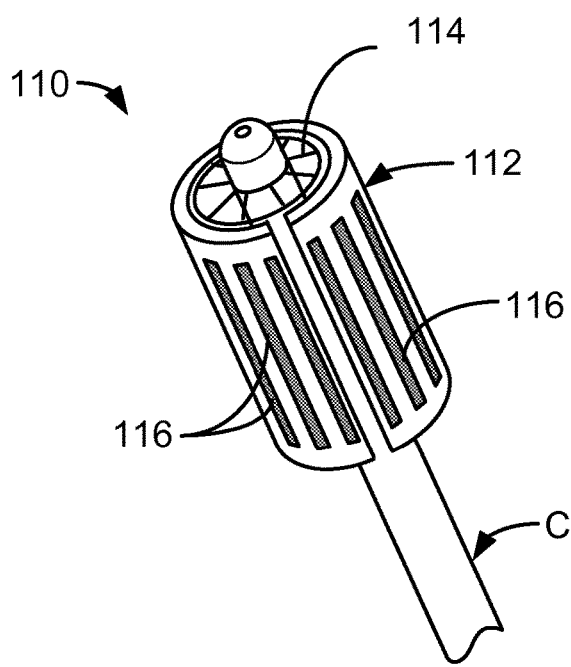
FIG. 9A  FIG. 9B

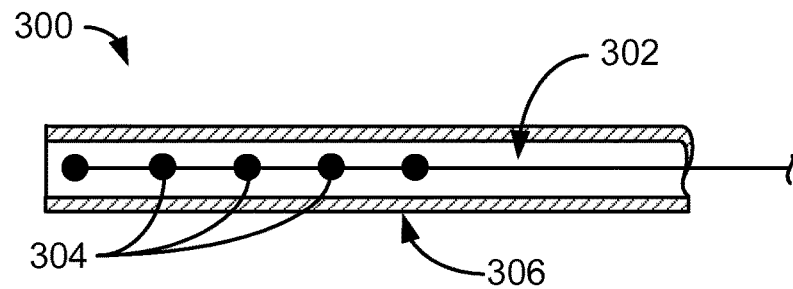
FIG. 27A
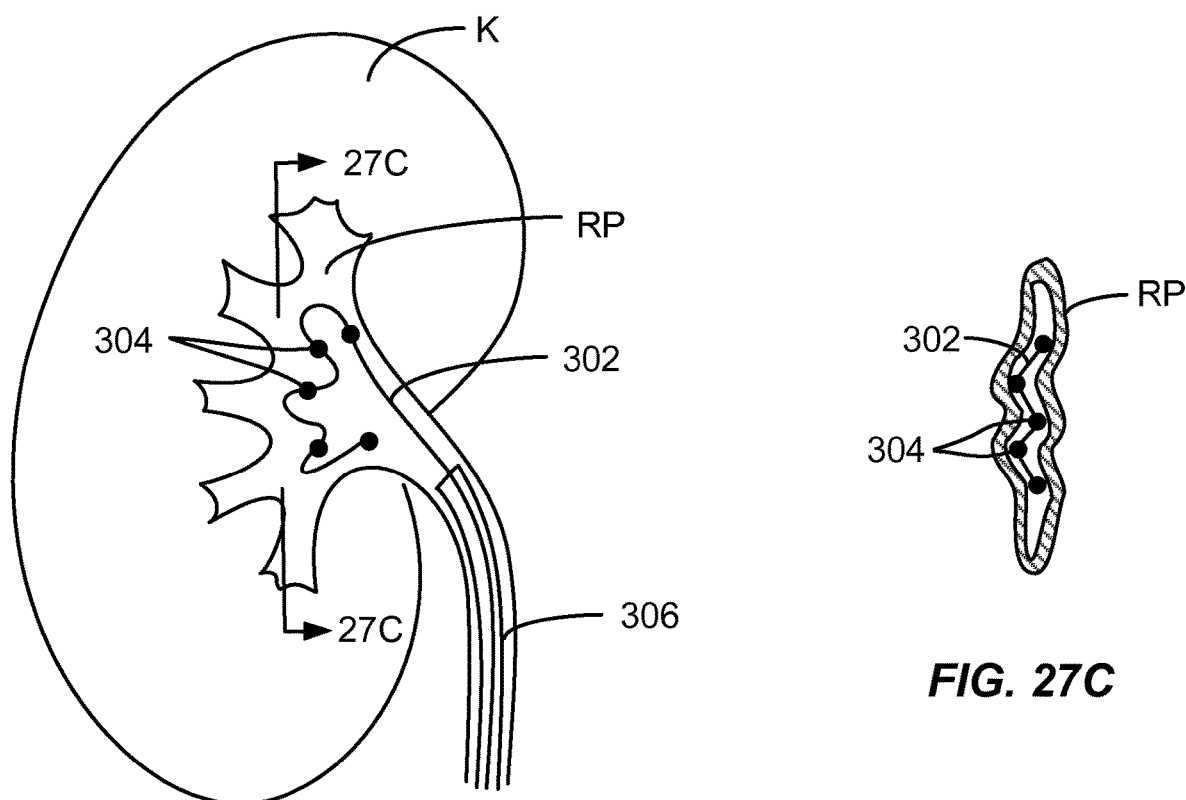
FIG. 27B
FIG. 27C

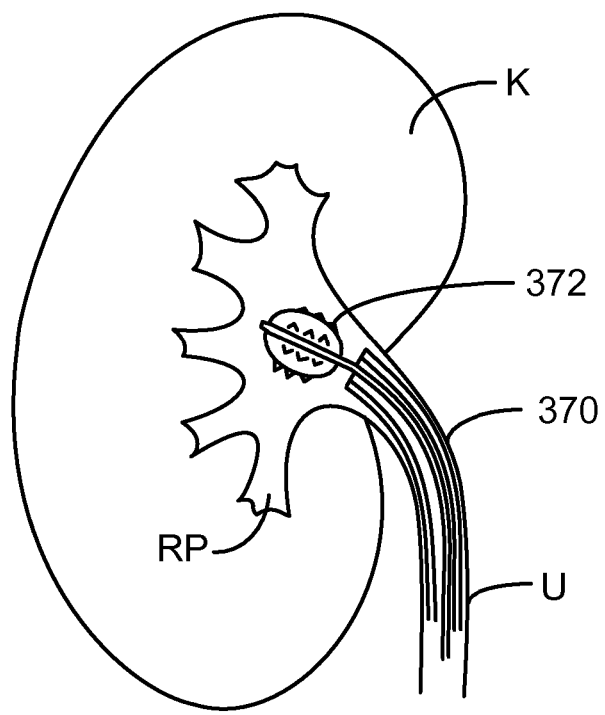
FIG. 34C
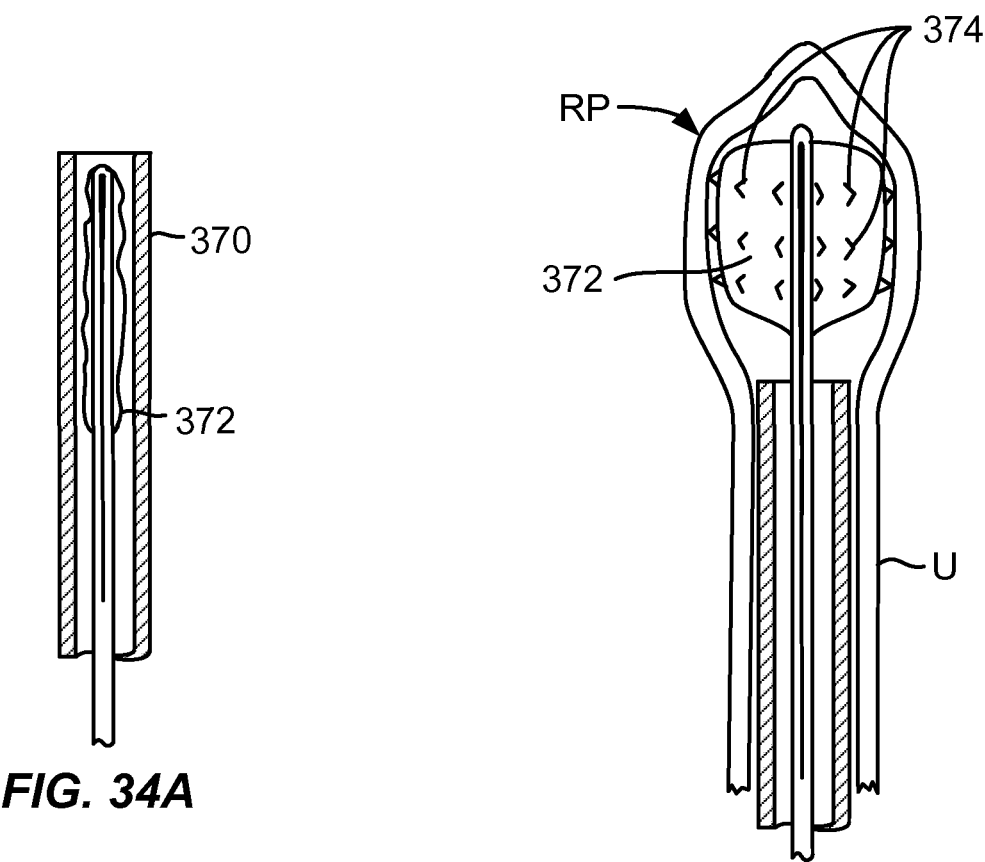
FIG. 34A
FIG. 34B

TREATMENT OF KIDNEY DISEASE BY RENAL PELVIS ABLATION

CROSS-REFERENCE TO RELATED APPLICATIONS

This application is a continuation of U.S. patent application Ser. No. 18/374,612, filed Sep. 28, 2023, which is a continuation-in-part of U.S. patent application Ser. No. 17/097,387, filed Nov. 13, 2020, which is a divisional application of U.S. patent application Ser. No. 14/616,576, filed Feb. 6, 2015, which claims the benefit of the following three provisional patent applications: 61/937,353, filed Feb. 7, 2014; 62/003,918, filed May 28, 2014; and 62/074,894, filed Nov. 4, 2014. The entire contents of each of these applications are incorporated herein by reference. This application also claims the benefit of U.S. Patent Application No. 63/410,840, filed Sep. 28, 2022.

BACKGROUND

Chronic kidney disease typically results in a gradual loss of kidney function. Healthy kidneys filter waste and excess fluids from your blood, which are then removed in your urine. Advanced chronic kidney disease can cause dangerous levels of fluid, electrolytes and wastes to build up in your body. Chronic kidney disease can have a number of negative patient outcomes including stroke, congestive heart failure (CHF), end stage kidney disease (end stage renal failure), Treatment for chronic kidney disease focuses on slowing the progression of kidney damage, usually by controlling the cause. But even controlling the cause might not keep kidney damage from progressing. Chronic kidney disease can progress to end-stage kidney failure, which is fatal without artificial filtering (dialysis) or a kidney transplant.

SUMMARY OF ILLUSTRATIVE EMBODIMENTS

The methods and procedures described herein demonstrate that renal pelvic denervation significantly reduces blood pressure in patients with uncontrolled hypertension who were previously taking antihypertensive drugs. In one trial, by two months after the procedure there was a reduction in the 24-hour ambulatory systolic blood pressure of 20.3 mmHg with similar reductions in the daytime and nighttime measurements, indicating a continuous 24-hour blood pressure-lowering effect. Of note, 17 of the 18 patients in the study had reductions in their daytime systolic blood pressure, none had an increase in daytime systolic blood pressure and all 18 had reductions in their 24-hour systolic blood pressure.

During the study, estimated glomerular filtration rate (eGFR) was used to determine a patient's stage of kidney disease and qualify them for treatment. eGFR can be calculated from blood creatinine levels along with age, body size, and gender of the patient. GFR can be calculated in other ways as well.

Surprisingly, the study data further demonstrated a small but significant increase in eGFR and a significant decrease in mean serum creatinine, both of which correlate with a decreased risk of kidney disease and associated morbidities, including a reduced risk of stroke, congestive heart failure, and end-stage renal disease, as well as hormone function, including reductions in renin, aldosterone, and angiotensin. Equivalent observed increases in eGFR and decreases in mean serum creatinine have not generally been observed with intravascular renal nerve ablation, thus affording added therapeutic benefit for renal pelvis ablation.

An exemplary method for treating kidney disease in accordance with an embodiment comprises selecting a patient suffering or at risk of suffering from kidney disease, as indicated by a pre-treatment estimated glomerular filtration rate (eGFR) in a first range. In one embodiment, the pre-treatment eGFR range in which patients are qualified to receive the treatment is a range between 45 and 90 mL/min/1.73 $m^2$. For patients selected to receive treatment, an effector is introduced into an interior of the patient's renal pelvis comprising the patient's kidney or an upper region of a ureter adjacent to the patient's kidney. The effector is used to deliver energy to an interior wall of the renal pelvis, producing an increase in the patient's eGFR in a range from 1 to 100 mL/min/1.73 $m^2$.

In specific instances, the patient experiences an increase in eGFR in a range from 10 to 75 mL/min/1.73 $m^2$. In further specific instances, the patient experiences an increase in eGFR in a range from 10 to 50 mL/min/1.73 $m^2$, often in a range from 10 to 25 mL/min/1.73 $m^2$.

Typically, the patient had a serum creatinine level in a range from 0.95 mg/dL to 1 mg/dL prior to treatment. In specific instances, the patient experiences a decrease in serum creatinine in a range from 0.01 mg/dL to 1 mg/dL. In further specific instances, the patient experiences a decrease in serum creatinine in a range from 0.05 mg/dL to 1 mg/dL, often in a range from 0.1 mg/dL to 1 mg/dL.

In some instances, the patient may also suffer or be at risk of suffering from hypertension, but in many instances, the patient does not have diagnosed hypertension.

Some embodiments provide apparatus, systems, and methods for disrupting, inhibiting, denervating and/or modulating the activity of renal nerves present in a patient's kidney by exchanging energy or delivering active agents or substances to the renal wall or the nerves which lie within the wall of the renal pelvis or adjacent to the renal pelvis within the kidney. The energy exchange is effected through a wall of the renal pelvis using an effector which has been positioned within the interior of the renal pelvis. The renal blood vessels, including the renal arteries and to a lesser extent the renal veins, enter the kidney in a branching network from the main renal artery and main renal vein leading to the kidney. The renal nerves are present in the adventitial tissue surrounding these branching blood vessels as well as in the tissue bed adjacent to the external wall of the renal pelvis. The renal nerves are also in the wall of the renal pelvis in the form of a dense nerve matrix consisting of both afferent and efferent nerves between the muscle layers as well as within the endothelium and submucosa.

The wall of the renal pelvis is a particularly rich source for afferent sensory nerves which are found in the urothelium which lies immediately adjacent to the renal pelvis. They are also found in rich supply in the intermediate submucosal layer which is closest to the urothelium. The renal pelvis wall is also a source for efferent nerves which are found in both the intermediate and outer submucosal layers. Thus, the treatments described herein that exchange energy or deliver active agents from the renal pelvis may be particularly effective in treating the afferent sensory nerves that are presently believed to be principally responsible for the reduction of hypertension, and have now been found to also have an effect on kidney function that can be treated.

Some embodiments rely on introducing or advancing the effector into the interior of the renal pelvis by a minimally invasive approach or access. Usually, access will be through the urinary tract and thus not require percutaneous penetration (and thus may be performed as a "natural orifice surgery"). Once in the interior of the renal pelvis, the effector will be used to exchange energy and/or deliver active agents or substances to the wall of the renal pelvis and additionally to the tissue bed surrounding the exterior wall of the renal pelvis to effect nerve denervation or modulation. Often, the effector will be an expandable structure, such as an inflatable balloon or mechanically expandable cage, which can be deployed within the renal pelvis to engage at least a portion of interior wall of the renal pelvis, often engaging the entire interior wall of the renal pelvis. Elements for exchanging energy and/or delivering active substances can be present on the outer wall of such expandable structures or may be present within the interior of such expandable structures in order to generate, exchange, and deliver energy and substances as described in more detail below.

The effector may be advanced to the interior of the renal pelvis of the kidney in a variety of ways. Usually, the effector will be advanced through the urinary tract to reach the renal pelvis without the need to penetrate tissue. In such cases, the effector will be disposed on a urinary catheter, typically near a distal end of the catheter, and the urinary catheter will be advanced through the urethra, the bladder, and the ureter to reach the renal pelvis. Techniques for advancing catheters into the renal pelvis are known in the art, for example in connection with delivery of urinary stents to create drainage paths past urinary stones. Usually, an access or guide catheter and/or a guidewire will be placed through the urethra into the bladder to provide an access path through the os of the ureter at a proximal end of the bladder. A second catheter carrying the effector will then be advanced through the access or guide catheter and/or over the guidewire and then through the length of the ureter so that the effector is position within the interior of the renal pelvis. The effector will usually be expanded and then be used to exchange energy and/or deliver active substances, as described in greater detail below.

Specific devices and methods may be employed using the effector in order to denervate, modulate, or inhibit the renal nerves within the wall of the pelvis or surrounding the renal pelvis. For example, the effector may comprise electrodes, typically on an inflatable or expandable structure, and the electrodes may be used to deliver radiofrequency energy across the wall of the renal pelvis to treat the nerves within the wall of the renal pelvis and/or further into the nerves surrounding the renal pelvis to heat the tissue bed surrounding the pelvis to treat the renal nerves. The electrodes may be monopolar, in which case the "active" electrodes on the effector will be connected to one pole of a radiofrequency generator while the other pole will be connected to a dispersive electrode placed on the patient's skin, e.g., on the small of the back. Alternatively, the radiofrequency electrodes could be bipolar, where one or more electrode pairs (nominally positive and negative) are disposed on the surface of the effector in order to deliver a more localized and higher current density to the tissue surrounding the renal pelvis to treat the nerves within the wall of the renal pelvis and/or further into the nerves surrounding the renal pelvis.

In a second aspect, some embodiments include apparatus and systems for inhibiting, modulating, or destroying function of renal nerves in a patient's kidney. Apparatus comprise a catheter adapted to be introduced into an interior of the kidney, typically the renal pelvis, and an effector on the catheter to exchange energy and/or deliver an active substance from the interior of the kidney through a wall of the renal pelvis into the nerves within the wall of the renal pelvis surrounding the renal blood vessels in the kidney. The effector will typically comprise an expandable member which can be expanded within the renal pelvis to engage an interior wall of the renal pelvis, for example, comprising a compliant balloon or mechanically expandable cage adapted to inflate/expand to occupy all or a substantial portion of the interior volume of the renal pelvis. The compliant balloon or other expandable structure can thus serve to position elements of the effector against the interior wall of the renal pelvis and/or to locate an internal mechanism within the effector in a predetermined position/geometry relative to the wall and nerves of the renal pelvis. Usually, the effector will be adapted to limit the exchange of energy and/or the delivery of active substances into regions of the kidney beyond the renal pelvis, such as the papillae, the pyramids, the parenchyma, and other sensitive structures of the kidney which could be damaged by the protocols herein and adversely impact kidney function. While the inflatable body or other portions of the effector could engage such sensitive structures, the effector will be designed so that energy exchange and/or active substance delivery avoid such sensitive structures, for example by placing external elements on the effector away from such sensitive structures.

In one specific aspect, a method for inhibiting or modulating the function of renal nerves in a patient's kidney comprises introducing an effector into an interior of the kidney or an upper region of an adjacent ureter. Energy is exchanged and/or active substances are delivered from the interior of the kidney to ablate a layer of tissue lining at least a portion of the renal pelvis to disrupt renal nerves within the tissue lining of the renal pelvis. The tissue lining comprises a urothelium, a lamina propria, and two muscle layers, and ablation occurs primarily within the urothelium and the lamina propria. In some instances, the ablation may extend into a connective tissue and vascular layer that surrounds the lamina propria. Typically, the ablation extends to a depth in the range from 0.1 mm to 2 mm, preferably from 0.2 mm to 1.5 mm, and more preferably from 0.5 mm to 1.2 mm. In specific embodiments, electrical energy is delivered uniformly over a continuous region of the renal pelvis at a power in the range from 50 W to 200 W.

In another specific aspect, apparatus, systems, and methods for disrupting, inhibiting, denervating and/or modulating the activity of renal nerves present in a patient's kidney deliver specific patterns of energy through the renal pelvis wall and to the renal nerves which lie within the wall of the renal pelvis or adjacent to the renal pelvis within the kidney. In particular, some embodiments include an insulated electrode structure comprising a helical, preferably spiral, electrode deployment structure, typically a pre-shaped wire, which carries rounded, ovoid, or spherical electrodes for engaging and delivering electrical energy to tissue of or near the renal pelvis or other luminal and cavity-like body structures.

Such devices are particularly advantageous as they may be easily positioned by a steerable or other sheath to position the balls or other point electrodes in the center of the renal pelvis, or any other desired location. Since the sheath and the device are not locked together, the device can be rotated relative to the sheath. This allows the sheath to maintain its curve while the helix is rotated for better positioning.

Preferably, the diameter of the balls is significantly larger than an outside diameter (OD) of the insulation on the supporting wire. An exemplary design has a ratio of 3.4:1 (0.078 in to 0.023 in) which allows the tissue to conform around the electrodes, ensuring that the electrodes will have a large contact surface area and excellent tissue contact. The geometry also helps guarantee a larger electrode-to-tissue contact force. The larger contact surface area, improved electrode/tissue contact, and larger electrode/tissue contact force are all desirable for safe, proper, and efficient energy delivery and lesion geometry. The helical/spiral shape of the device will cause the balls to press against the walls of the renal pelvis. The spacing of the balls and the helical shape creates discrete lesions in the renal pelvis on different tissue planes. This ensures that there is enough healthy tissue left intact so that the pelvis and ureter do not stricture significantly.

Some embodiments provide a method for inhibiting or modulating the function of renal nerves in a patient's kidney comprising introducing an effector into an interior of the kidney or an upper region of an adjacent ureter. Energy is exchanged or active substances delivered from effector in the interior of the kidney to ablate a layer of tissue lining at least a portion of the renal pelvis to disrupt renal nerves within the tissue lining and optionally muscle layers of the renal pelvis. The layer typically includes the urothelium and the lamina propria. While the ablation occurs primarily within the urothelium and the lamina propria, in some instances ablation can extends into connective tissue and a vascular layer that surrounds the lamina propria and muscle layers.

The depth of ablation is controlled to achieve a desired ablation with minimal damage to the kidney and kidney function. Typically, the ablation extends to a depth in the range from 0.1 mm to 2 mm, usually from 0.2 mm to 1.5 mm, and often from 0.5 mm to 1.2 mm. Such ablation depth can be achieved by delivering electrical energy, typically radiofrequency current, over a continuous region of the renal pelvis at a power in the range from 1 W to 200 W.

Introducing the effector may comprise advancing the effector through the urinary tract to the renal pelvis. For example, the effector may be disposed on a urinary catheter, and the urinary catheter may be advanced through the urethra, bladder, and ureter to reach the renal pelvis. Alternatively, introducing the effector may comprise advancing the effector percutaneously to the renal pelvis.

Energy may be delivered in a variety of ways. For example, the effector may comprise electrodes and the energy may comprise radiofrequency energy which is delivered to heat the wall of the renal pelvis and renal nerves embedded in the tissue bed surrounding the renal blood vessels. Alternatively, the effector may comprise an antenna and the energy may comprise microwave energy which is delivered to heat the wall of the renal pelvis and renal nerves embedded in the tissue bed surrounding the renal blood vessels. Further alternatively, the effector may comprise an ultrasound transducer and the energy may comprise ultrasound energy which is delivered to heat the wall of the renal pelvis and renal nerves embedded in the tissue bed surrounding the renal blood vessels. As a specific example of ultrasound energy, the ultrasound transducer may comprise a high intensity focused ultrasound transducer array. Other energy effectors may comprise a convective heat source which delivers heat through the renal pelvis to heat the wall of the renal pelvis and renal nerves embedded in the tissue bed surrounding the renal blood vessels. A specific example of a convective heat source would deliver a heated fluid within an inflated chamber deployed within the renal pelvis. Conversely, the effector may comprise a convective cooling source where heat is extracted through the renal pelvis to cool the wall of the renal pelvis and renal nerves embedded in the tissue bed surrounding the renal blood vessels. An exemplary convective cooling source comprises a cooled fluid deployed within an inflated chamber within the renal pelvis. Still other effectors may comprise a radiation-emitting source, either a radioisotope or an X-ray or other electronic radiation. Other examples include effectors having tissue-penetrating electrodes which are penetrated into a wall of the renal pelvis while energy is delivered to the wall through the electrodes. In yet other examples, the energy exchanged is mechanical energy such as abrasion or cutting.

In some embodiments, an electrode structure comprises a self-expanding deployment wire having a distal region configured to expand into and engage a wall of a renal pelvis. A plurality of rounded electrode members is distributed over said distal region where each rounded electrode member has a surface which extends radially outwardly beyond the surface of the adjacent wire.

The distal region of the deployment wire typically has a three-dimensional expanded geometry, such as a helical or spiral distal geometry or may have a two-dimensional geometry, such as a looped distal end. Even loop structures, however, may have secondary structures, such a bending or local coiling, to impart a third dimension to a planar geometry. Typically, at least the distal region of the deployment wire is electrically insulated over its surface between the rounded electrodes. The diameter of the rounded electrode structure may be from two-fold to six-fold greater than that of the deployment wire, and exemplary electrode will have a deployment wire diameter in the range from 0.1 mm to 0.7 mm and a rounded electrode member diameter in the range from 0.25 mm to 2.5 mm. In specific embodiments, the rounded electrodes are ball electrodes.

The electrode structures are frequently incorporated in an electrode deployment assembly which comprises the electrode structure as above with a delivery tube having a central passage. The electrode structure is reciprocally received the central passage of the delivery, wherein the distal region of the deployment wire is radially constrained when present in the passage and radially expanded when advanced distally out of the passage. The electrode structure is usually free to rotate in the passage of the delivery tube.

In some embodiments, a method for delivering energy to a renal pelvis comprises introducing a wire into the ureter adjacent to or within the renal pelvis. The wire has a pre-shaped distal region configured to conform to the renal pelvis. The distal portion of the wire is advanced into the renal pelvis, wherein the distal portion is radially constrained while being advanced, and the distal region of the wire is released from constraint within the renal pelvis to engage tissue over a wall of the renal pelvis. Energy is applied to the wall of the renal pelvis through a plurality of electrodes on the wire, wherein the electrodes have rounded surfaces (typically being ball electrodes) which extend beyond the surface of the adjacent wire and which embed into the renal pelvis wall.

In exemplary embodiments, a vacuum may be applied within the renal pelvis while applying energy to draw the walls of the renal pelvis against the rounded electrodes. The pre-shaped distal region of the wire may have a helical, spiral, looped or other two-dimensional or three-dimensional distal geometry. At least the pre-shaped distal region of the wire will usually be electrically insulated over its surface between the electrodes, and the diameter of the electrodes will usually be from two-fold to six-fold greater than that of the wire. In specific embodiments, the wire has a diameter in the range set forth above and the electrodes have a diameter in the range set forth above. In an exemplary protocol, the distal portion of the wire is advanced into the renal pelvis from a central passage of a delivery tube which had been positioned in the renal pelvis, wherein the distal region is radially constrained when present in the passage and radially expanded when advanced distally out of the passage.

The foregoing general description of the illustrative implementations and the following detailed description thereof are merely exemplary aspects of the teachings of this disclosure and are not restrictive.

BRIEF DESCRIPTION OF THE DRAWINGS

The accompanying drawings, which are incorporated in and constitute a part of the specification, illustrate one or more embodiments and, together with the description, explain these embodiments. Where applicable, some or all features may not be illustrated to assist in the description of underlying features. In the drawings:

FIGS. 9A and 9B illustrate an alternative device configured to ablate one or more tissue layers of the renal pelvic wall.

FIGS. 27A-27C show ball electrodes attached to superelastic alloy wire inside a catheter tube and subsequently deployed in a renal pelvis.

FIGS. 34A-34C show a drug delivery balloon with microspikes both inside a sheath and deployed in the renal pelvis.

DETAILED DESCRIPTION OF ILLUSTRATIVE EMBODIMENTS

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

It is noted that, as used in the specification and the appended claims, the singular forms "a," "an," and "the"

include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

Figure 1:
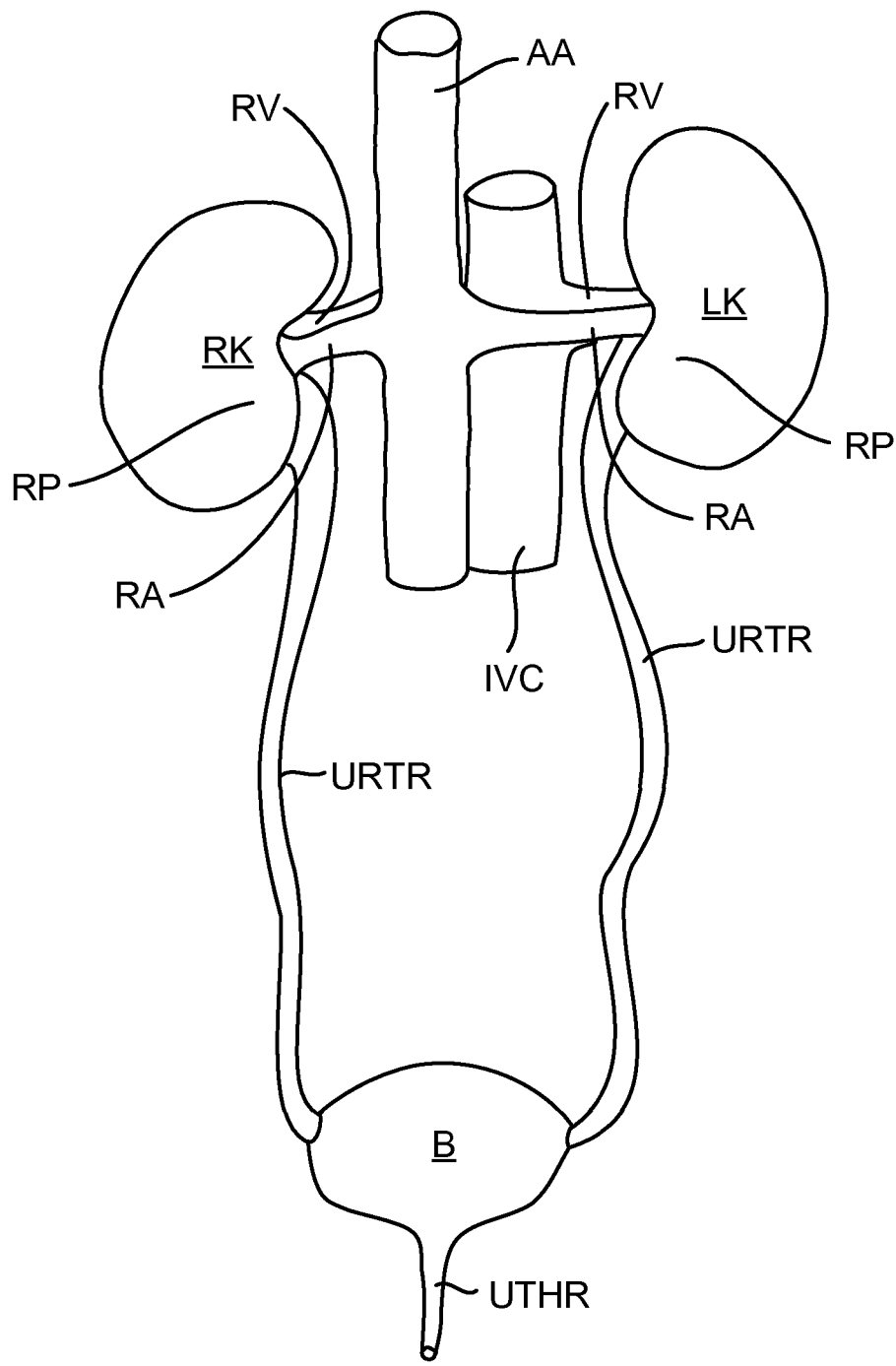
FIG. 1 is a diagrammatic illustration of a patient's urinary system.

A patient's urinary tract is diagrammatically illustrated in FIG. 1. The urinary tract includes the bladder B, which receives urine from the right and left kidneys RK and LK and drains the urine through the urethra UTHR. The kidneys each receive oxygenated blood through the renal artery RA from the abdominal aorta AA and blood from the kidneys is returned through the renal vein RV to the inferior vena cava IVC. Of particular interest to the present disclosure, the urine which is processed in the kidney is received in an interior cavity of each kidney referred to as the renal pelvis RP which acts as a funnel and delivers the urine into the top of the ureter URTR. Methods and protocols described herein will be performed within the interior of the renal pelvis RP in order to treat the renal nerves within the walls of the renal pelvis as well as the nerves surrounding the renal arteries within the adventitia and adipose tissue and to a lesser extent surrounding the renal veins which branch from the main renal artery and renal vein within the tissue of the kidney.

Figure 2B:
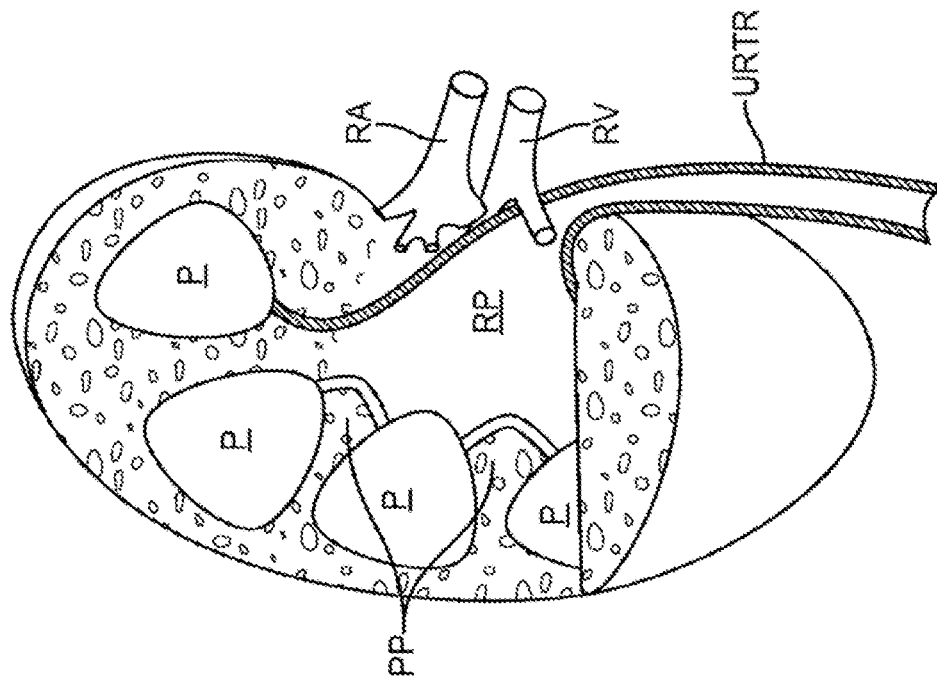
FIGS. 2A and 2B are partially broken-away illustrations of a patient's kidney showing the renal pelvis and other structures.
Figure 2A:
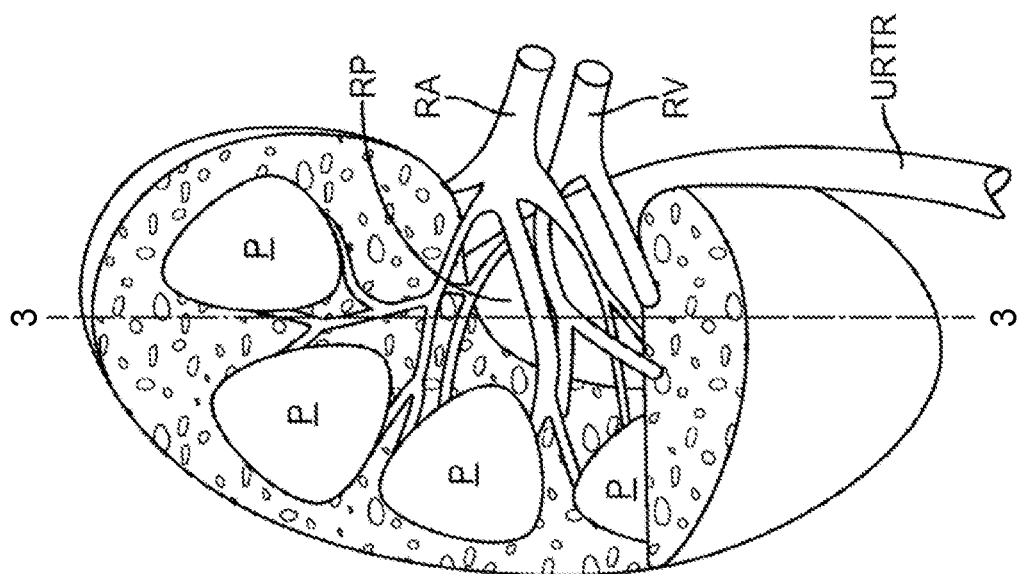

Referring now to FIGS. 2A and 2B, the right kidney RK is shown in section to expose the renal pelvis RP and other internal structures of the kidney. As shown in FIG. 2A, the renal pelvis is a funnel-shaped extension of the upper end of the ureter URTR and is surrounded by the branching portions of the renal artery RA and the renal vein RV, both of which branching structures extend into the body of the kidney and surround the pyramids P and other structures, including the papillae PP. The branching structures of the renal artery RA and renal vein RV as well as the anterior wall of the renal pelvis are removed in FIG. 2B to show the interior of the renal pelvis which is the target location for the therapies of several embodiments.

Figure 3:
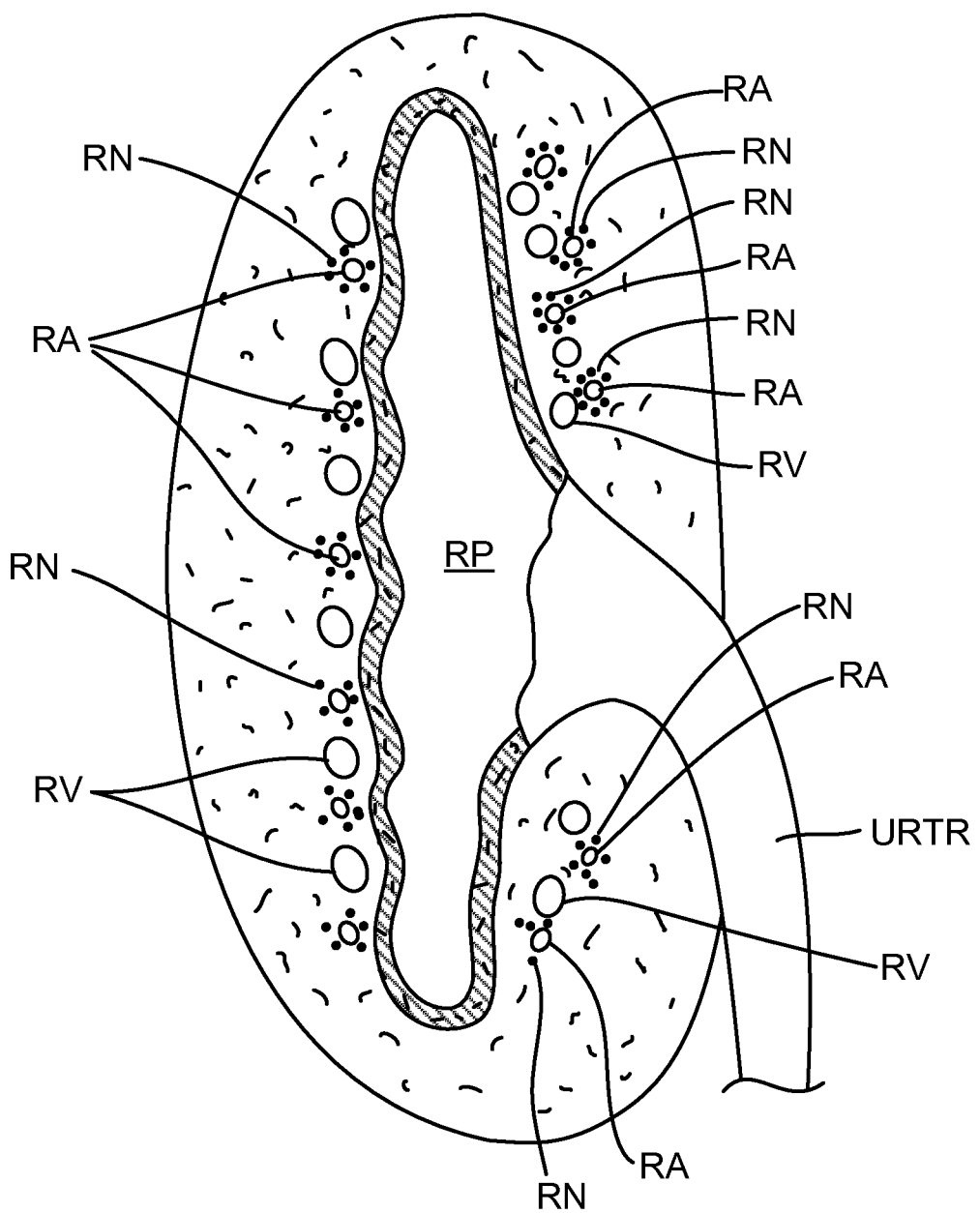
FIG. 3 is a cross-sectional view of the patient's kidney taken along line 3-3 of FIG. 2A.
Figure 3A:
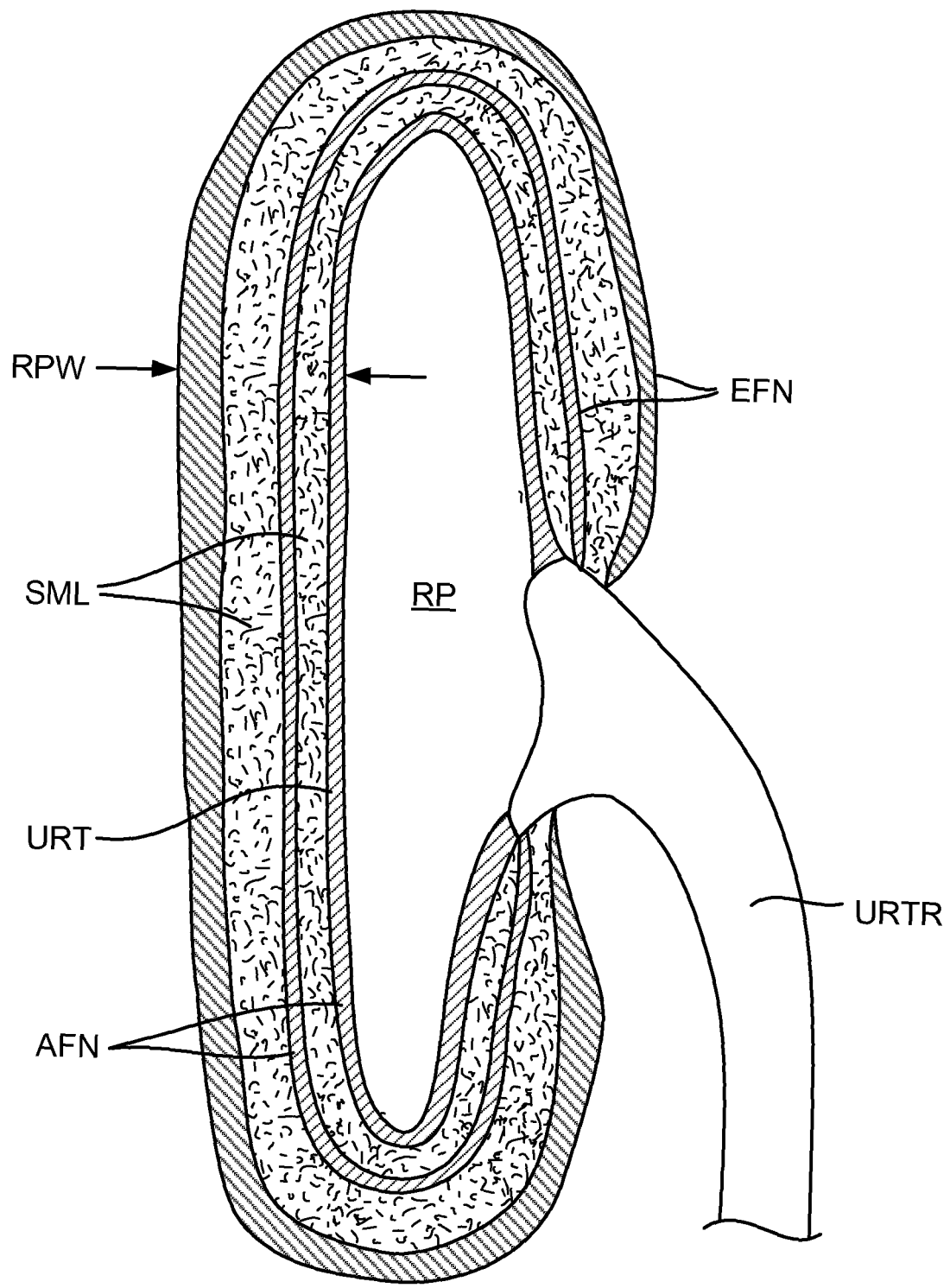
FIG. 3A shows the structure and location of renal nerves within the muscle layers, endothelium, and submucosa of the renal pelvis. The afferent nerves originate and are mostly contained within the wall of the renal pelvis. They have a direct effect on the efferent sympathetic nerves and are responsible for sympathetic muscle tone and vasoconstriction.

As further shown in FIG. 3, which is a cross-sectional view taken along line 3-3 of FIG. 2A, the renal nerves RN surround the renal blood vessels, particularly the renal arteries RA, extending adjacent to and surrounding the outer wall of the renal pelvis RP in a tissue bed surrounding the renal pelvis. As shown in FIG. 3A, the renal nerves follow the arteries and then divide. A portion of the divided nerves enter the renal pelvic wall RPW where they intertwine with the afferent nerves AFN that are located within the smooth muscle layers, endothelium and submucosa SML of the renal pelvis. The afferent nerves AFN originate and are mostly contained within an interior wall of the renal pelvis adjacent to the urothelium URT. The afferent nerves have a direct effect on the efferent sympathetic nerves EFN (which are generally located nearer the exterior surface of the renal pelvis wall RPW than are the afferent sensory nerves AFN) and are responsible for sympathetic muscle tone and vasoconstriction. It is the renal nerves shown in FIGS. 3 and 3A, and in particular the sensory afferent nerves AFN, which are typically but not exclusively the target structures to be treated by the methods and apparatus of several embodiments.

Figure 4A:
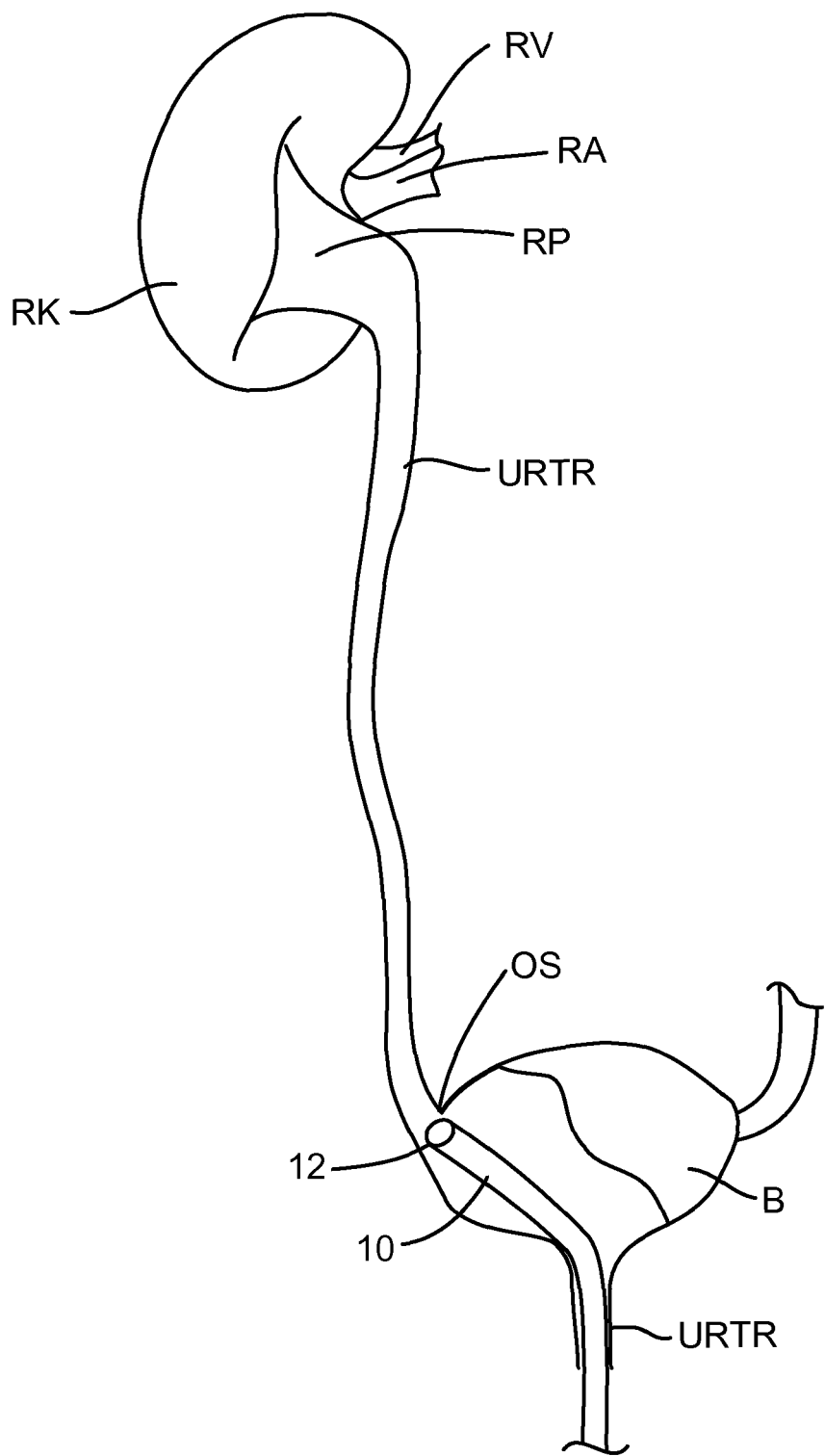
FIGS. 4A through 4C illustrate access and treatment of a patient's renal pelvis according to the principles of an embodiment.
Figure 4B:
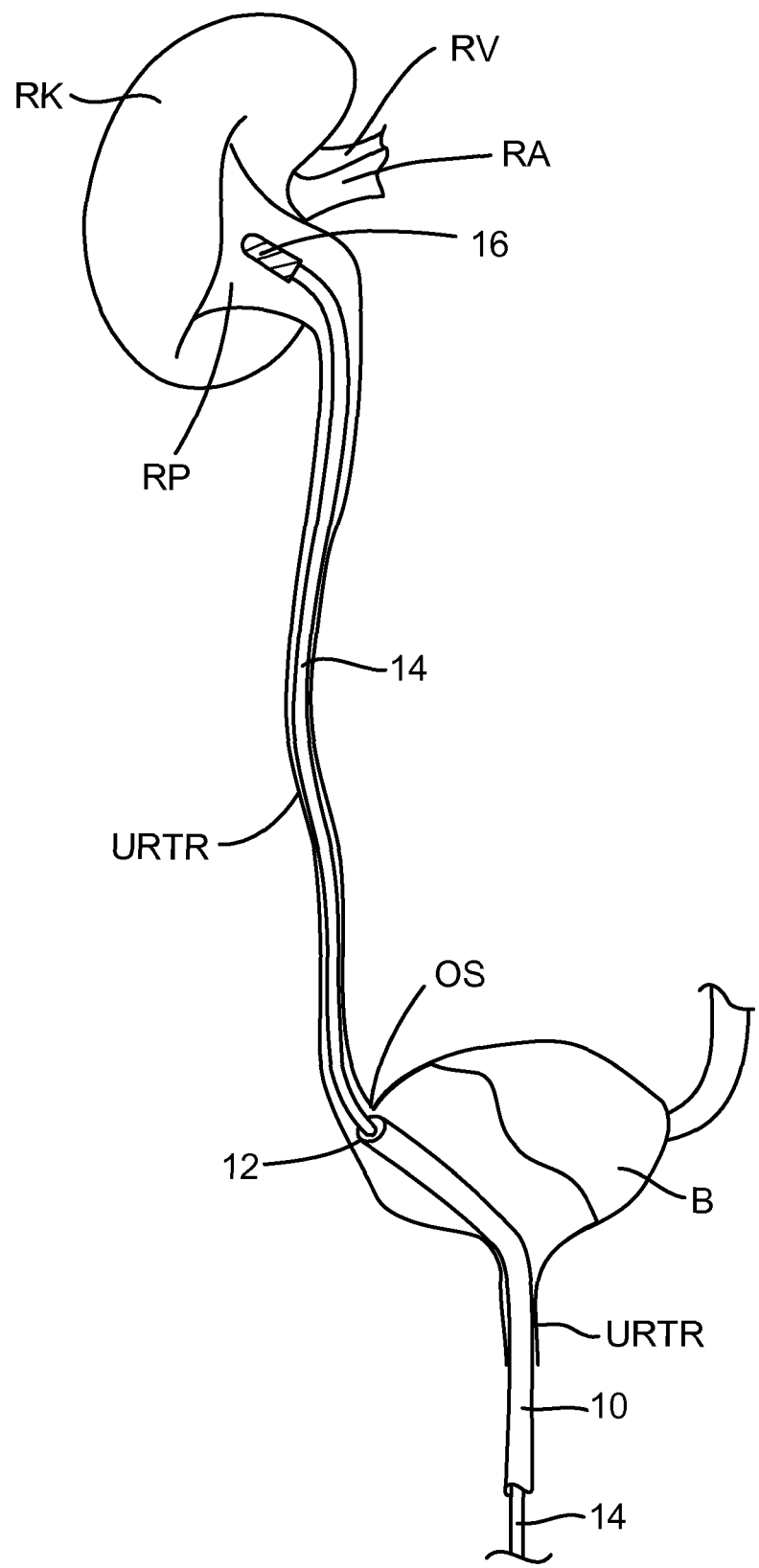
Figure 4C:
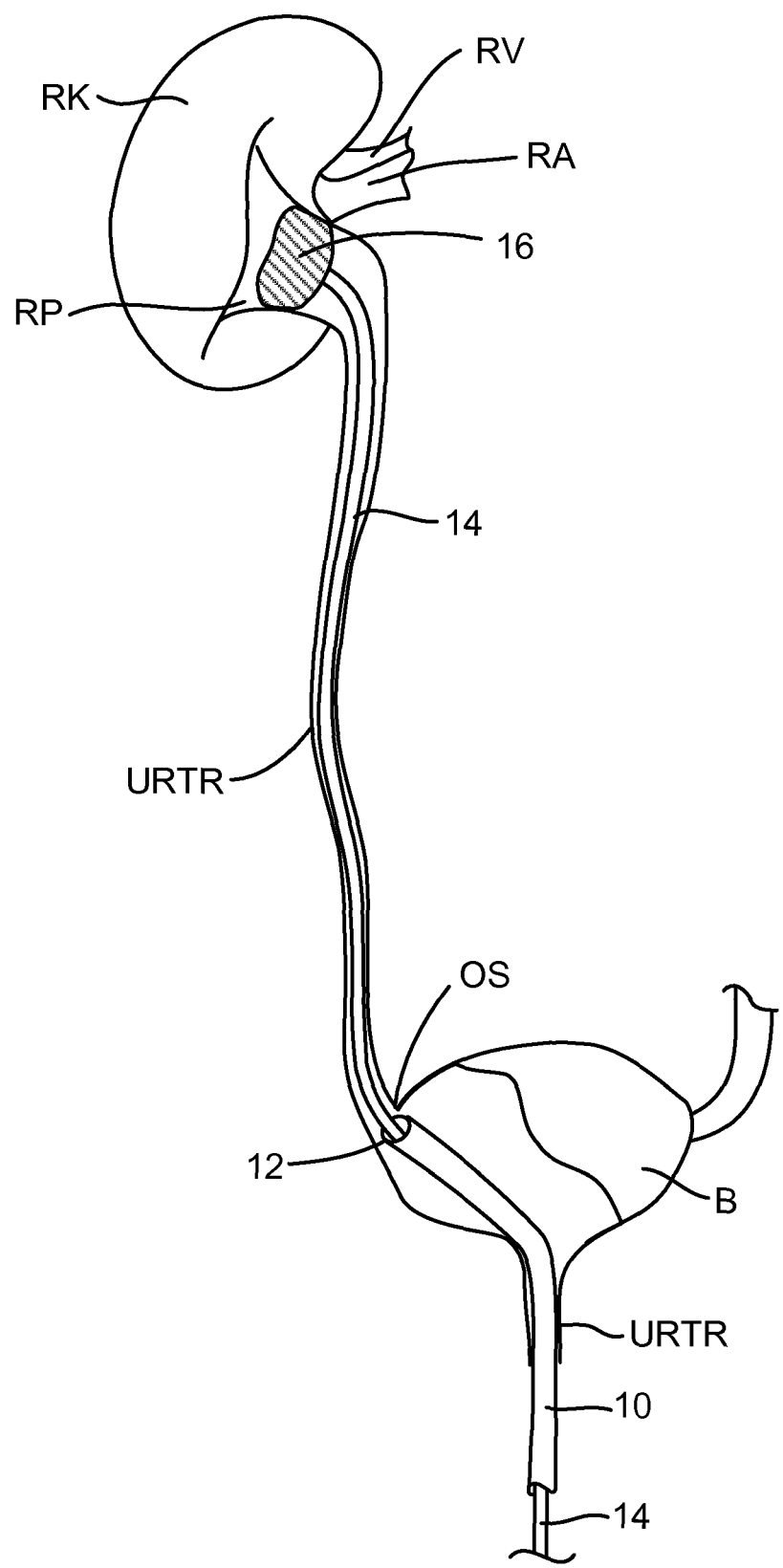

Referring now to FIGS. 4A through 4C, a first exemplary protocol for accessing and treating the renal nerves in the kidney will be described. Initially, a guide or other tubular catheter 10 is advanced through the urethra UTHR to position a distal port 12 adjacent the os OS at the lower end of the ureter URTR.

As shown in FIG. 4B, a treatment catheter 14 is then advanced through the guide catheter 10 (optionally over a guidewire), out of port 12, and into a lumen of the ureter URTR. An effector 16 at the distal end of the treatment catheter 14 is advanced into the renal pelvis RP, optionally under fluoroscopic and/or ultrasound guidance in a conventional manner.

Once in the renal pelvis RP, the effector 16 will be deployed in order to treat the renal nerves in accordance with the principles of the present disclosure. For example, the effector may comprise an expandable structure which is mechanically expanded or inflated within the renal pelvis to engage the interior walls of the pelvis as shown in FIG. 4C. Any one of a variety of energy exchange devices or substance delivery devices may then be employed to exchange energy or deliver the substances through the wall of the renal pelvis to treat the nerves embedded within the walls.

Figure 5:
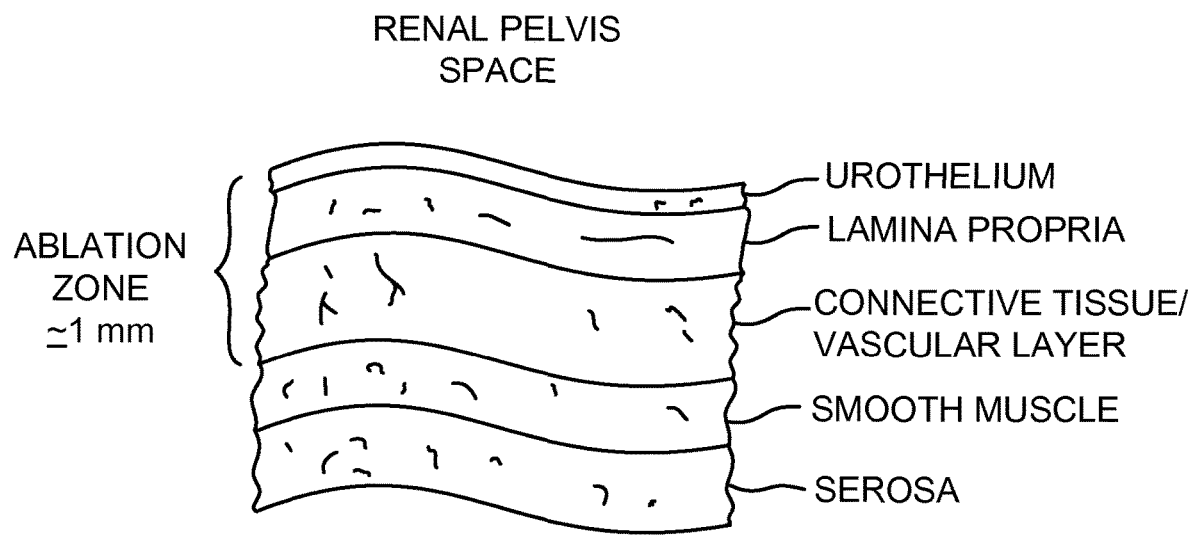
FIG. 5 illustrates the tissue layers of the renal pelvic wall.

In some instances, devices and methods will be configured to ablate a thin layer of tissue which lines the renal pelvis. The renal pelvic wall consists of multiple tissue layers as shown in FIG. 5. Afferent and efferent nerves exist through the layers, and there is a high concentration of afferent nerves close to the surface (e.g., within the urothelium, lamina propria, and extending into a first muscle layer). Together, the urothelium and lamina propria layers will be referred to as the "tissue lining the renal pelvis." The inventors herein have determined that moderate to extensive damage to the muscle layers may cause stenosis of the renal pelvis, which is of course undesirable. The inventors herein have further determined that the creation of very shallow lesions on the interior wall of the renal pelvis will target the surface afferent nerves (thus achieving renal denervation), while leaving the surrounding tissue (muscle, blood vessels, etc.) intact.

This result can be achieved with any number of devices, including those described in commonly owned U.S. Patent Publication 2013/0178824, the full disclosure of which is incorporated herein by reference, as well as a number of other devices described below. Energy or substance delivery through the devices must be carefully controlled to achieve the desired effect. Exemplary protocols will apply RF energy at high power (e.g., 50-200 Watts) and short application times (e.g., 0.1-15 seconds). In other instances, however, it may be possible to achieve similar ablation using low power (e.g., 1-50 Watts) and longer times (e.g., 60-300 seconds). Lesion depth should be between 0.1 mm and 2 mm, usually between 0.2 mm and 1.5 mm, and often between 0.5 mm and 1.2 mm. FIG. 5 shows the ablation zone depth.

Surface lesions having the desired depths can be created by regulating temperature, time, power, and/or impedance. More specifically, the lesion depth can be controlled by applying a specified power until a specified impedance is reached. Alternatively, the lesion depth can be controlled by maintaining a specified temperature for a specified length of time. Under any control algorithm, time, power, temperature, and impedance can be monitored for safety limits.

Figure 6:
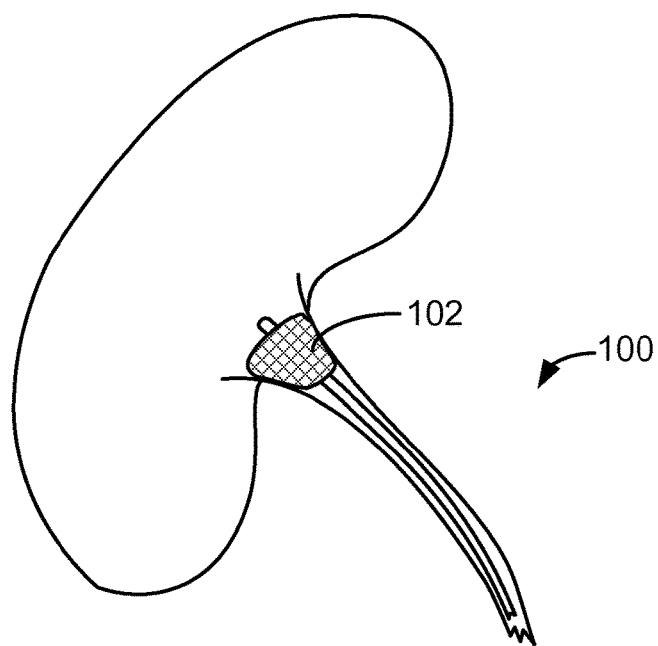
FIG. 6 illustrates a device configured to ablate one or more tissue layers of the renal pelvic wall.
Figure 7:
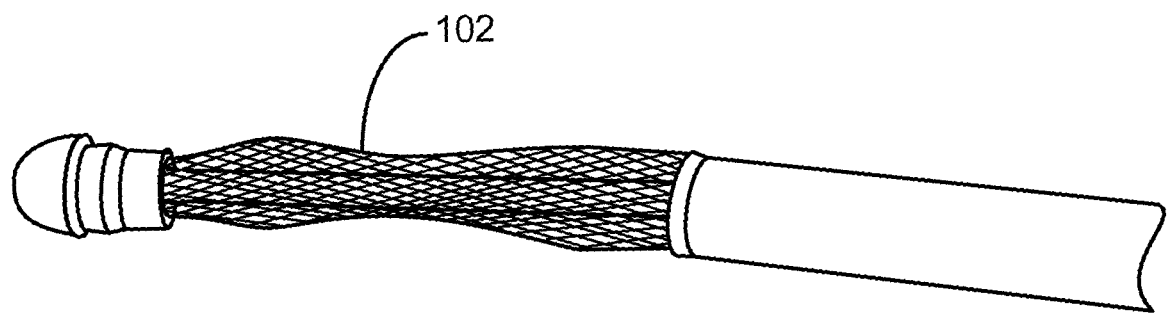
FIGS. 7 and 8 show a mesh electrode of the device of FIG. 6 in its collapsed and expanded configurations, respectively.
Figure 8:
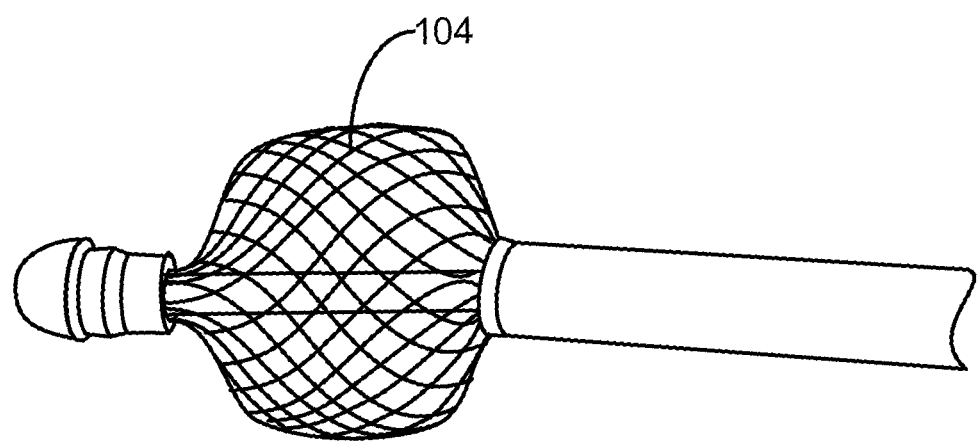

An exemplary device 100 for delivering RF power to the renal pelvis is shown in FIGS. 6-8. The device includes tubular Nitinol® mesh electrode 102 that is expanded at the target site in the renal pelvis, as shown in FIG. 6. Monopolar energy is delivered through all wires of the expanded mesh to create the desired lesion. The diameter of the device is typically 7 Fr-11 Fr in the collapsed state (FIG. 7). The diameter of the mesh is typically 8 mm-20 mm in the expanded state (FIG. 8). The length of the mesh electrode is usually 8-20 mm in the expanded state. Use of a mesh electrode is desirable as it readily conforms to the shape of the renal pelvis.

In other embodiments, the electrodes on the delivery catheter may comprise balloons with conductors formed over their external surfaces, e.g., by conductive inks or conductive wire.

In a further exemplary device 110, an expandable flex circuit 112 can be located over a balloon 114 or other inflatable/radially expandable structure, as shown in FIGS. 9A and 9B. In this design, the flex circuit is initially rolled over the balloon (FIG. 9A), and balloon is inflated to expand and unroll the flex circuit (FIG. 9B) so that electrode(s) 116 and optionally thermocouple(s) (not shown) formed on the exterior surface of the flex circuit contact the renal pelvic wall tissue when the flex circuit is expanded. As an alternative to a rolled-up flex circuit, the flex circuit could have other expandable geometries, such as pleated, patterned (similar to an arterial stent), or the like, so that it is able to expand from a low diameter delivery configuration to a larger diameter deployed configuration. Flex circuit dimensions are typically 7 Fr-11 Fr in the collapsed state (FIG. 9A) and 8-20 mm diameter and 8-20 mm length in the expanded state (FIG. 9B). These designs can be monopolar or bipolar, the latter being useful in limiting surface lesion depth.

Another approach to creating effective renal denervation lesions without damaging renal pelvic function is to create deeper lesions only in specific areas. This will leave healthy tissue intact, avoiding strictures in the renal pelvis. Multiple devices are disclosed below to achieve this effect.

Figure 10A:
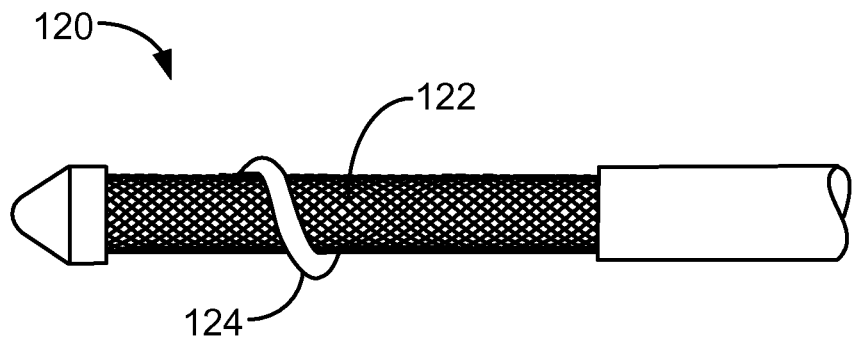
FIGS. 10A-10C illustrate devices configured to create deeper lesions in the renal pelvic wall.
Figure 10B:
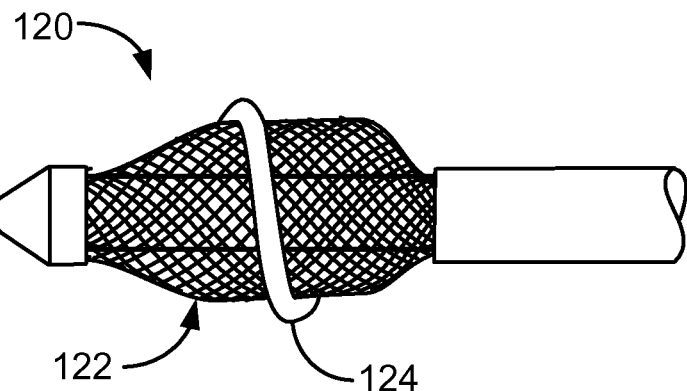
Figure 10C:
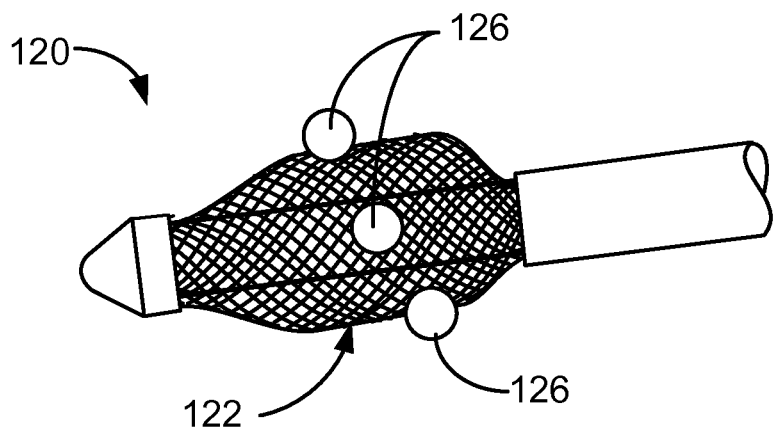

As shown in FIGS. 10A-10C, a device 120 carries a non-conductive, tubular mesh 122 that is configured to be expanded and contracted. A helical conductive wire 124 or other conductor is carried over or woven into the non-conductive mesh. For example, the conductive wire may be a stainless-steel braid, but in other instances, the conductive wire can be mono- or multi-filament. Delivery of RF or other electrical energy through the helical conductor 124 will create a helical lesion on the renal pelvis. A helical lesion helps ensure that cross-sectional areas will contain only one unique area of tissue damage around the radius. The diameter of the mesh is 7 Fr-11 Fr in the collapsed state (FIG. 10A) and is 8 mm-20 mm in the expanded state (FIG. 10B). The length of the mesh is 8 mm-20 mm in the expanded state. If the conductive wire is a monofilament, the diameter can be from 0.1 mm to 0.5 mm. If the conductive wire is a braided cable or a braided tube, the diameter can be from 0.1 mm to 0.25 mm. A thermocouple may be secured to the conductive wire or to the non-conductive mesh in proximity to the conductive wire for temperature control. Alternatively, lesions can be created with impedance control only.

In a similar embodiment shown in FIG. 10C, conductive contact pads 126 (e.g., metallic balls) are applied to the conductive wire at specific intervals to enhance tissue contact and create non-continuous lesion patterns. The conductive wire is insulated between the contact pads so that only the contact pads conduct energy to the tissue.

Figure 11A:
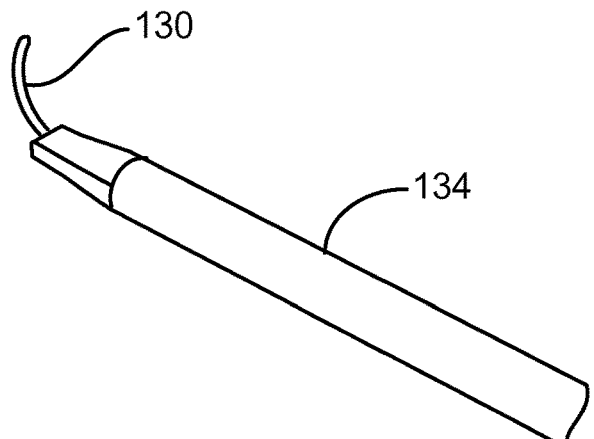
FIGS. 11A-11C illustrate alternative devices configured to create deeper lesions in the renal pelvic wall.
Figure 11B:
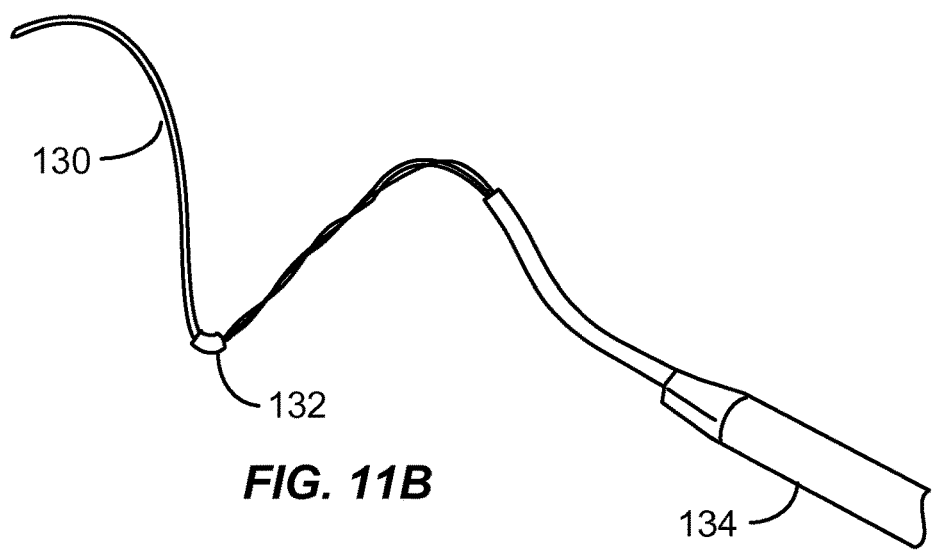
Figure 11C:
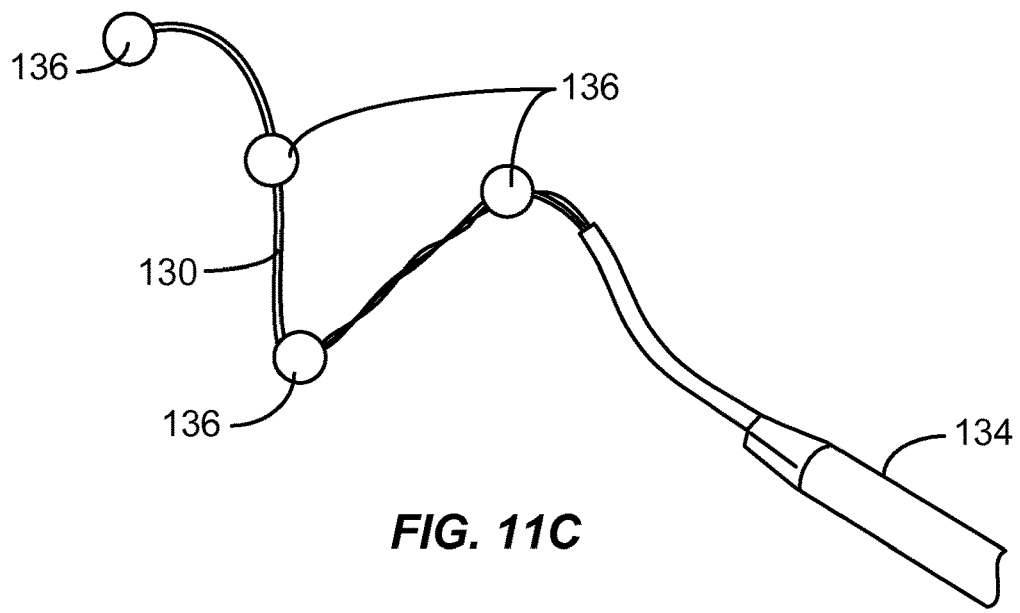

In another embodiment (FIGS. 11A-11C), a straight Nitinol® or other superelastic wire 130 or other conductor is heat set into a helical shape at its distal end. An introducer catheter 134 carries the wire and is configured to be advanced to the renal pelvis, typically through the ureter. The wire 130 is then advanced from the lumen of the catheter. As it exits the catheter, the wire 130 assumes a pre-set helical shape. Application of RF through this wire will create a helical lesion in the renal pelvis. A thermocouple 132 may be secured to the wire for temperature measurement. The diameter of the catheter is 7 Fr-11 Fr. The diameter of the helix wire is 8 mm-20 mm in the free-state. The length of the helix is 8 mm-20 mm in the free-state. The diameter of the Nitinol® wire is in the ranges set forth above. In the embodiment of FIGS. 11A-B, the helical wire is insulated at certain intervals to create a non-continuous, helical lesion pattern. In the embodiment of FIG. 11C, conductive contact pads 136 (e.g., metallic balls) are attached to the helical wire at specific intervals to enhance tissue contact and create non-continuous lesion patterns. The wire is insulated between the contact pads so that only the contact pads conduct energy to the tissue. Thermocouples are secured inside or proximate to one or more of the contact pads for temperature measurement. The diameter of the contact ball electrodes is in the ranges set forth above.

In another embodiment (FIGS. 12A-12C), a Nitinol® or other superelastic wire 140 or conductor is heat set into a helical shape. The wire is connected to the distal tip of an inner shaft 142 and the distal tip of an outer shaft 146. The inner shaft 142 fits and slides within a lumen of the outer shaft 146. When the inner shaft is extended, the wire collapses. When the inner shaft is retracted, the wire opens up into a helical shape. Application of RF through this wire will create a helical lesion in the renal pelvis. A thermocouple (not shown) may be secured to the wire for temperature measurement. The diameter of the outer shaft is 7 Fr-11 Fr. The diameter of the helix wire is 8 mm-20 mm in the expanded state (FIG. 12B). The length of the helix is 8 mm-20 mm in the expanded state. The diameter of the Nitinol® wire is 0.004 in to 0.025 in.

Figure 12A:
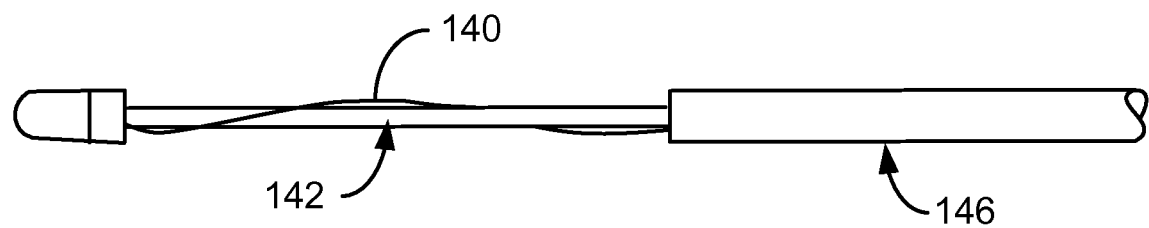
FIGS. 12A-12C illustrate a further alternative device configured to create deeper lesions in the renal pelvic wall.
Figure 12B:
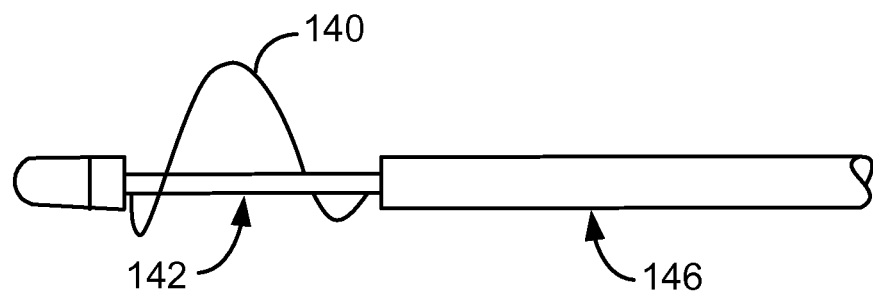
Figure 12C:
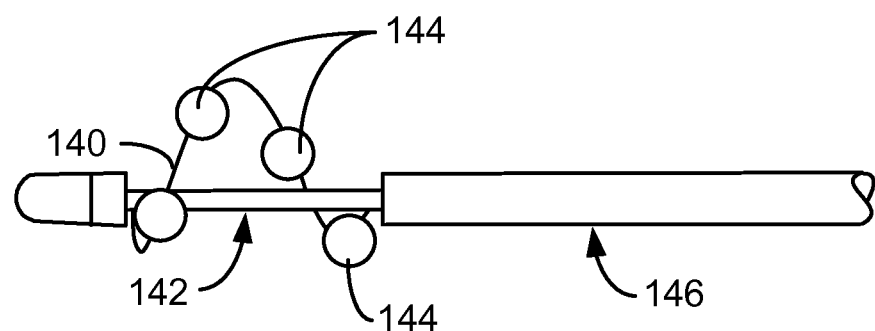

In the embodiment of FIGS. 12A and 12B, the helical wire is typically insulated at certain intervals to create a non-continuous, helical lesion pattern. In the embodiment of FIG. 12C, conductive contact pads 144 (e.g., metallic balls) are applied to the helical wire at specific intervals to enhance tissue contact and create non-continuous lesion patterns. The wire is insulated between the contact pads so that only the contact pads conduct energy to the tissue. Thermocouples are secured inside or proximate to one or more of the contact pads for temperature measurement. The diameter of the contact balls is 0.03 in-0.10 in.

Figure 13:
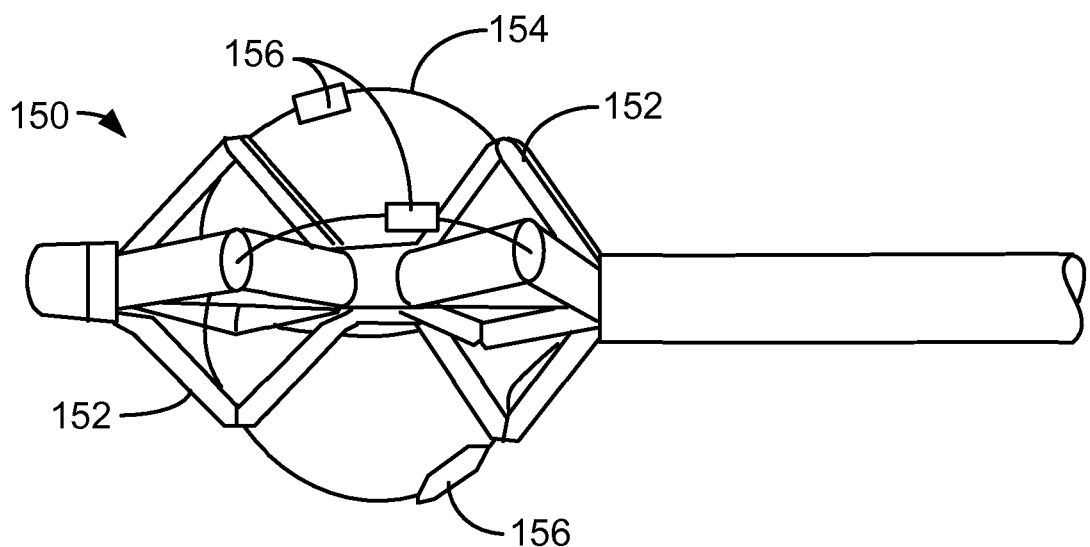
FIG. 13 illustrates a device where the wires carried by malecots have contact pads arranged in a helical pattern.

The device 150 of FIG. 13 includes two malecot supports 152. Wires 154 connect each of the eight ridges or peaks of the malecots, and each of the four wires is insulated except where a larger metallic contact pad 156 is secured. The contact pads are positioned so as to create a helical lesion pattern. Thermocouple(s) (not shown) may be placed on or proximate to one or more of the contact pads for temperature measurement. Wire diameter is 0.004 in to 0.01 5 in. Length and diameter of the malecots when expanded are typically from 8 mm-15 mm.

Figure 14A:
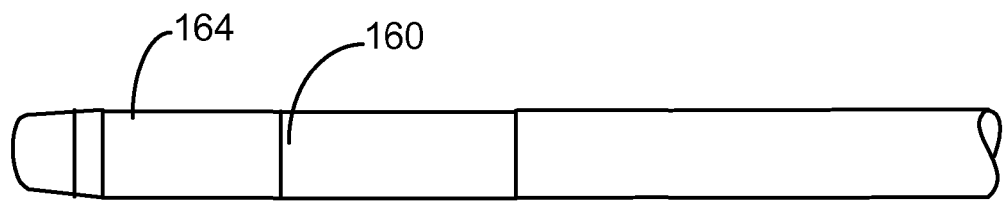
FIGS. 14A and 14B illustrate further alternative devices with deployable tine electrodes arranged in a helical pattern.
Figure 14B:
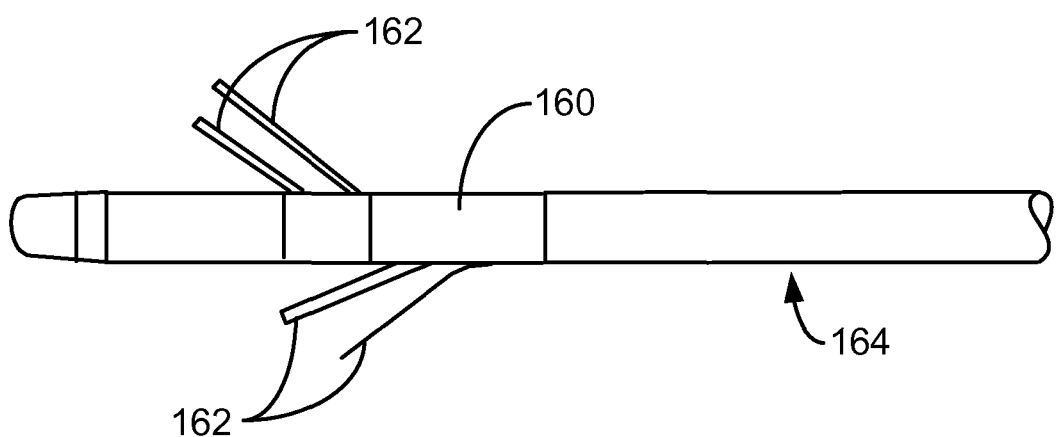

In another embodiment as illustrated in FIGS. 14A and 14B, a Nitinol® or other superelastic tube 160 is laser cut and heat set to form a plurality of outwardly biased tines 162. The tines are axially offset to create a helical pattern, and the tube 160 is electrically insulated except for the distal ends of the tines. The tube is secured to a catheter shaft (not shown), and a sheath 164 slides over the tube and catheter. As the sheath is slid distally, the tines are exposed and allowed to expand outward to contact the tissue. Application of RF energy will create discrete lesions in a helical pattern. Thermocouples (not shown) may be secured to the inside of one or more of the tines for temperature measurement. The sheath diameter is 7 Fr toll Fr. The tips of the tines expand to create a helix with a diameter of 8 mm-20 mm.

Figure 15:
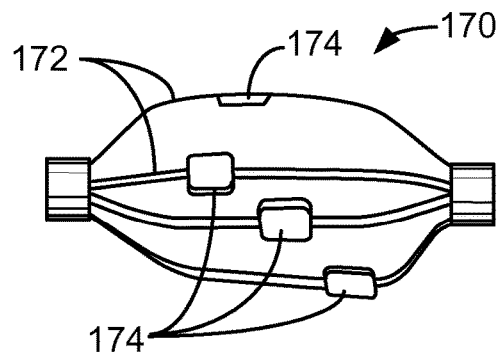
FIG. 15 illustrates another self-expanding support structure carrying a helical arrangement of electrode contact pads.
Figure 20:
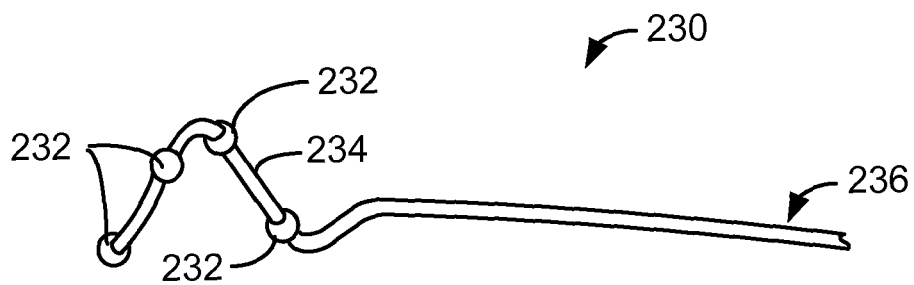
FIGS. 20-23 illustrate a renal wall ablation device similar to that of FIGS. 11A-11C.
Figure 21:
Figure 22:
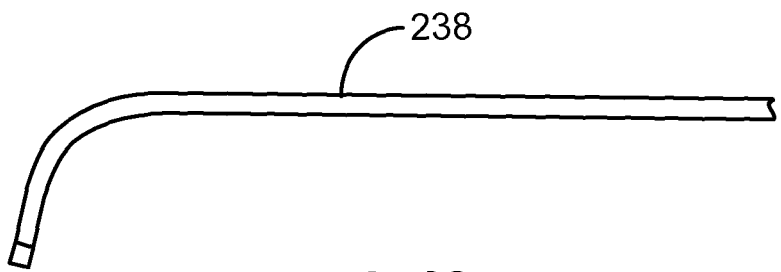
Figure 23:
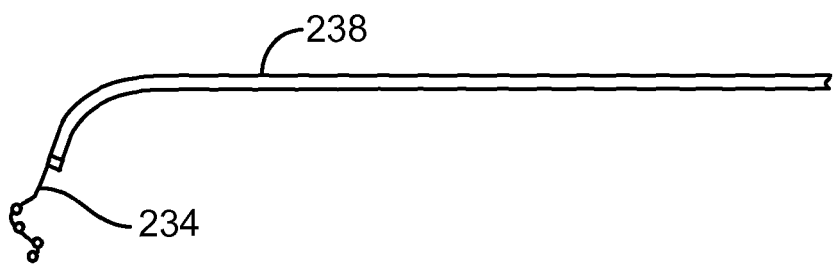

In yet another embodiment (FIG. 15), a Nitinol® or other superelastic tube is laser cut and heat set so as to create a self-expanding bulb 170 with a plurality of struts 172 which carry contact pads 174. The tube is electrically insulated, except for the contact pads. FIG. 20 shows the laser cut tube only, but the tube would be secured to a catheter shaft (similar to any of the catheter shafts shown previously) at a proximal end of the tube. A sheath is slid over the tube to contract the bulb. As the sheath is slid proximally, the bulb opens and the contact pads expand to contact the tissue. Thermocouples may be secured to the inside of one or more of the tines for temperature measurement. Application of RF energy will create discrete lesions in a helical pattern. The sheath diameter is 7 Fr to 11 Fr, and the bulb expands to a diameter of 8 mm to 20 mm.

In still other embodiments, a single ball-electrode may be disposed at the distal end of a steerable catheter and may be used to create discrete lesions one-at-a-time. The user positions the ball to contact the tissue at the appropriate spots. The electrode can be monopolar or bipolar. A thermocouple may be secured inside or proximate to the ball for temperature measurement. The ball diameter is typically 0.02 in-0.10 in.

As an alternative to targeting the nerves embedded close to the surface of the wall of the renal pelvis, it may be advantageous to target the nerves further away from the renal pelvic wall (e.g., nerves surrounding the renal arteries). The inventors herein have found that damaging the wall of the renal pelvis may be detrimental to proper function. Therefore, in these other embodiments, it would be advantageous to target nerves farther away from the renal pelvic wall, while leaving the renal pelvic wall intact. In addition, it would be advantageous to do this by accessing the renal pelvis, or anywhere along the ureter or kidney. Previously described ultrasound catheters deliver acoustic energy "to heat the wall of the renal pelvis and renal nerves embedded in the tissue bed surrounding the renal blood vessels". This achieves reaching the farther nerves. In order to lessen risk of damaging the renal pelvic wall, the present embodiment can employ "focused" ultrasound transducers (high intensity focused ultrasound or HIFU) which can directly heat tissue surrounding the target nerves with minimal heating of the pelvic wall and the tissues immediately adjacent to the pelvic wall. Thus, an ultrasonic transducer catheter can access the renal pelvis through the ureter and deliver energy to tissue beyond the renal pelvic wall while keeping the renal pelvic wall intact with minimal heating.

Catheters according to some embodiments may comprise tissue-penetrating elements in addition to the radiation-emitting elements which have been previously described. For example, the tissue-penetrating elements may comprise radio frequency electrodes, chemical delivery structures, heat delivery structures, cryogenic delivery structures, and the like.

Figure 16:
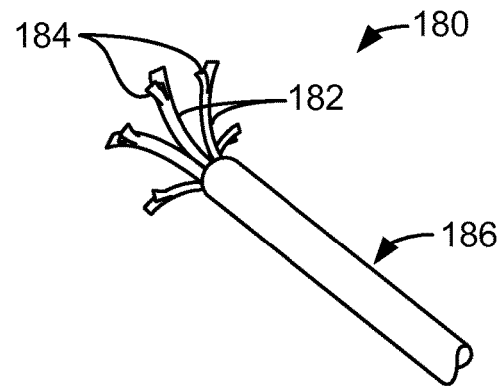
FIGS. 16-19 illustrate tools configured to mechanically disrupt nerves in the renal pelvis wall.

The renal nerve pathways may also be disrupted by mechanical means. In one embodiment, as illustrated in FIG. 16, an expandable member 180 is formed from a laser cut Nitinol® or other superelastic tube that is heat set with expandable tines 182 and bent up tabs 184 that act as cutters. A sheath 186 may be advanced to collapse the tines inside the sheath. When the sheath is retracted, the tines self-expand outwardly so that the cutters can contact the wall of the renal pelvis. The device is then rotated and/or translated axially so as to scrape the inner wall of the renal pelvis. This scraping will disrupt the nerves at the surface of the renal pelvis wall. In order to control bleeding, a balloon can be inserted into the renal pelvis after the scraping to apply pressure to the walls. The sheath size for this device is 7 Fr to 11 Fr. Various other embodiments for mechanical renal denervation can also be used including a single scraper consisting of a curved member with a sharp distal area and an expandable stent-like device with various sharp areas.

Figure 17:
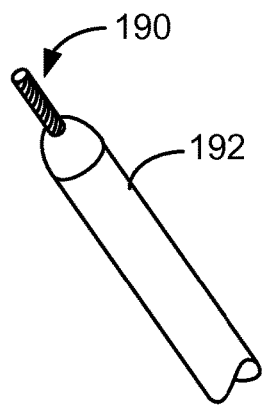

In another embodiment, as shown in FIG. 17, mechanical denervation may be done using high frequency vibration. High frequency vibration has been used in other medical devices for such purposes as tunneling and boring. In this embodiment, a tip or "effector" 190 may have various geometries, may be delivered via a catheter 192, and may be placed on the urothelium of the renal pelvis where it is driven by a generator such as a piezoelectric or other transducer to provide high (>1000 Hz) or low (<1000 Hz) frequency energy where the resulting vibration for causes scraping and/or abrading of the surface of the urothelium to disrupt nerves. The tip 190 may be retractable in the catheter 192. Such vibratory catheters will typically be sized from 7 Fr to 11 Fr. Other suitable effector geometries may include but are not limited to (1) rectangular, flat surface area, (2) helical surface area, (3) effector of curved geometry for enhanced contact with the renal pelvis, and (4) steerable effector for targeted contact with the renal pelvis.

Figure 18:
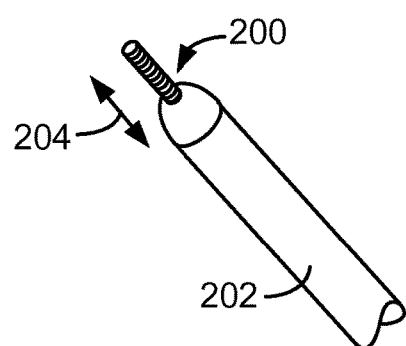

In still another embodiment as illustrated in FIG. 18, mechanical denervation may be accomplished via a reciprocating motion. A shaft 200 is reciprocated axially (the direction of arrow 204) within a larger catheter shaft 202 and can abrade the surface of the renal pelvis. An inner telescopic shaft may be knurled or of similar geometry to cause abrasion for the purpose of denervation. Such reciprocating-element catheters will typically be sized from 7 Fr to 11 Fr. Other suitable shaft geometries include but are not limited to (1) a shaft tip with curved geometry for enhanced contact with the renal pelvis, and (2) a steerable tip for targeted contact with the urothelium of the renal pelvis.

Figure 19:
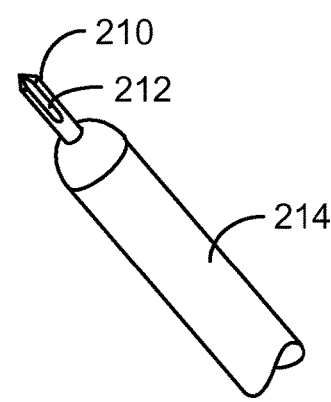

Mechanical denervation may also be accomplished using tools similar to those used for tissue biopsy, as shown in FIG. 19. Such tool would include a needle element 210 having a groove 212. The needle would reciprocate from a catheter 214 and be used to remove small amounts of the renal pelvis in strategic locations. Many biopsy devices exist for various parts of the body. This embodiment, however, would be specific to the renal pelvis and for the purposes of excising small portions of the pelvis layers in an effort to capture and disrupt renal nerves. The catheter size for this device is 7 Fr to 11 Fr. Various other biopsy geometries and elements may include but are not limited to (1) a cannulated sheath to cover the needle tip with or without circumferential rotation for the purposes of aiding tissue excising, (2) a curved geometry for enhanced contact with the renal pelvis, and (3) a steerable device for targeted contact with the renal pelvis.

Referring now to FIGS. 20-23, a device 230 for deploying helically disposed ball electrodes 232 on a pre-shaped wire 234 will be described. The wire 234 may be a superelastic Nitinol® wire having a distal end that is set into a helical or spiral shape. The plurality of metal balls 232 (four being illustrated in the drawings but anywhere from two to ten typically being useful) are attached to the wire 234 and heat shrink tubing 236 is placed over a proximal length of the wire and between the balls for insulation. A thermocouple may be attached to the most proximal ball. The Nitinol® wire diameter is typically 0.4 mm. The ball diameter is typically 12 mm. When the insulation is applied over the wire, it typically has a wall thickness of 0.1 mm and an outer diameter of typically 0.6 mm. A smaller wall thickness can be obtained by replacing the heat shrink tubing with a dielectric coating. The helical pitch is typically 12 mm. The pitch diameter (through the center of the wire) is typically 0.8 mm. The wire will be delivered through a sheath 238 which is steerable at the distal end, either being shapeable or pre-shaped. The sheath typically has an inner diameter of 2.1 mm and an outer diameter of 2.6 mm.

Figure 24:
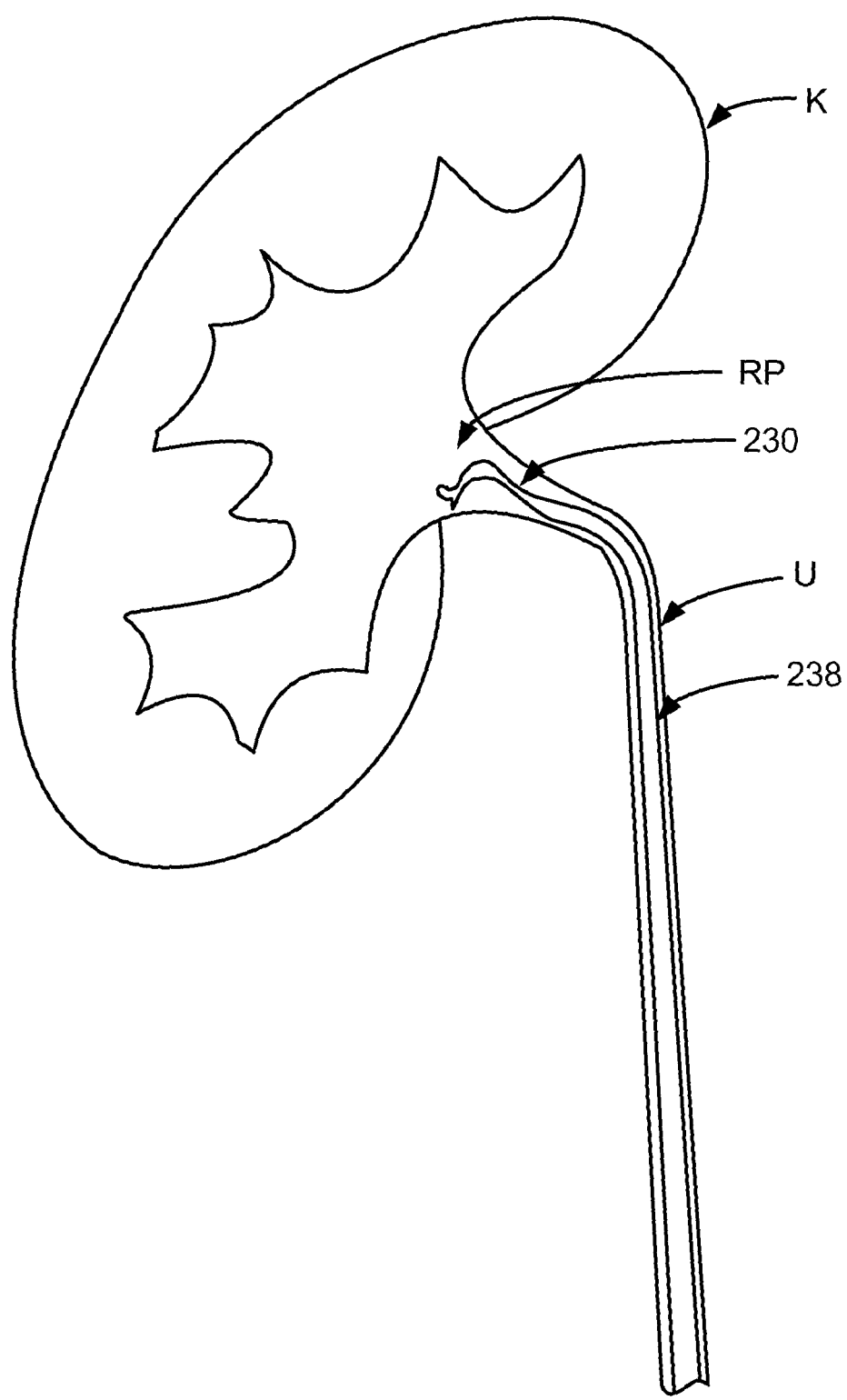
FIG. 24 illustrates use of the device of FIGS. 20-23 in ablating a renal pelvis wall.

The device 230 may be delivered to the renal pelvis RP as shown in FIG. 24. A guidewire (not shown) is first passed through the urethra, into the bladder, into the ureter U, and up to the kidney K. A dilator (not shown) is placed into the center lumen of the sheath 238. The dilator and sheath are then threaded up the guidewire into ureter and positioned so that the distal end of the sheath is just proximal of the renal pelvis. The guidewire and dilator are then removed, leaving just the sheath in place. The device 230 is then inserted through the sheath until the helical portion exits the distal end. The sheath can then be steered to position the device in the center of the renal pelvis. RF energy is then applied to the device and lesions are created at the ball/tissue interface.

In alternative configurations, each ball electrode can be independently turned on/off. A separate thermocouple can be fixed to each ball to monitor independent ball temperatures. The electrodes/wire can be stamped as shown in the Figure. These designs can be scaled down for renal denervation through the renal artery instead of through the renal pelvis.

Figure 25:
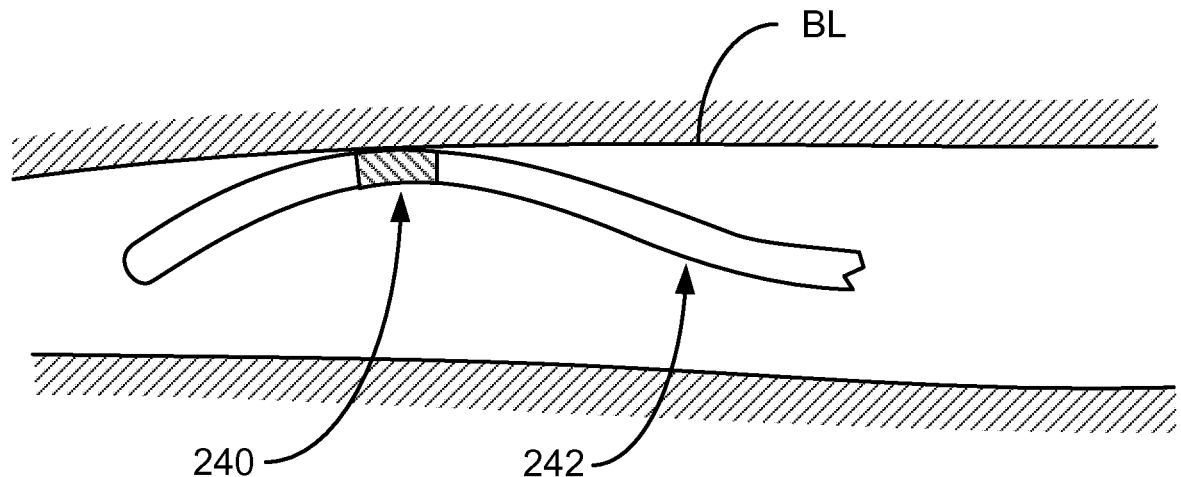
FIGS. 25 and 26 illustrate the use of a device with cylindrical electrodes and spherical electrodes for ablating a luminal wall.
Figure 26:
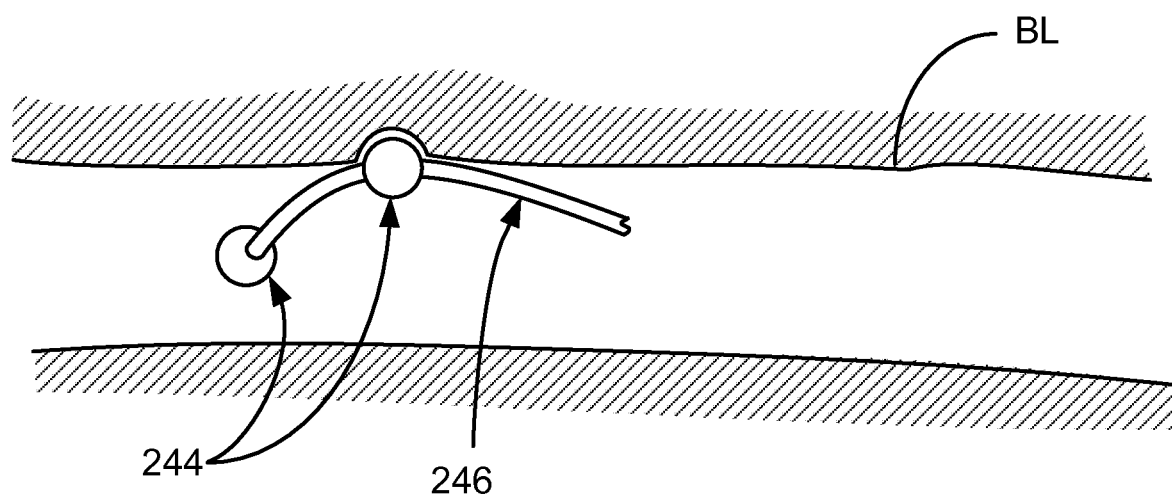

As shown in FIGS. 25 and 26, a cylindrical or "band" electrode 240 carried on a catheter or wire 242 will have only moderate contact with the wall of a body lumen BL. A relatively large ball electrode 244, however, carried on a smaller wire 246, will embed into the wall and provide a much greater surface contact area with the wall of the body lumen BL than a conventional band electrode.

As shown in FIGS. 27A-27C, a vacuum can be applied inside the ureter and/or renal pelvis to collapse the walls of the kidney. This technique can be very useful to help bring the tissue throughout the renal pelvis into intimate and conforming contact with electrodes and other mechanical effectors, as shown for example in FIG. 27C. All devices described herein can benefit from such vacuum application and kidney wall collapse, but most if not all of the devices can function with no or only a partial collapse. This vacuum-assisted approach is not intended to be applied to vascular renal denervation approaches.

As shown in FIG. 27A, an ablation device 300 comprises a Nitinol® or other superelastic nickel-titanium alloy wire 302 with ball electrodes 304 attached. When deployed through a catheter 306 into the renal pelvis RP, the wire takes on a shape similar to the pelvis. The assumed shape typically occupies a three-dimensional space within the renal pelvis to help engage or approximate balls against the tissue surface of the inner renal pelvic wall. Vacuum is applied, typically through a lumen of the catheter 306 to help embed the balls into tissue surface. RF energy is applied through the wire to the balls to create discrete lesions, damaging the renal nerves. The wire can optionally be pre-shaped in order to approximate the shape of the pyramids surrounding the renal pelvis.

Figure 28A:
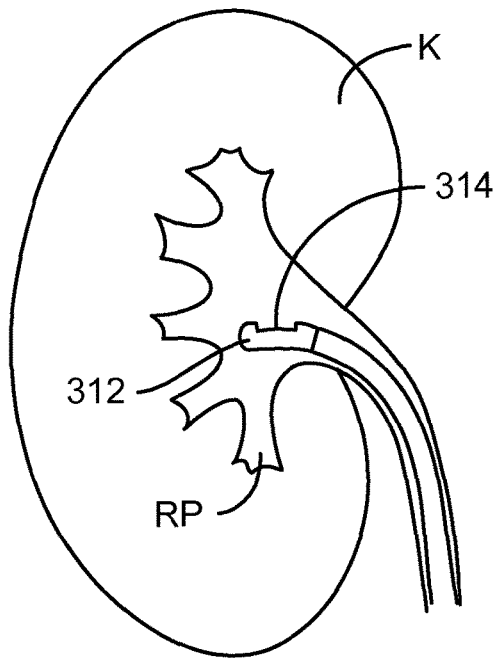
FIGS. 28A-28C show a catheter with a cutting blade inside the renal pelvis.
Figure 28B:
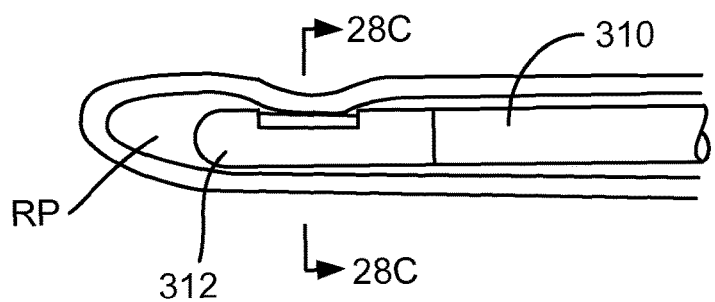
Figure 28C:
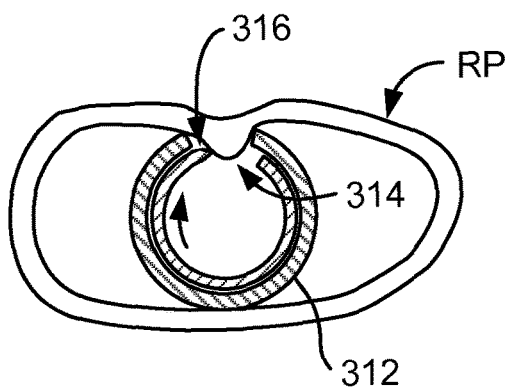

As shown in FIGS. 28A-28C, a mechanical cutter 312 is attached to a distal end of a catheter 310 having a cutting slot 314. A vacuum may be applied to draw tissue into the cutter slot 314 and a cylindrical blade 316 may be rotated to excise a small piece of tissue. Removal of renal pelvic tissue in this manner will sever renal nerves.

Figure 29A:
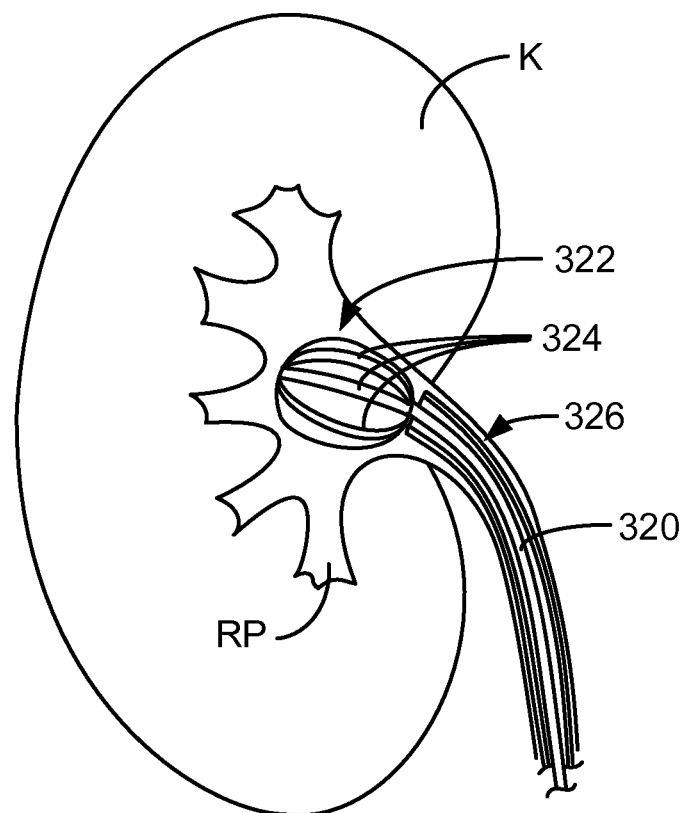
FIGS. 29A and 29B show a balloon with abrasive strips attached to the outsides deployed inside the renal pelvis.
Figure 29B:
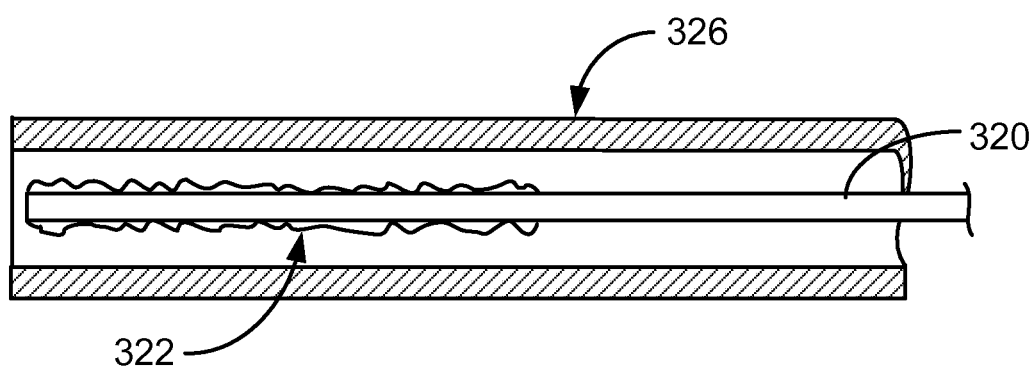

As shown in FIGS. 29A and 29B, a catheter 320 carries a distal balloon 322 having a plurality of abrasive strip 324 thereon. The balloon on the catheter may be deployed into the renal pelvis RP and, once inside the renal pelvis, a vacuum is optionally drawn and the balloon is rotated and/or translated to abrade the tissue surface. Such abrasion damages the renal nerves.

Figure 30A:
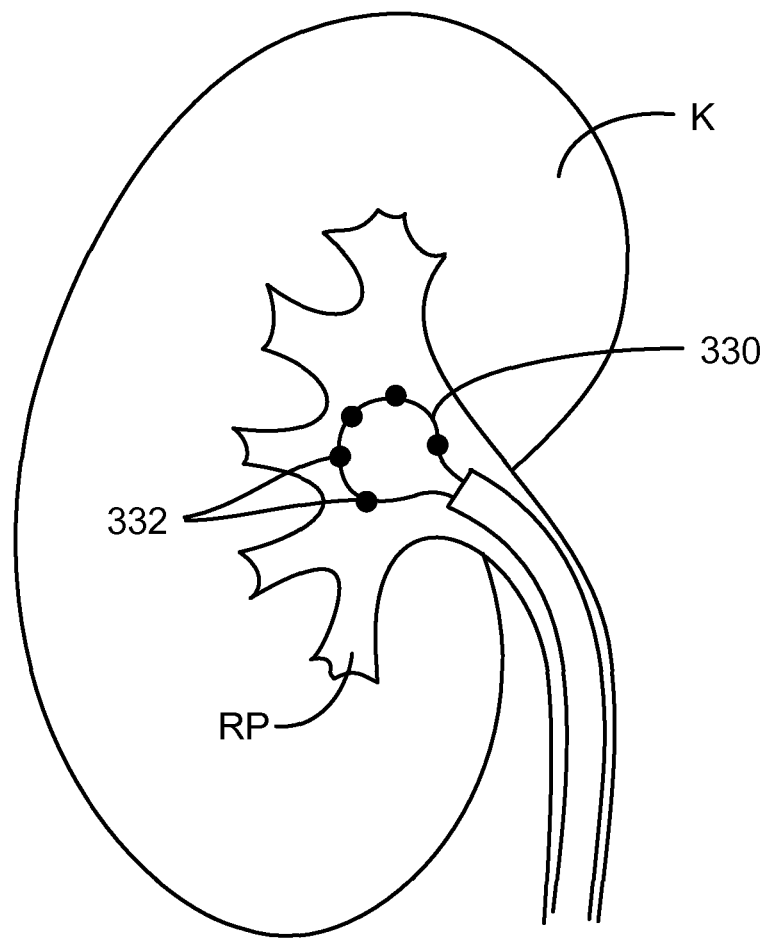
FIGS. 30A and 30B show a superelastic alloy loop wire with abrasive balls attached to the distal end.
Figure 30B:
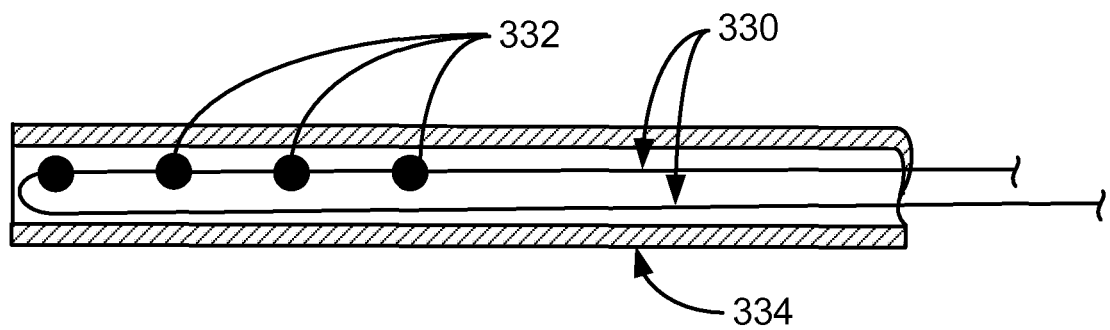

As shown in FIGS. 30A and 30B, a Nitinol® or other elastic wire 330 carries a plurality of abrasive balls 332. The wire 330 is preferably formed into a loop structure so that it expands across the renal pelvis when it is advanced from a delivery sheath or catheter 334. Once deployed, a vacuum is optionally applied, and the wire loop and balls are rotated and/or translated to abrade the tissue surface. This abrading damages the renal nerves.

Figure 31A:
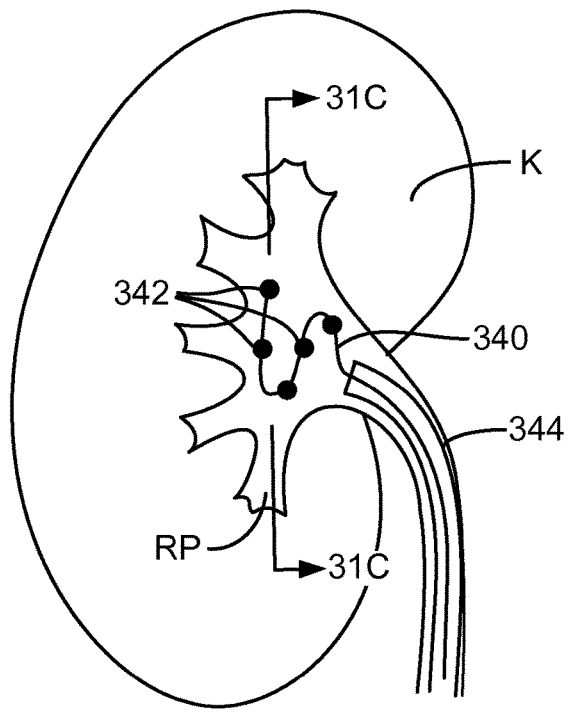
FIGS. 31A-31C show ball electrodes on a superelastic alloy wire deployed out of a sheath and into the renal pelvis where the wire takes on a serpentine shape.
Figure 31B:
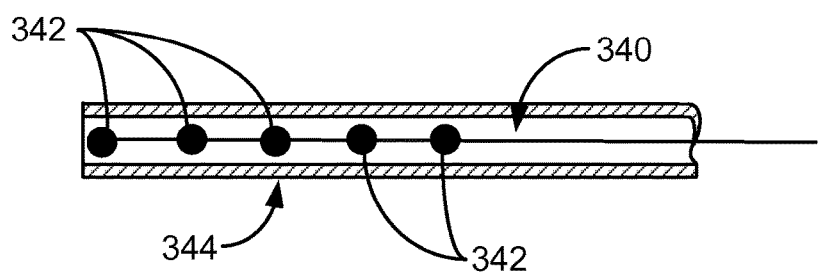
Figure 31C:
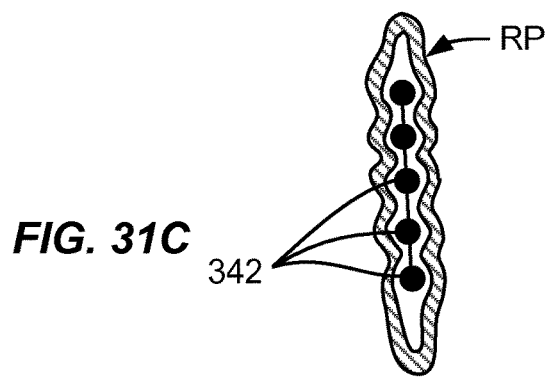

As shown in FIGS. 31A-31C, a Nitinol® or other elastic wire 340 carries a plurality of ball electrodes 342. When deployed into the renal pelvis RP, the wire 340 is pre-shaped to assume a two-dimensional serpentine shape. Vacuum is optionally applied to help embed the electrode balls into tissue surface. RF energy is applied through the wire to the balls to create discrete lesions, thus damaging the renal nerves. Alternatively, the wire shape can be pre-shaped in a circular, semi-circular, linear, spiral, or any other geometry with proximal and distal ends.

Figure 32A:
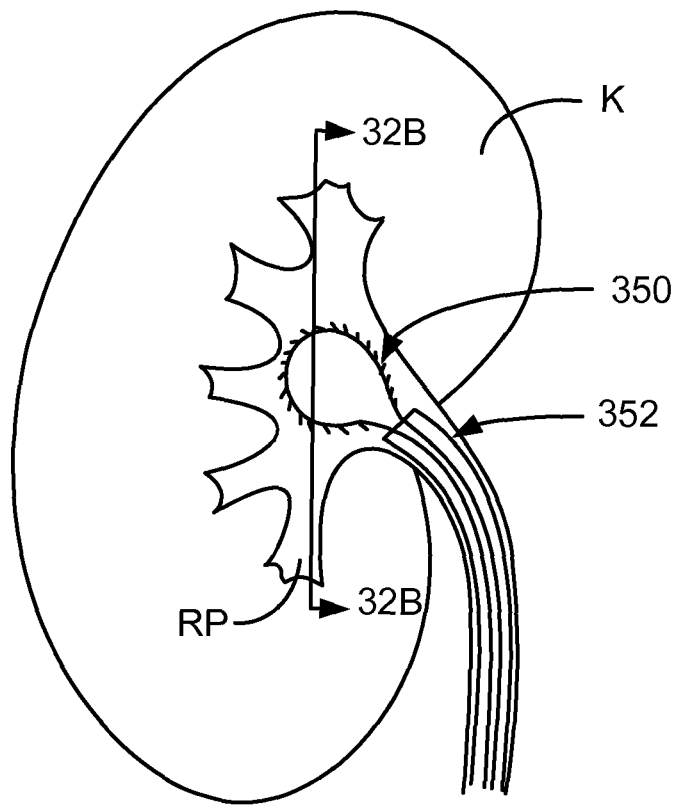
FIGS. 32A and 32B show a saw-tooth wire loop both inside a sheath and deployed in the renal pelvis.
Figure 32B:
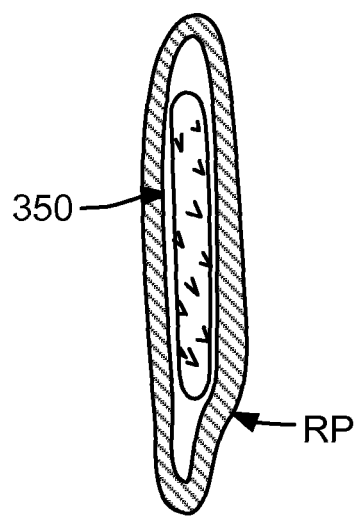

As shown in FIGS. 32A and 32B, a Nitinol® or other elastic wire 350 is formed with saw-teeth and deployed from a catheter or sheath 352 into the renal pelvis RPs. Once deployed, the saw-tooth wire can be translated and/or rotated to cut and/or abrade the tissue lining the inner wall of the renal pelvis. Applying a vacuum to the renal pelvis will help to keep the tissue in contact with the wire. This cutting/abrading damages the renal nerves.

Figure 33C:
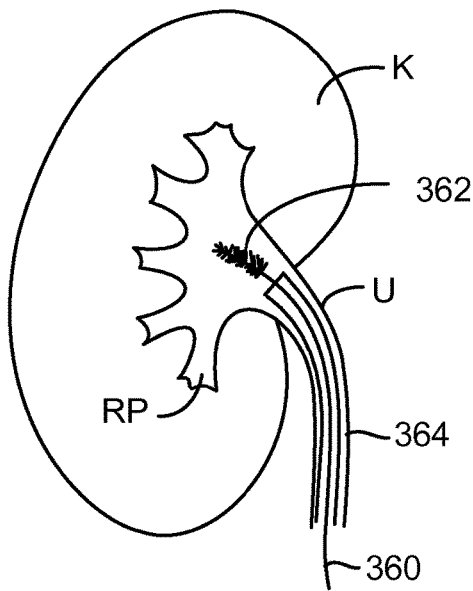
FIGS. 33A-33D show a wire brush and balloon tamponade both inside a sheath and deployed in the renal pelvis.
Figure 33A:
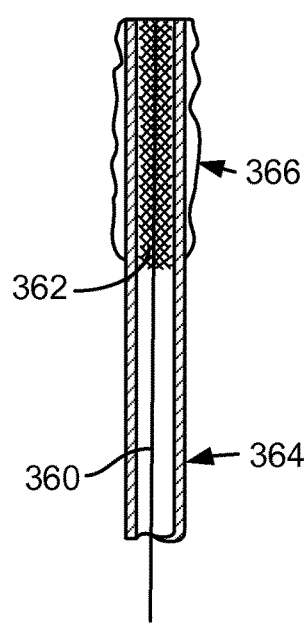
Figure 33B:
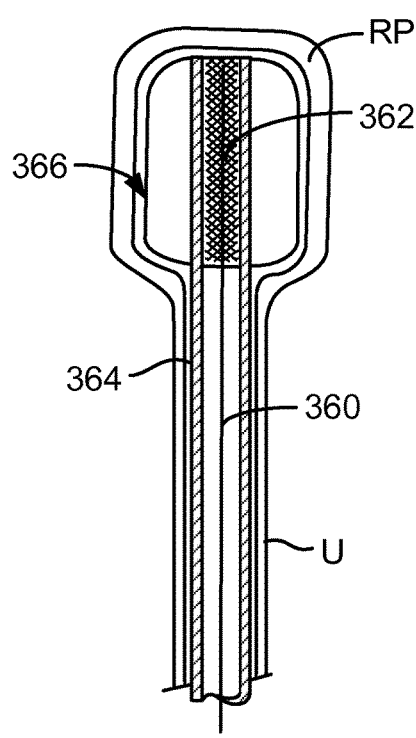
Figure 33D:
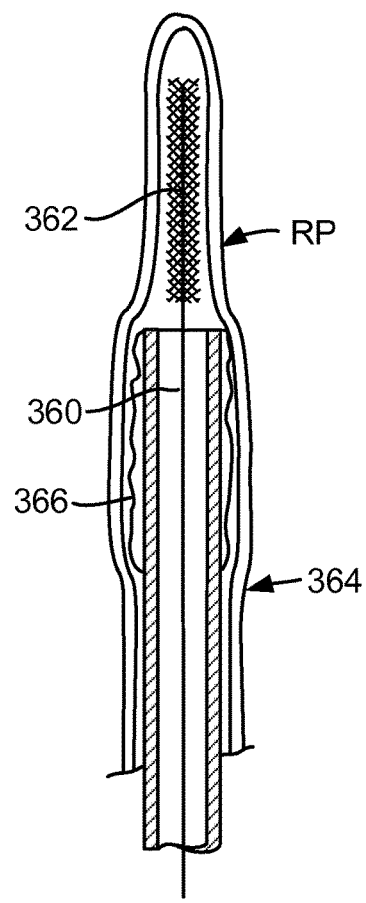

As shown in FIGS. 33A-33D, a Nitinol® or other elastic wire 360 carries a wire brush 362 which in turn is carried within a lumen of a catheter 364 having a distal balloon 366. The brush 362 is deployed from the ureter U into the renal pelvis RP, as shown in FIGS. 33B and 33C. The brush is then rotated and/or translated to abrade the tissue surface. A vacuum can be applied to help keep the tissue in contact with the brush. This abrading damages the renal nerves. After abrading, the brush is returned to the inside of the catheter. The balloon is then deployed inside the renal pelvis (FIG. 33D) to act as a tamponade and stop bleeding from the abraded tissue. The balloon may optionally have electrodes or other current delivery elements to apply electrocautery.

As shown in FIGS. 34A-34C, a catheter 370 carries a distal balloon 372 having a plurality of micro-spikes 374 thereon. The balloon on the catheter may be deployed into the renal pelvis RP and, once inside the renal pelvis, a vacuum may be drawn and the balloon will be inflated and rotated and/or translated to abrade the tissue surface. Such abrasion damages the renal nerves. The micro-spikes may optionally be hollow to deliver therapeutic or other agents to the wall of the renal pelvis either before, during, or after the abrasion. An exemplary agent is ethanol which will deactivate the nerves.

Figure 35A:
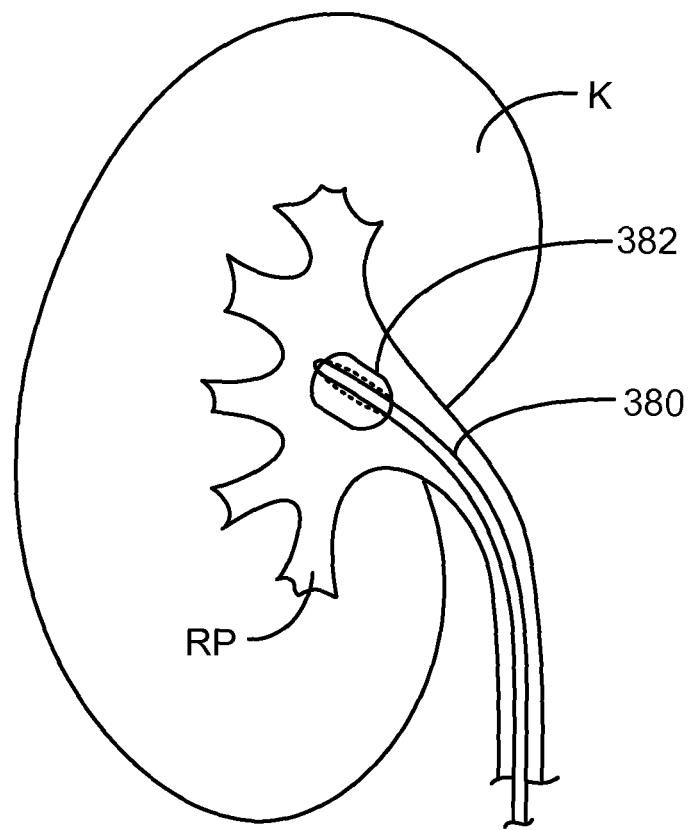
FIGS. 35A and 35B show a drug delivery balloon with openings on top and bottom sides to direct drug delivery to specific tissue areas.
Figure 35B:
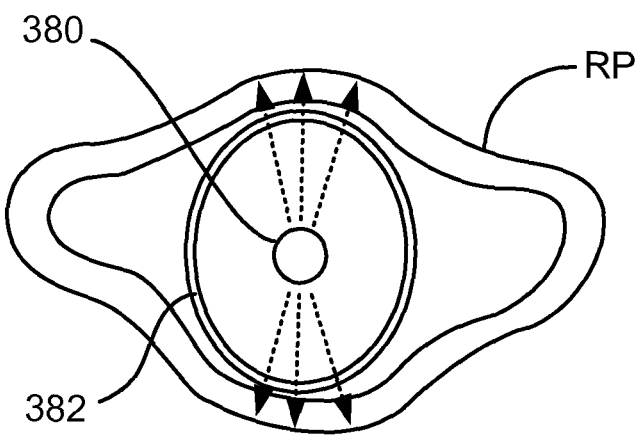

As shown in FIGS. 35A and 35B, a catheter 380 carries a distal balloon 382 having a plurality of infusion holes or ports thereon. The holes are typically deposed on the top and bottom of the balloon so that they will deliver substances directly into the wall of the renal pelvis RP, as shown in FIG. 35B. Preferably, a vacuum is applied to the renal pelvis to engage the holes against the tissue for targeted placement.

Figure 36A:
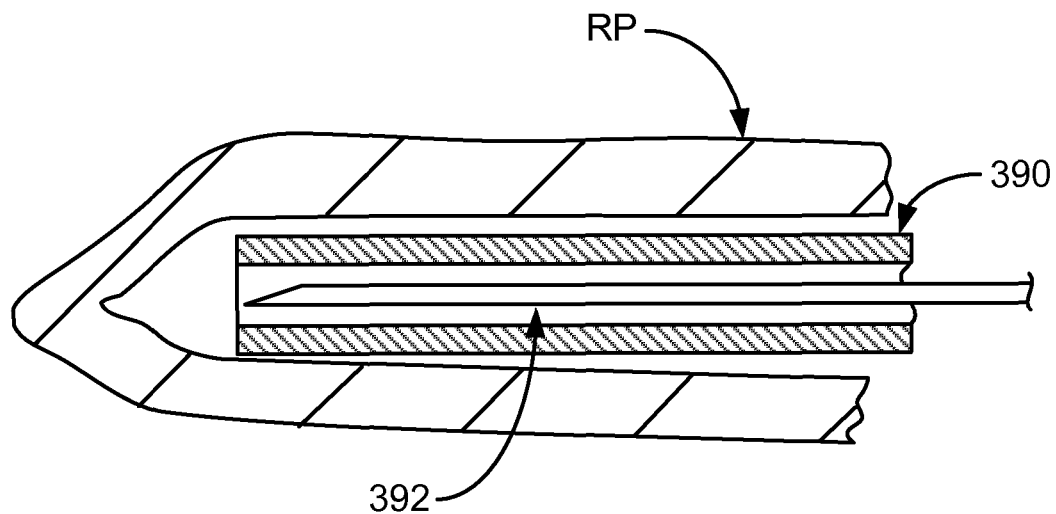
FIGS. 36A and 36B show a catheter with drug delivery needle both inside a sheath and deployed into the renal pelvic tissue.
Figure 36B:
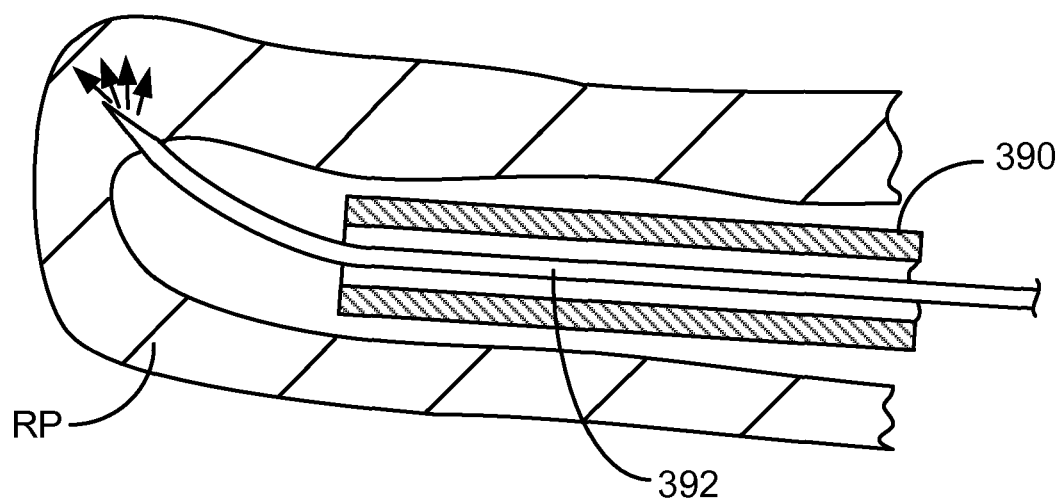

As shown in FIGS. 36A and 36B, a catheter 390 carries a deployable needle 392. The catheter is positioned inside the renal pelvis RP, and the needle is deployed, to pierce through the wall of the renal pelvis. Agents such as ethanol can then be delivered through the needle into the tissue to deactivate the renal nerves. Note that while the figures show the needle deploying from the distal tip of the catheter, the needle or a plurality of needles can alternatively exit through side holes in the catheter. A vacuum will preferably be used to approximate the tissue to the catheter and facilitate needle penetration.

Figure 37:
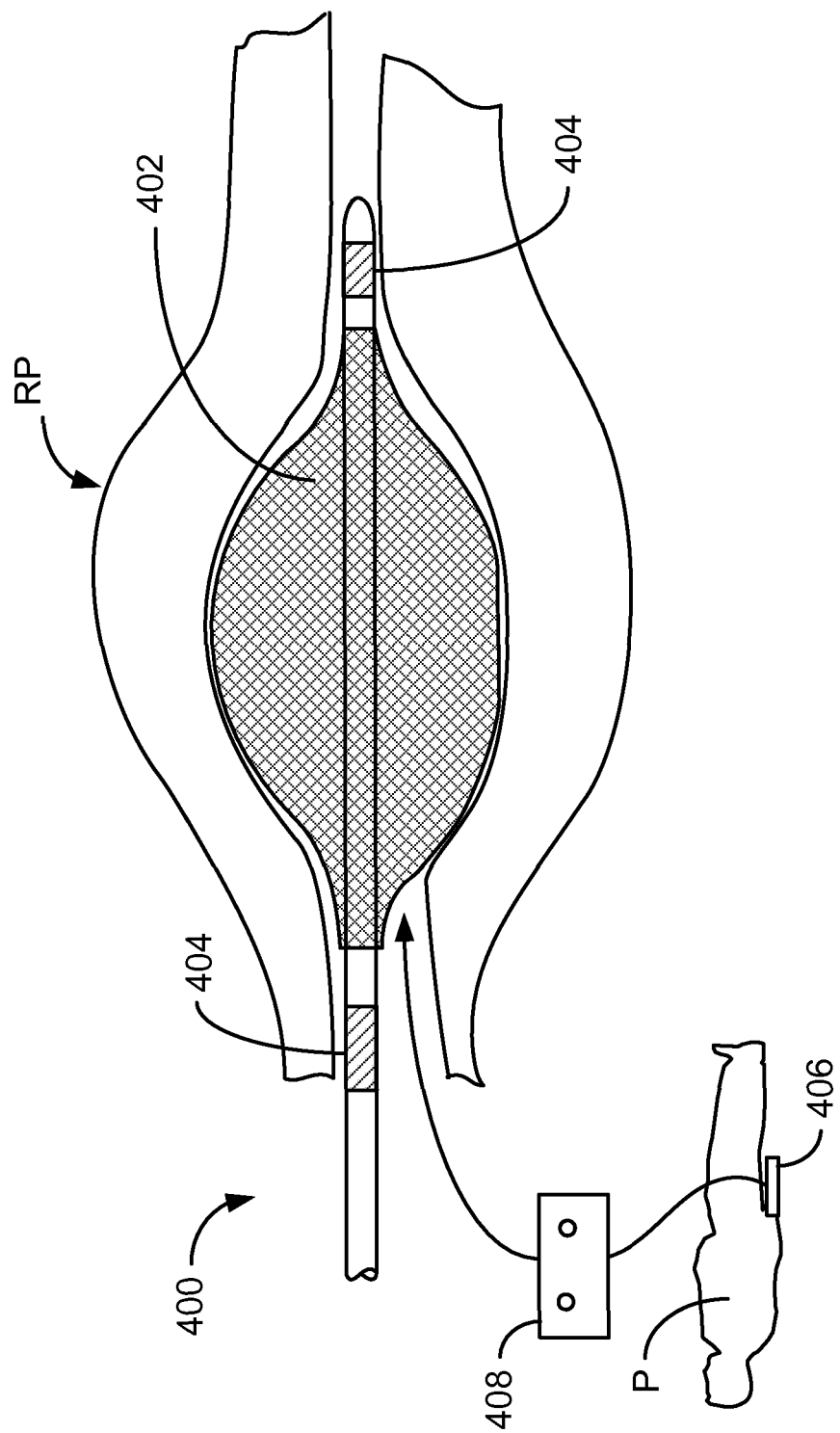
FIG. 37 shows a catheter system with expandable mesh for iontophoretic drug delivery.
Figure 38A:
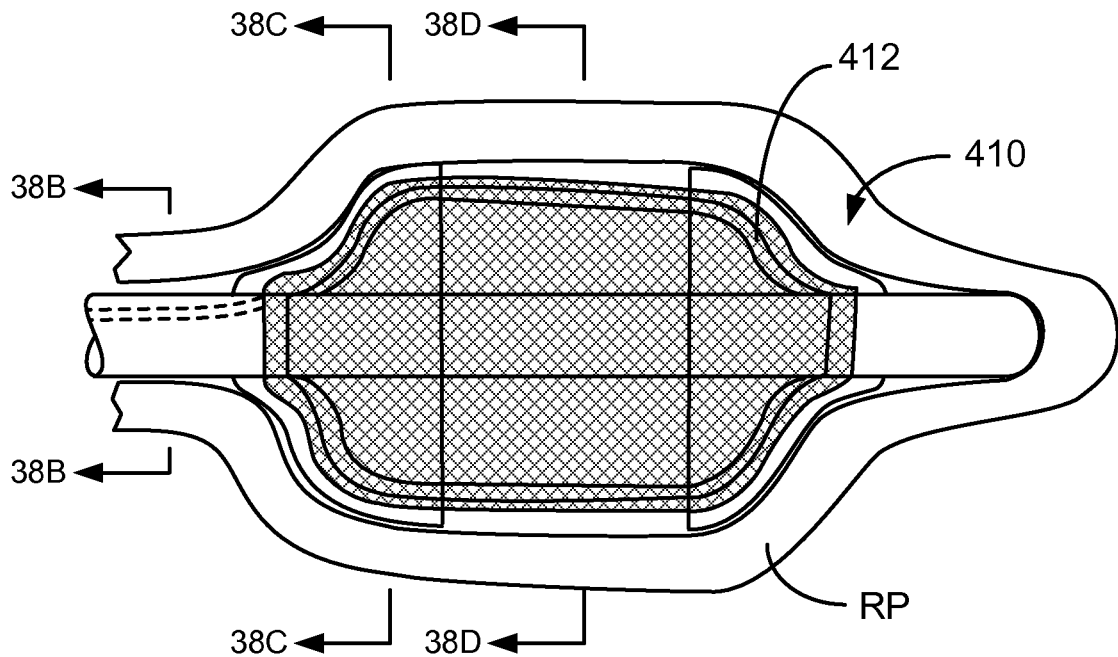
FIGS. 38A-38D show a drug delivery catheter with mesh, silicone, and balloon components.
Figure 38B:
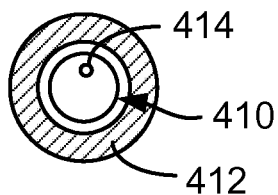
Figure 38C:
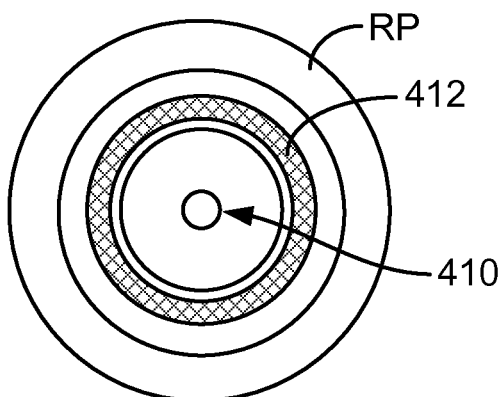
Figure 38D:
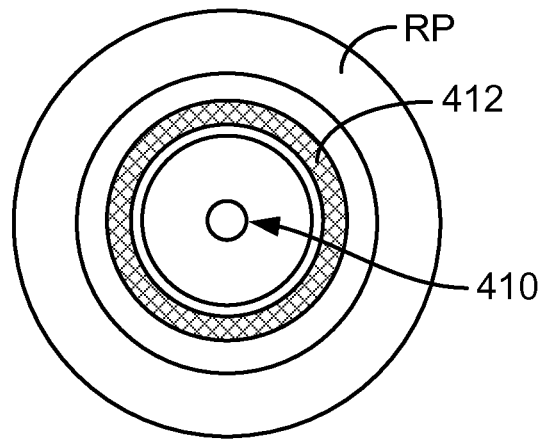
Figure 39:
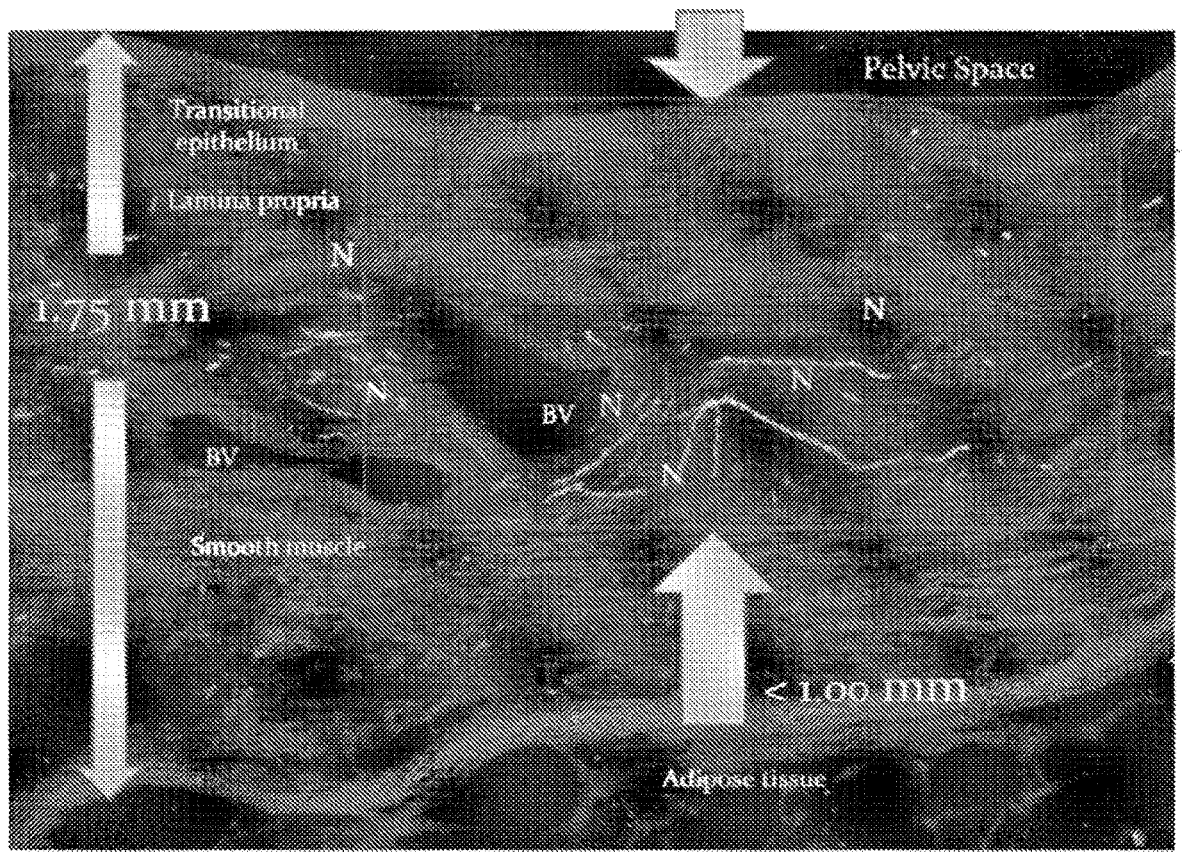
FIG. 39 shows a magnified cross section of renal pelvic tissue with the letter "N" illustrating nerves.
Figure 40:
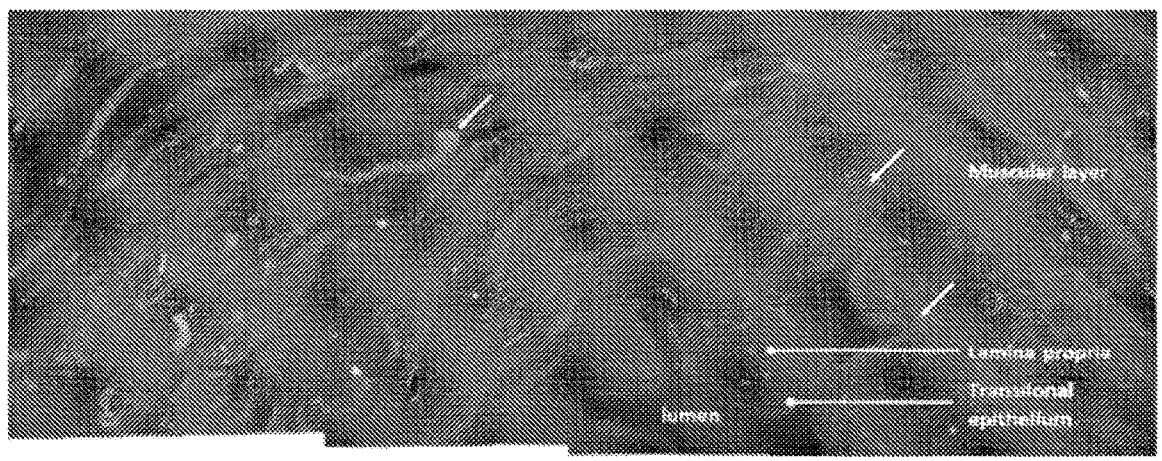
FIGS. 40-42 show magnified cross sections of ureteral tissue with arrows pointing to nerves.
Figure 41:
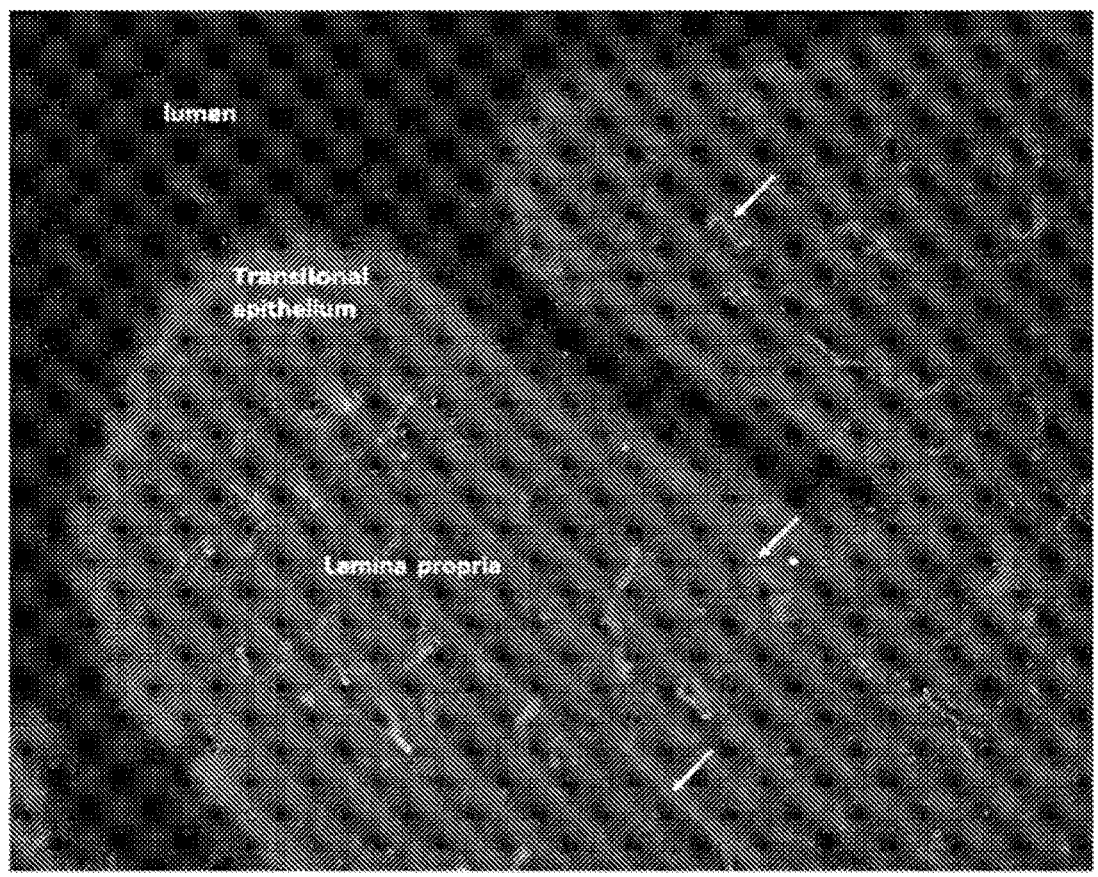
Figure 42:
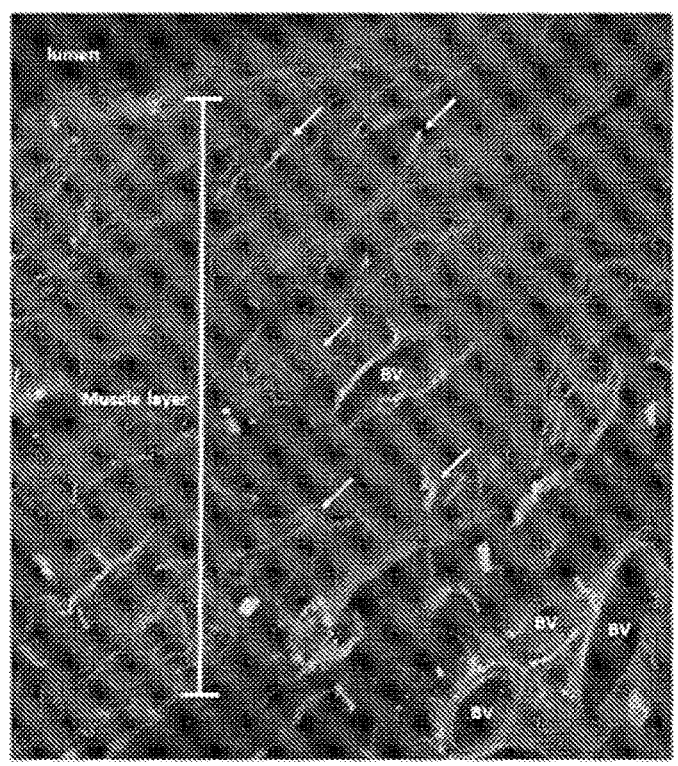

As shown in FIG. 37, an iontophoresis catheter 400 carries an electrically conductive, radially expansible cage 402 at its distal end. Iontophoresis is a physical process in which ions flow diffusively in a medium driven by an applied electric field. By applying an electrical potential, agents can be selectively absorbed by tissue. The electrically conductive, radially expansible cage 402 is radially expanded to contact the renal pelvis walls and acts as an anode. A nerve affecting agent can then be injected to the site and will be absorbed by the tissue at the mesh/tissue interface. The cathode can be provided by electrodes 404 on the catheter and/or an external cathode pad 406 on the patient's P skin. The cage and the cathodes are connected to a suitable power supply 408.

As shown in FIGS. 38A-38D, a balloon catheter 410 carries a balloon 412 covered by a sheath or jacket formed from a mesh covered by a silicone or other elastomeric material. Silicone sleeves are placed over the proximal and distal ends of the mesh layer. The catheter has a fluid lumen 414 with an exit port adjacent a proximal end of the silicone, between the silicone and the catheter and into the mesh. Fluid is passed through the fluid lumen and flows in between the strands of the mesh which sandwiched between the balloon and the silicone. The fluid then exits the distal end of the proximal silicone and contacts the tissue between the two silicone sleeves. This allows for targeted delivery for nerve affecting agents. This design can also be used in vascular catheters to deliver drugs to vessel walls.

FIGS. 39-42 are images obtained by the inventors showing the renal pelvic nerves to be within 1 mm of the tissue surface. The devices of many embodiments are configured to particularly target this depth. As shown in FIGS. 39-42, the ureter is also rich with renal nerves. The devices of embodiments can also be configured to target nerves within the ureter in addition to or as an alternative to nerves in the renal pelvis.

Figure 43:
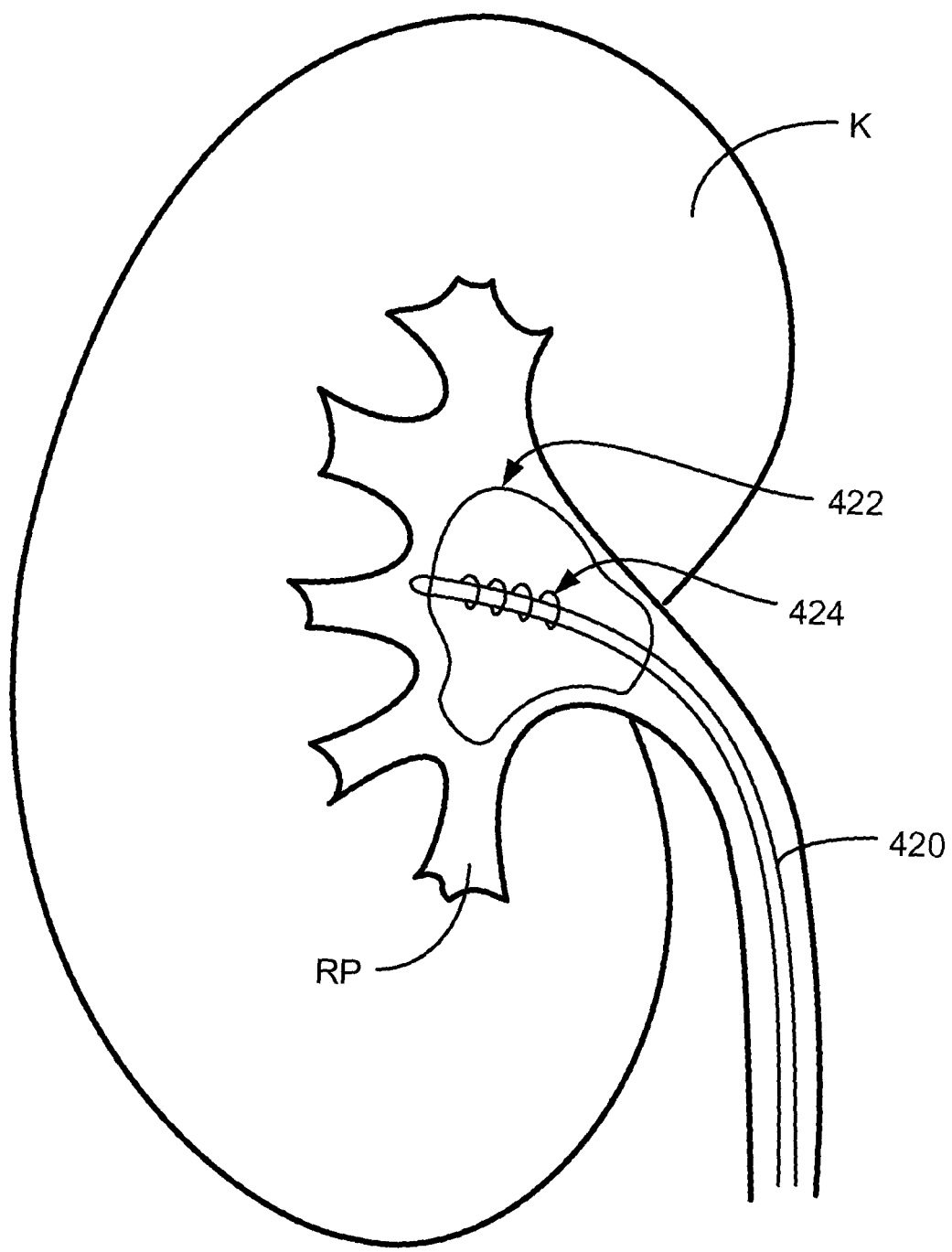
FIG. 43 shows a balloon catheter with heating coil.

As shown in FIG. 43, a catheter 420 carries a compliant or semi-compliant balloon 422 that is deployable in the renal pelvis RP. The balloon 422 is inflated with saline or other liquid. The balloon is sufficiently compliant to conform to the anatomy of the renal pelvis to maximize wall contact. A resistive heating coil 424 made from a suitably resistive material, such as Nichrome®, is located inside the balloon. The coil heats the liquid to 60° C., and the balloon is maintained in place for a suitable time period against the wall of the renal pelvis to achieve the desired nerve ablation. Thermocouples located on the catheter and on the coil and inside the balloon can be used to regulate temperature. Alternatively, the liquid can be heated outside the catheter and pumped through the catheter/balloon assembly.

Figure 44A:
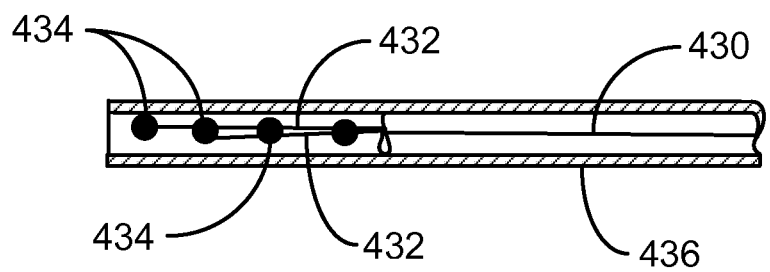
FIGS. 44A and 44B show a bifurcated superelastic alloy wire with ball electrodes.
Figure 44B:
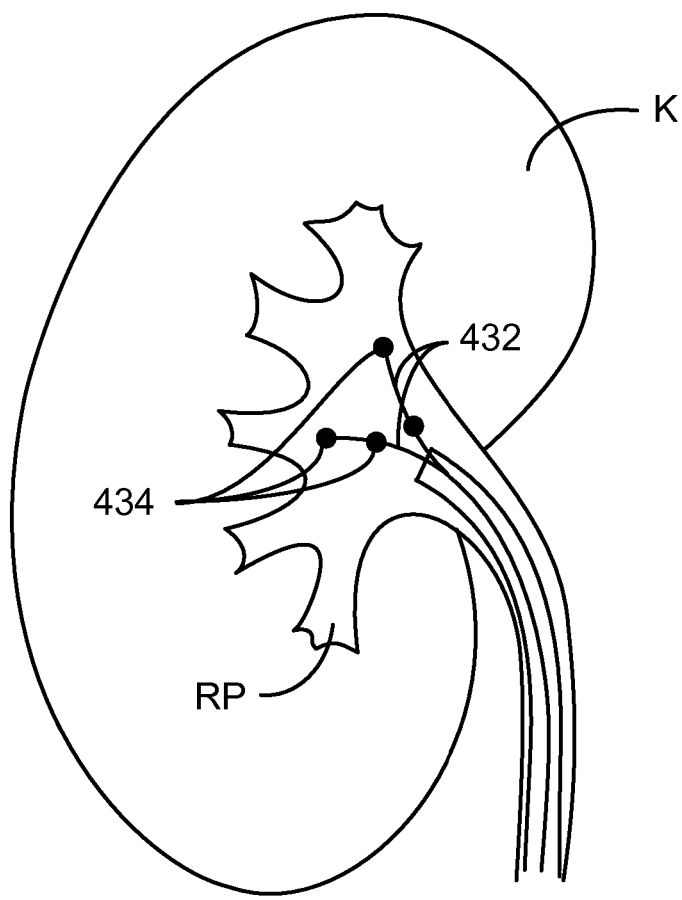

As shown in FIGS. 44A and 44B, a Nitinol® or other superelastic alloy wire 430 is bifurcated into branches 432 its distal end. Ball electrodes 434 are secured to each branch at alternating locations so that the branches can be collapsed within the lumen of a delivery sheath or catheter 436 as shown in FIG. 44A. The branches carrying the electrodes can be deployed out of the catheter and into the renal pelvis RP. The branches are biased apart to achieve spacing of the ball electrodes. RF energy is applied through the wire to the ball electrodes and discrete lesions are formed on the tissue wall. A vacuum can be applied to embed the ball electrodes into the tissue surface.

Figure 45:
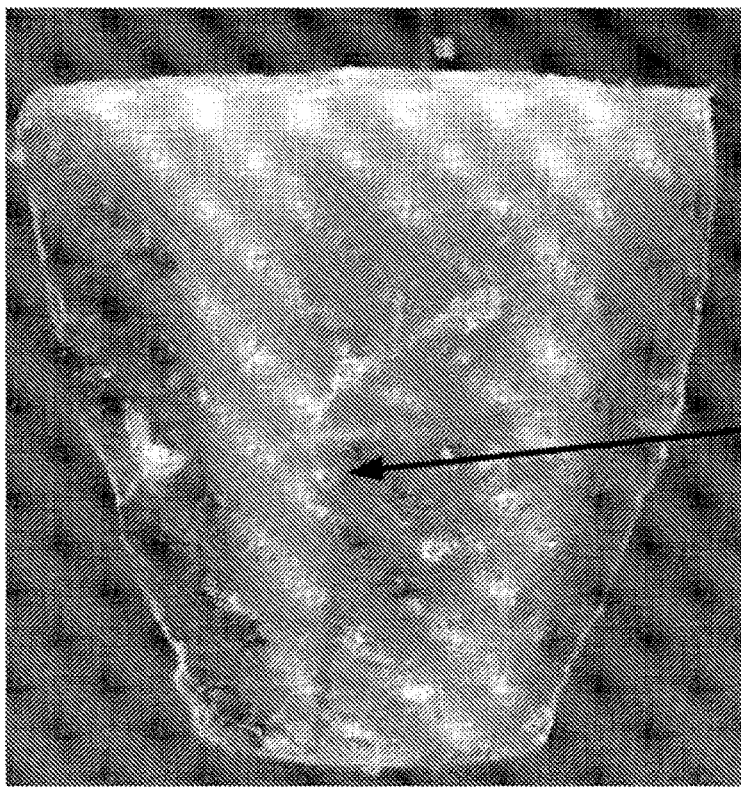
FIG. 45 shows a ball electrode device in temperature sensitive gel.
Figure 46:
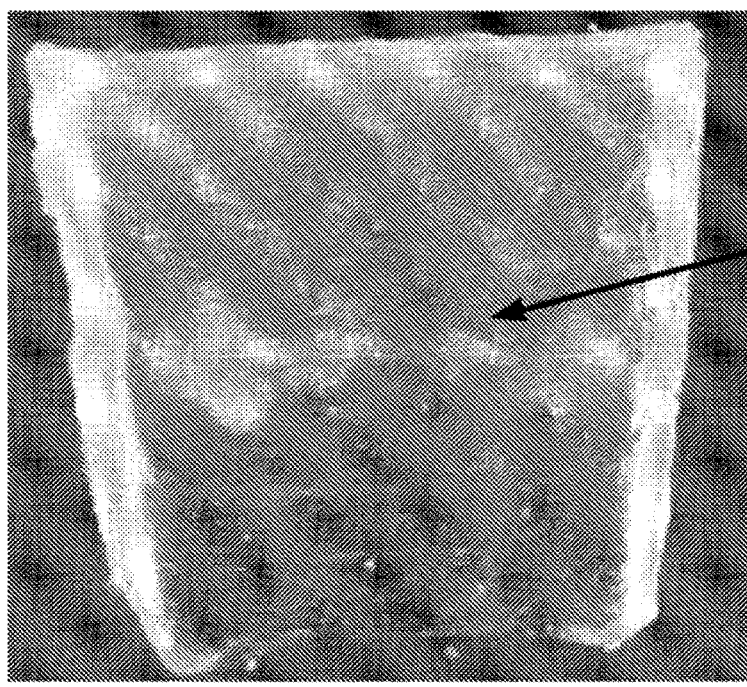
FIG. 46 shows a white clouding of the gel where the temperature was increased over 50 C.° from the device.

Applying RF or other heating means to the renal pelvis requires a balance of time and temperature. Too much energy will damage function of the renal pelvis. Not enough energy will prevent effective renal denervation. Experimentation has shown that a temperature in the range from 55° C. to 65° C., preferably 60° C. applied for a time in the range from 1 minute to 3 minutes, preferably 2 minutes, is optimal to achieve ablation of nerves surrounding the renal pelvis and in some cases the ureter. As shown in FIG. 45, ball electrodes are inserted into a gel phantom that mimics tissue electrical and thermal characteristics. The gel changes to a white color when the temperature is brought above 50° C. as shown in FIG. 46.

Many of the above-described device designs dilate, stretch, or otherwise tension the wall of the renal pelvis during the application of energy, the mechanical treatment of the renal pelvic wall, or substance delivery. This stretching is advantageous as it thins the tissue wall bringing the nerves closer to the treatment elements, particularly for the delivery of RF current.

EXPERIMENTAL

Background. Endovascular renal denervation is known to produce useful blood pressure (BP) reductions. The data below demonstrate the safety and effectiveness of renal denervation by delivery of radiofrequency energy across the renal pelvis utilizing the natural orifice of the urethra and the ureters. This open-label, single-arm feasibility study enrolled patients with uncontrolled hypertension despite antihypertensive drug therapy. The primary effectiveness endpoint was the change in ambulatory daytime systolic BP (SBP) 2 months following renal pelvic denervation.

Surprisingly, the data further demonstrated a small but significant increase in eGFR and a significant decrease in mean serum creatinine, both of which correlate with a decreased risk of kidney disease and associated morbidities, including a reduced risk of stroke, congestive heart failure, and end-stage renal disease, as well as improved hormone function, including reductions in renin, aldosterone, and angiotensin.

Methods

Participants. Adults between the ages of 18 and 70 with uncontrolled hypertension were eligible for the study at either of two study sites. While continuing to take their background antihypertensive therapy of up to three antihypertensive medications, mean daytime systolic blood pressure measured by 24-hour ambulatory blood pressure monitoring was required to be at least 135 mm Hg and less than 170 mmHg, with mean daytime diastolic blood pressure less than 105 mm Hg. For those not receiving medications, mean daytime systolic blood pressure was required to be at least 140 mm Hg and less than 170, with mean daytime diastolic blood pressure less than 105 mm Hg. However, while the protocol allowed for participation of both on-med and off-med patients, a decision was made early during the patient enrollment period to recruit only those patients receiving antihypertensive medications. This study report is based on the 18 patients on antihypertensive drug therapy.

Exclusion criteria included an estimated glomerular filtration rate (eGFR) under 45 mL/min/1.73 m$^2$ (calculated via the CKD-EPI Creatinine Equation, National Kidney Foundation), type I diabetes, clinically significant structural heart disease and secondary hypertension. The study (NCT05440513) was approved by the local Ethics Committee. Written informed consent was obtained from all patients before study enrollment.

Study Procedures. Baseline evaluation included measurement of automated office blood pressure and 24-hour ambulatory blood pressure monitoring along with laboratory assessment of serum and urine parameters according to a standard routine. Following collection of blood and urine specimens, patients were seated and allowed to rest for 5 minutes prior to use of an automated blood pressure measurement device (HEM-907XL, Omron Healthcare, Bannockburn, IL) which recorded blood pressure in each arm. Office blood pressure measurement was recorded in triplicate with one-minute separations between measurements. The arm with higher blood pressure at the baseline assessment was used for all subsequent measures. Study personnel would then witness the antihypertensive medication self-administration before positioning the arm cuff for ambulatory blood pressure monitoring (ABP OnTrak 90227, Spacelabs Healthcare, Snoqualmie, WA) on the same arm as used for office blood pressure measurements. Blood pressure was measured every 20 minutes during the day (0600-2159 h) and every 30 minutes at night (2200-0559 h). Patients would return the following day, at a time to assure at least 24 hours of blood pressure recording time, for the device to be removed. Additional baseline assessments included a pregnancy test where relevant, electrocardiogram, echocardiogram, computed tomographic (CT) urography and renal ultrasound.

For those patients meeting entry criteria, renal pelvic denervation was performed via the use of the Verve Medical Phoenix™ system. (Verve Medical, Paradise Valley, AZ). This system includes an RF generator and monopolar ablation device with 4 spherical electrodes, similar to device 230 of FIG. 20. A dispersive electrical grounding pad was used (Universal Electrosurgical Pad with Cord, REF 9135-LP, 3M, Saint Paul, MN). The ablation device is placed into the renal pelvis following insertion of a 0.035"-0.038" soft tip guidewire into the bladder under visual guidance via rigid cystoscope, which is then advanced under fluoroscopy past the uretero-pelvic junction. A sheath (Destina™ Twist, Oscor, Inc., Palm Harbor, FL) is passed over that wire to allow for placement of the Phoenix™ ablation device into the pelvis, beyond the ureteropelvic junction. The generator delivers up to 30 watts of power via this ablation device, which has 4 spherical conductors on a nitinol helix designed to expand into the renal pelvis and abut the uroepithelial lining. When activated, energy is delivered to increase the temperature to 60° ° C. within 20 seconds and maintain 60° C. for 2 minutes. Energy is delivered for a single cycle, then repeated in the other kidney. At the completion of the ablation, physicians were permitted to place ureteral stents at their discretion, which, when deployed, remained in place until the day 14 visit.

Unless clinically necessary, physicians and subjects were encouraged not to terminate or add antihypertensive medications following renal pelvic denervation until completing the Month 2 assessments, with addition of medicines permitted thereafter if office blood pressure continued to be uncontrolled. Post-treatment assessments were scheduled for Day 1, Day 14 and Month 1 with primary endpoints of safety and effectiveness performed at Month 2. At each visit, subjects underwent clinical evaluation including pain assessment and office blood pressure measurement.

At Day 14, Month 1 and Month 2, specimens were obtained for blood and urine testing. At Month 1 and 2, Ambulatory blood pressure monitoring was performed. At Month 1, renal ultrasound and CT urography were repeated. Concomitant medications were recorded, and adverse events were elicited at every visit.

Safety events of interest were defined in the protocol as: cardiovascular (including acute coronary syndrome, stroke, acute kidney injury, or death), device and procedure-related adverse events, urologic events (i.e., infections, hematuria, pain, urinary incontinence and/or obstruction within 14 days of the procedure) and clinically significant changes in serum and urine biochemistry.

Statistical Analysis.

The objectives of the study were to assess the safety and effectiveness of the Verve Medical Phoenix™ system. Safety was assessed through laboratory, urologic imaging and clinical events, included adverse events, serious adverse events and treatment-emergent adverse events.

The primary effectiveness endpoint was the mean change in daytime systolic blood pressure measured by ABPM from baseline to 2 months. Additional endpoints included changes in 24-hour ambulatory blood pressure monitoring and office blood pressure.

Summary single timepoint measurements and baseline characteristics are expressed as mean±SD (standard deviation) or percentages (%). Changes in continuous variables from baseline are shown as mean difference with 95% confidence intervals (CI). P values for individual time points are based on paired t-tests with changes through the assessment at Month 2, the primary endpoint, are based of mixed models (i.e., random effects models) using the Satterthwaite approximation for degrees of freedom for the overall p-value (F-statistic) and confidence intervals (t-statistic). Statistical analysis was performed using R version 4.1.3 (R Core Team 2022). A value of p<0.05 was considered significant. Subgroup analyses considered a p<0.10 as significant. DH had full access to all data from the clinical trial and was responsible for the integrity of the data used in the analysis.

Results

Eighteen patients (mean age 56±12 years) were enrolled on average antihypertensive drug intake of 2.7 daily. Renal pelvic denervation reduced mean daytime SBP by 19.4 mmHg (95% CI: −24.9, −14.0, p<0.001) from its baseline of 148.4±8.7 mm Hg. Mean nighttime (−21.4 mmHg, 95% CI: −29.5, −13.3) and 24-hour (−20.3 mmHg, 95% CI: −26.2, −14.5) SBP fell significantly (p<0.001) as did the corresponding diastolic BP (DBP) (p<0.001). Office SBP decreased from 156.5±12.3 mmHg by 8.3 mmHg (95% CI: −13.2, −3.5, p=0.002) within 24 hours post-procedure and by 22.4 mmHg (95% CI: −31.5, −13.3, p<0.001) by 2 months. Office DBP was reduced (p=0.001) by 2 months. Mild transitory back pain followed the procedure, but there were no serious adverse events. Serum creatinine decreased by 0.08 mg/dL (p=0.02) and estimated glomerular filtration rate increased by 7.2 mL/min/1.73 m$^2$ (p=0.03) 2 months following ablation procedure.

Figure 47:
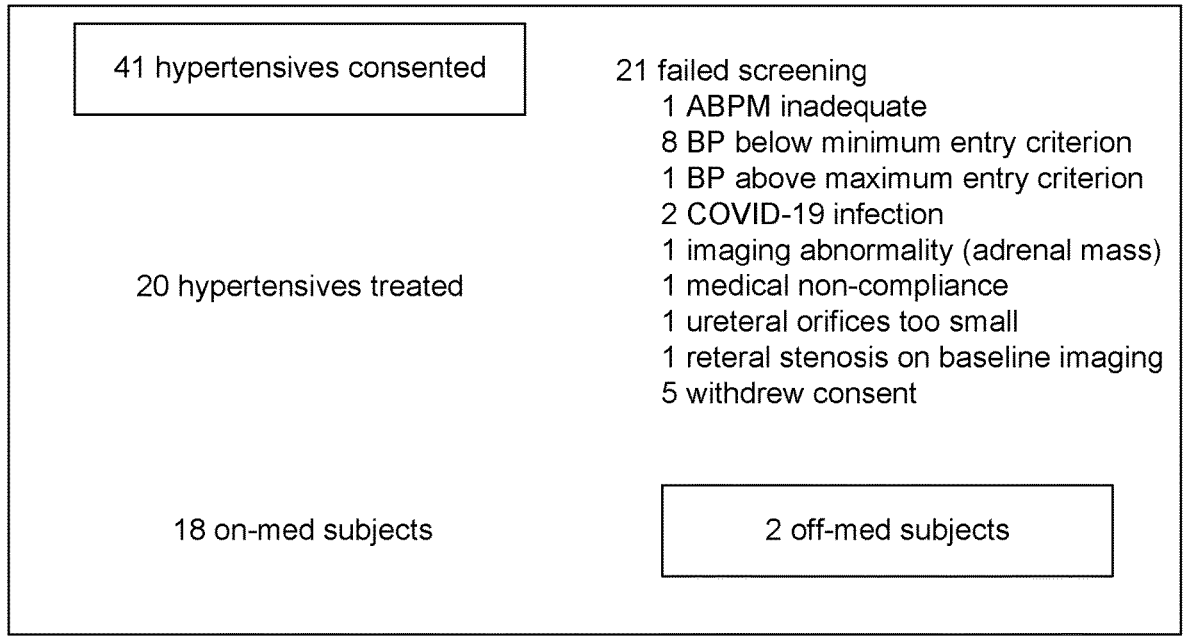
FIG. 47 is a consort diagram.

Baseline. Of 41 patients who signed informed consents, 21 were excluded (FIG. 47) including ten who were disqualified for failing to meet the study's blood pressure entry criteria, two due to COVID-19 infection, one identified with ureteral stenosis on baseline imaging, and one with ureteral orifice too narrow to allow for the sheath to be advanced, in whom the option of pre-stenting to enable performance of renal pelvic denervation 1-2 weeks later in this latter case was not employed.

The study population included 18 patients receiving antihypertensive medicines (Table 1) and two not receiving blood pressure lowering drugs, with the focus of this report on those patients receiving antihypertensive therapy. Average age was 56±12 years, the cohort included 7 women and 11 men who, on average, were treated with 2.7 antihypertensive drugs (Table 1).

TABLE 1

Select baseline characteristics of on-med subjects (n {%}, mean (SD))

| Characteristic | n = 18 |
|---|---|
| Age | 56 (12) |
| Female subjects | 7 (39%} |
| Body mass index (m/kg$^2$) | 31.6 (4.5) |
| Diabetes mellitus | 3 (17%) |
| Myocardial infarction | 2 (11%) |
| Coronary artery disease | 3 (17%) |
| estimated Glomerular Filtration Rate (ml/min/1.73 m$^2$) | 80 (18) |
| Number of hypertension drugs | 2.7 (0.5) |
| Angiotensin converting enzyme inhibitor | 16 (89%,) |
| Angiotensin receptor blocker | 1 (5.6%) |
| Calcium channel blocker | 14 (78%) |
| Beta-blocker | 7 (39%) |
| Diuretic | 10 (56%) |
| Oral diabetic | 3 (17%) |
| Statin | 10 (56%) |

Procedural Safety. No serious intra-procedural adverse events were observed. Following renal pelvic denervation, bilateral double-J ureteral stents were placed at investigators' discretion in 9 of 18 patients, which were removed in the office at the 14-day follow-up without complication.

Adverse Events. There were no serious adverse events and no treatment-emergent adverse events. In those subjects without stent placement, 5/9 reported back/flank pain, while 7/9 who had stents placed reported some pain or discomfort. By day 14, none of the nine patients without stents had pain while 3 patients with stents in place reported mild back or flank pain that persisted following hospital discharge but which resolved prior to or one day following removal of the stents (with average pain score of 3 out of 10 at day 14). In one subject, a renal stone 2.5-3 mm was evident one month after treatment, in whom the baseline study showed evidence of microliths and calcifications, indicating stone formation prior to treatment. The site reported that there was no stone evident on ultrasound imaging at month 6 or month 12. The one subject with proteinuria on a scheduled urinalysis had repeat study 4 days later with no evidence of proteinuria. There were no interventions or concomitant therapies for either of these two patients, and both were categorized as mild and resolved. Nonetheless, the investigator listed these as adverse events. One patient's hemoglobin level dropped from 11.6 g/dL at baseline to 9.8 g/dL at month 1 with initiation of iron anemia at month 6 follow-up. No adverse events are ongoing (Table 2).

TABLE 2

Safety and tolerability of renal pelvic denervation.

| Event | n (%) |
|---|---|
| Post-procedure back/flank pain* | 12 (67%) |
| Persistent back/flank pain | 0 (0%) |

TABLE 2-continued

Safety and tolerability of renal pelvic denervation.

| Event | n (%) |
|---|---|
| Urinary tract infection† | 2 (11%) |
| Cystitis | 0 (0%) |
| Proteinuria | 1 (6%) |
| Anemia | 1 (6%) |
| Renal stone | 1 (6%) |
| Perforation | 0 (0%) |
| Hypertensive crisis | 0 (0%) |
| Acute kidney injury | 0 (0%) |
| Renal failure | 0 (0%) |
| Acute coronary syndrome | 0 (0%) |
| Stroke | 0 (0%) |
| Hospitalization | 0 (0%) |
| Death | 0 (0%) |
| Treatment-emergent adverse event | 0 (0%) |
| Serious adverse event | 0 (0%) |

*Post procedure back l flank pain was evident by day 14 only in 3 subjects - each of whom had stents in place - with average score of 3 out of 10, with pain resolved within 1 day of stent removal.
†Both urinary tract infections responded to treatment with oral antibiotics.

Figure 48A:
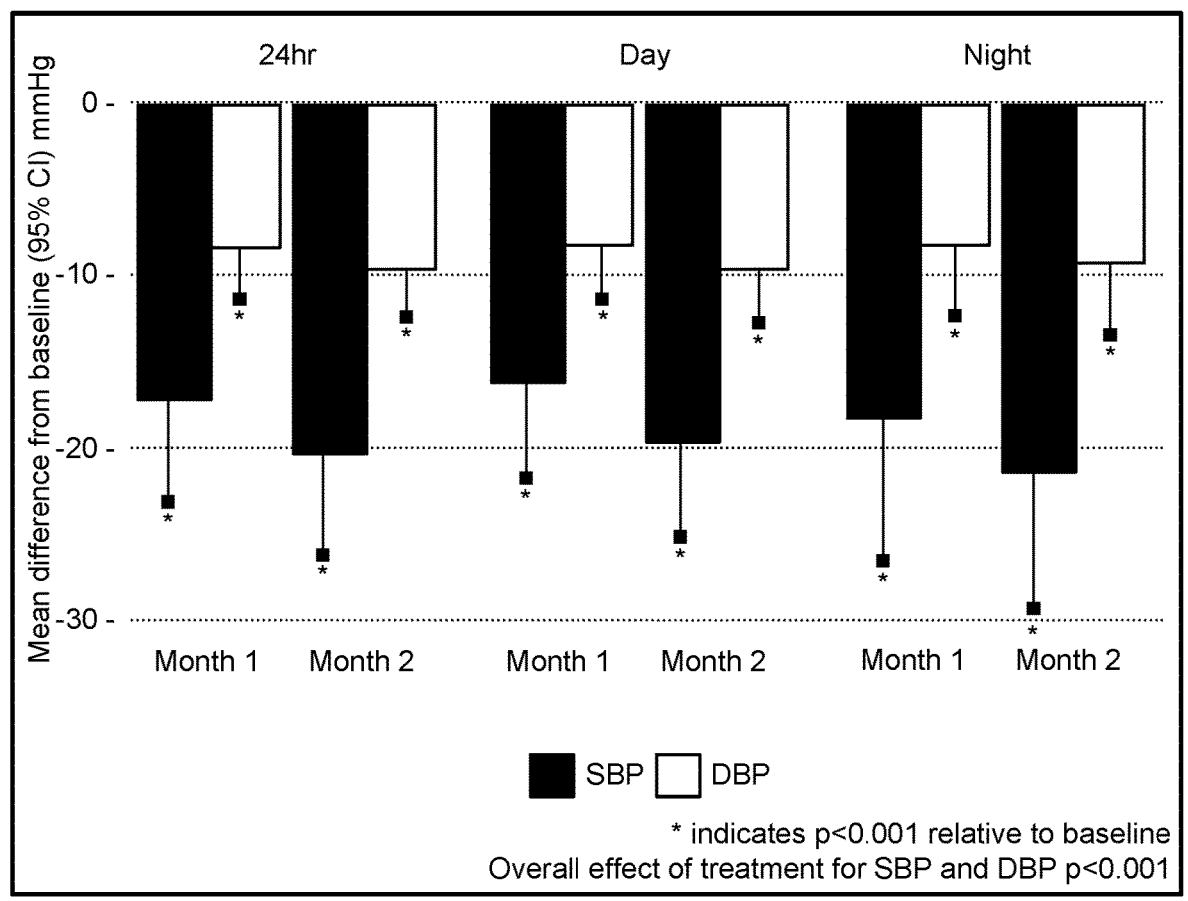
FIGS. 48A and 48B are bar charts showing the effect of renal pelvic denervation on ambulatory blood pressure reflected by (a) changes 1 and 2 months after ablation (* indicates p<0.001 by t-test, overall effects for changes in systolic blood pressure (SBP) and diastolic blood pressure (DBP) through Month 2 by linear mixed model at p<0.001) with (b) persistent 24-hour effects on SBP and DBP from baseline to month 2 (means with standard errors calculated by averaging all blood pressures taken during that hour).
Figure 48B:
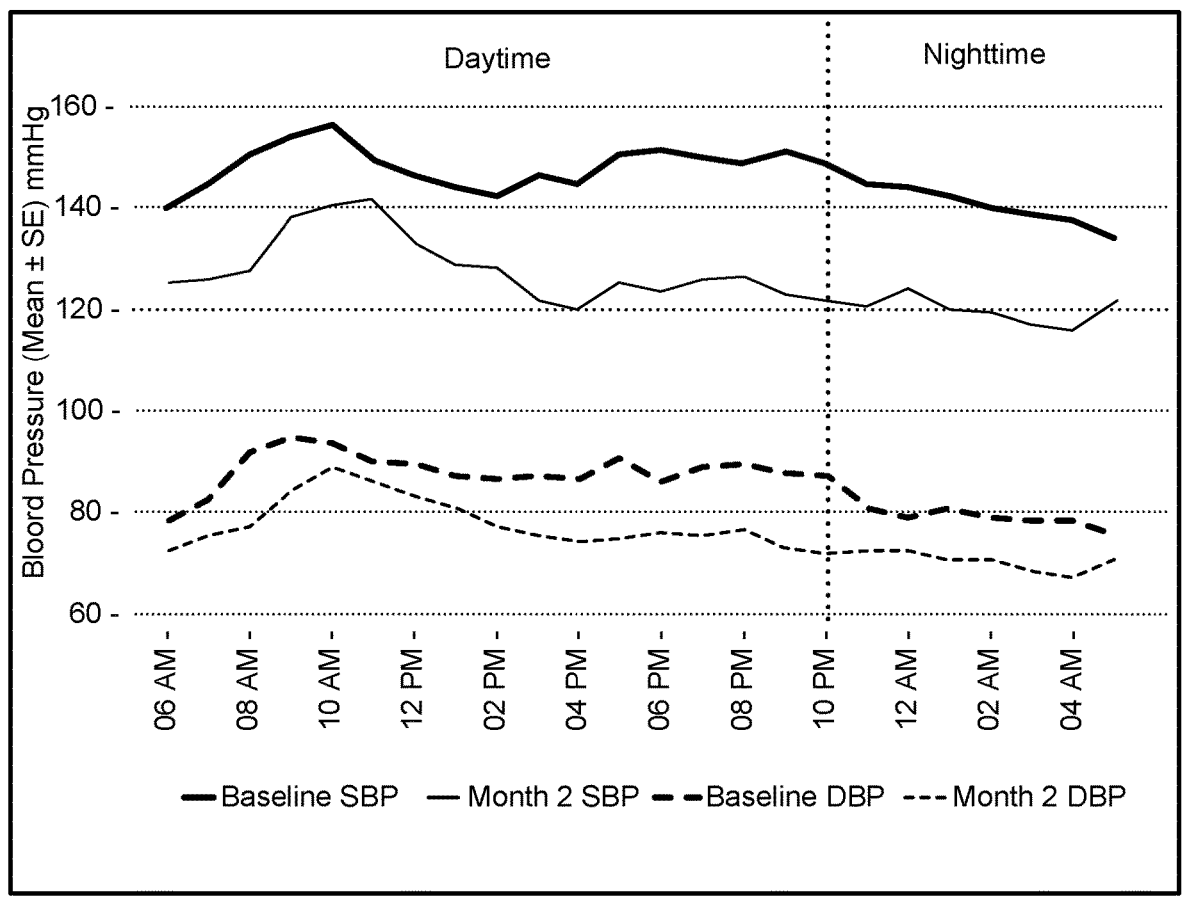

Effect on Blood Pressure. The primary effectiveness endpoint of daytime systolic blood pressure at 2 months post-procedure was significantly reduced by 19.4 mm Hg (95% CI: −24.9, −14.0, p<0.001). There were also significant reductions in mean 24-hour systolic blood pressure by 20.3 mm Hg (95% CI: −26.2, −14.5, p<0.001) and nighttime systolic blood pressure by 21.4 mm Hg (95% CI: −29.5, −13.3, p<. 001). The corresponding changes for diastolic blood pressure were 9.7 mm Hg daytime (95% CI: −12.7, −6.8), −9.2 mm Hg nighttime (95% CI: −13.3, −5.0), and 9.6 mm Hg over 24 hours (95% CI: −12.5, −6.6). All these diastolic blood pressure changes were significant (p<0.001). (FIG. 48A) The changes in ambulatory blood pressure over 2 months following renal pelvic denervation are evident over 24 hours, including an effect during the morning blood pressure surge. (FIG. 48B)

Figure 49:
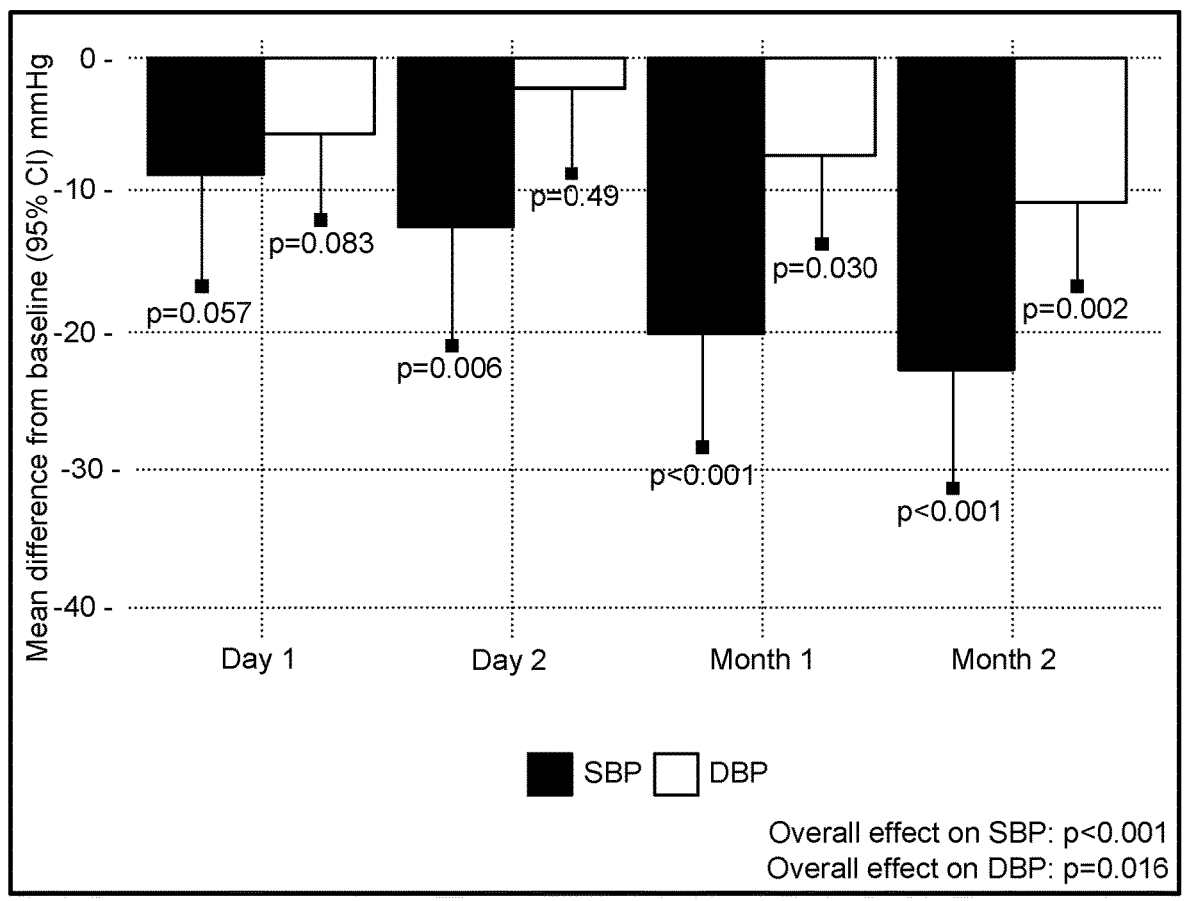
FIG. 49 is a bar chart showing change from baseline in office blood pressure (p-values for changes in systolic and diastolic blood pressure at each time point and for overall effects by linear mixed model analysis).
Figure 50:
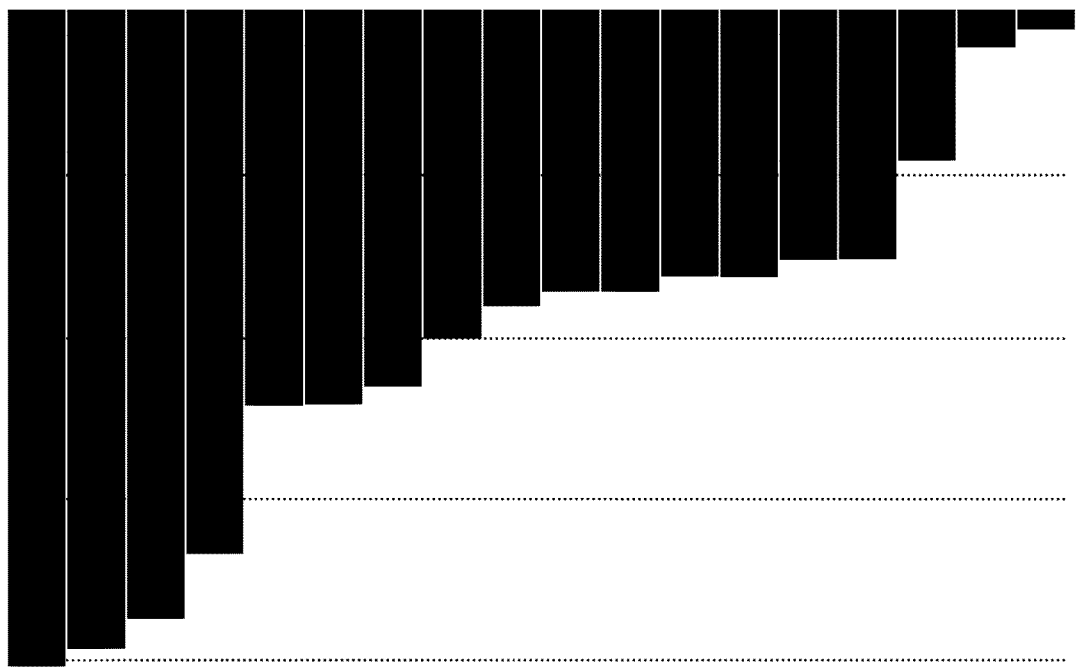
FIG. 50 shows waterfall plots of 24-hour ABPM (Ambulatory Blood Pressure Monitoring) changes for each subject at Month 2.

Office systolic blood pressure was reduced by 22.4 mm Hg (95% CI: −31.0, −13.8, p<0.001) 2 months post-procedure (FIG. 49). Office blood pressure measurements showed significant reductions at each assessment following renal pelvic denervation as early as one day post-procedure (FIG. 50). The decreases in office systolic blood pressure (p=0.002) and diastolic blood pressure (p=0.023) at day one post renal pelvic denervation were statistically significant by t-test but not by mixed model analysis (p=0.057 and p=0.083 for systolic blood pressure and diastolic blood pressure, respectively). By linear trend test from the time of the procedure to the 2-month endpoint, the progressive decrease in systolic blood pressure over time was statistically significant (p=0.001), whereas the decrease in diastolic blood pressure over time was not (p=0.07).

By 2 months post procedure, mean daytime systolic blood pressure fell in 17 of 18 (94%) subjects and mean 24-hour systolic blood pressure fell in all 18 patients (FIG. 50). Mean daytime systolic blood pressure dropped by at least 5 mm Hg in 17 (94%) out of 18 subjects and in 16 (89%) out of 18 patients for 24-hour systolic blood pressure. Mean systolic blood pressure dropped at least 10 mm Hg in 16 (89%) of 18 patients during daytime systolic blood pressure and in 15 (83%) of 18 patients over mean 24 hours systolic blood pressure, and by at least 15 mm Hg in 12 (67%) of 18 patients during daytime systolic blood pressure and in 15 (83%) of 18 patients over mean 24 hours systolic blood pressure. No subjects experienced an increase in mean daytime or 24-hour systolic blood pressure at month 2 post renal pelvic denervation.

Office heart rate on the first day increased compared to baseline following renal pelvic denervation (p=0.03) but was lower at months 1 and 2 (p<0.07). Overall treatment effects of renal pelvic denervation resulted in a significant reduction in office heart rate (p<0.001) but no significant changes in heart rate were observed in mean daytime, nighttime or 24-hours levels.

Exploratory analysis of the response in subjects with (n=8) compared to those without (n=10) isolated systolic hypertension did not suggest differences between these groups in any measure of change in systolic blood pressure, diastolic blood pressure or heart rate (p=0.08 by Hotelling's T-statistic). Univariate analyses suggested smaller reduction in daytime and 24-hour diastolic blood pressure for subjects with isolated systolic hypertension. Two months following ablation in these subjects with isolated systolic hypertension, 24-hour systolic blood pressure dropped by 16.8 mm Hg (95% CI: −25.8 to −7.7, p=0.003 by t-test) and diastolic blood pressure dropped by 6.1 mm Hg (95% CI: −9.6 to −2.6, p=0.004 by t-test).

Effects on Laboratory Assessments. There was a small but significant increase in eGFR (6.3 mL/min/1.73 m$^2$ at month 1 and 7.2 mL/min/1.73 m$^2$ at month 2. p=0.033 by mixed model) and a significant decrease in mean serum creatinine (0.08 mg/dL both at months 1 and 2, p=0.023 by mixed model). Hemoglobin dropped by 0.5 g/dL by day 14, by 0.8 g/dL at month 1 and by 0.7 g/dL at month 2 (p=0.001 by mixed model). Hematocrit dropped by 2.4% (p=0.007 by mixed model) by month 2. No significant changes were noted in sodium and potassium levels.

Chronic kidney disease is typically classified by stages from stage 1 to stage 5. Generally, with all numbers expressed in units of mL/min/1.73 m$^2$, stage 1 is indicated by a GFR of 90 or above, stage 2 covers GFR in a range between 60 and 89, stage 3 covers GFR in a range between 30 and 59, stage 4 covers GFR in a range between 15 and 29, and stage 5 is classified as having a GFR below 15. Although patients at all stages can benefit from treatment as described herein, treatment is particularly beneficial and indicated for patients at stages 3-5.

It is believed that, other than eGFR/GFR, there are other markers typically associated with kidney disease that can be used to select subjects for treatment according to embodiments herein, and that will respond positively to treatment. For instance, one indicator associated with kidney damage is the presence of albumin in a urine sample. This indicator may show that kidney issues exist even when eGFR is in a normal, stage 1, or stage 2 range. In a normally functioning kidney, little to no protein/albumin is passed from the blood to the urine by the glomerular capsules in the kidney. In a damaged kidney and/or due to high blood pressure, the glomerular capsules may to some extent be unable to prevent the passage of protein/albumin from the blood to the urine. This condition is known as albuminuria or proteinuria. It is a symptom associated with many different types of kidney disease and can be a significant risk factor for complications.

In an embodiment, one or more methods for measuring albumin is performed on a candidate. One known method is a dipstick method, where the candidate's urine is reacted with a stick that changes color to indicate protein levels in the urine. Another method collects a candidate's 24-hour production of urine and measures the amount of protein excreted in the urine over that timeframe. A normal range of albumin in the urine by this measure is <150 mg/day. Proteinuria is generally indicated when albumin levels exceed 500 mg/day, and levels that exceed 3.5 g/day are indicative of nephrotic syndrome. Where creatinine is also measured, another marker can be developed using the ratio of albumin to creatinine in a sample.

In an embodiment, efficacy of treatment can be measured by taking a baseline proteinuria reading, which may be used alone or in combination with other metabolic indicators to screen candidates "in" or "out" for treatment. At one or more timeframes after treatment (e.g., two weeks, one month, two months, six months, or twelve months), a second proteinuria reading is taken and compared to the baseline reading. A decrease in albumin measure should be expected when a patient responds positively to treatment.

All of the functionalities described in connection with one embodiment are intended to be applicable to other embodiments except where expressly stated to the contrary or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

While certain embodiments have been described, these embodiments have been presented by way of example only and are not intended to limit the scope of the present disclosure. Indeed, the novel methods, apparatuses and systems described herein can be embodied in a variety of other forms: furthermore, various omissions, substitutions and changes in the form of the methods, apparatuses and systems described herein can be made without departing from the spirit of the present disclosure. The accompanying claims and their equivalents are intended to cover such forms or modifications as would fall within the scope and spirit of the present disclosure.

What is claimed is:

1. A method for treating hypertension, the method comprising:
    inserting a sheath through a ureter of a patient into a renal pelvis of the patient such that a distal end of the sheath is positioned within the renal pelvis or within a transition region where the ureter expands to meet the renal pelvis;
    providing in the sheath an elongate member bearing a plurality of electrodes, the electrode-bearing member having an expanded shape when unconstrained and having a compact shape when constrained by the sheath;
    advancing the electrode-bearing member from the sheath such that the electrode-bearing member transitions from the compact shape toward the expanded shape;
    applying a vacuum to collapse the walls of the renal pelvis such that renal pelvic tissue of a renal pelvic wall of the renal pelvis contacts each of the electrodes of the plurality of electrodes of the electrode-bearing member; and
    applying radio frequency energy to the plurality of electrodes to contemporaneously create a plurality of discrete lesions in the renal pelvic tissue to damage and disrupt the function of nerves contained in the renal pelvic wall.

2. The method of claim 1, wherein the nerves are located in one or more smooth muscle layers within the renal pelvic wall.

3. The method of claim 1, wherein the plurality of discrete lesions extend 1 mm into the renal pelvic wall.

4. The method of claim 1, wherein the electrode-bearing member is comprised of superelastic shape memory material.

5. The method of claim 1, wherein the expanded shape is three-dimensional prior to applying a vacuum to help approximate the plurality of electrodes to tissue of the renal pelvic wall.

6. The method of claim 1, wherein the plurality of discrete lesions are created by raising the temperature of the plurality of electrodes to 60 degrees C. for two minutes.

7. The method of claim 1, wherein the plurality of discrete lesions are created by raising the temperature of the renal pelvic tissue proximate each of the plurality of electrodes above 50 degrees C.

8. The method of claim 1, wherein the expanded shape is serpentine.

9. The method of claim 1, wherein applying radio frequency energy damages nerves in adipose vascular tissue between smooth muscle layers of the renal pelvic wall.

10. The method of claim 1, wherein applying radio frequency energy damages nerves in urothelium or transitional epithelium regions of the renal pelvic wall.

* * * * *